(12) United States Patent
Yamaya

(10) Patent No.: US 11,298,002 B2
(45) Date of Patent: Apr. 12, 2022

(54) ENDOSCOPE COVER AND ENDOSCOPE

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 312 days.

(21) Appl. No.: 16/354,263

(22) Filed: Mar. 15, 2019

(65) Prior Publication Data

US 2019/0208992 A1 Jul. 11, 2019

Related U.S. Application Data

(63) Continuation of application No. PCT/JP2017/025146, filed on Jul. 10, 2017.

(30) Foreign Application Priority Data

Sep. 16, 2016 (JP) .............................. JP2016-181383

(51) Int. Cl.
*A61B 1/00* (2006.01)
*G02B 23/24* (2006.01)

(52) U.S. Cl.
CPC ............ *A61B 1/00096* (2013.01); *A61B 1/00* (2013.01); *A61B 1/00087* (2013.01); *G02B 23/2476* (2013.01)

(58) Field of Classification Search
CPC ... A61B 1/00096; A61B 1/00; A61B 1/00087; A61B 1/00098; A61B 1/00089;

(Continued)

(56) References Cited

U.S. PATENT DOCUMENTS 5,662,588 A * 9/1997 Iida ..................... A61B 1/00091
600/121
5,674,181 A * 10/1997 Iida ...................... A61B 1/0008
600/127

(Continued)

FOREIGN PATENT DOCUMENTS

JP 2007-236812 A 9/2007
WO WO 2016/021234 A1 2/2016

OTHER PUBLICATIONS

English translation of International Preliminary Report on Patentability dated Mar. 28, 2019, together with the Written Opinion received in related International Application No. PCT/JP2017/025146.

(Continued)

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscope cover includes a cover main body, a fragile portion, and a buffer portion. The cover main body includes a window and an annular portion. The window opens in a radial direction of a longitudinal axis of an insertion section. The annular portion is provided on a proximal side of the window along the longitudinal axis of the insertion section and surrounding the distal framing portion. The fragile portion is provided at a position on the annular portion which is adjacent to the window. The buffer portion is provided on the cover main body. The buffer portion includes an end portion. The end portion of the buffer portion is configured to reduce a force exerted from the distal side of the fragile portion onto the fragile portion along the longitudinal axis.

23 Claims, 36 Drawing Sheets

(58) Field of Classification Search
CPC ............ A61B 1/00091; A61B 1/00101; A61B 1/00135; A61B 1/00137; A61B 1/018; A61B 1/0615; A61B 1/126; G02B 23/2476; G02B 23/243
USPC .................... 600/121, 124, 125, 127, 129
See application file for complete search history.

(56) References Cited

U.S. PATENT DOCUMENTS

| | | | | |
|---|---|---|---|---|
| 5,730,701 | A * | 3/1998 | Furukawa | ............ A61B 1/0008 600/121 |
| 2004/0082836 | A1 * | 4/2004 | Hino | .................... A61B 1/0008 600/170 |
| 2007/0246506 | A1 * | 10/2007 | Hamazaki | .......... A61B 1/00101 227/175.1 |
| 2016/0270635 | A1 * | 9/2016 | Tanaka | ................ A61B 1/00098 |
| 2018/0249894 | A1 * | 9/2018 | Kolberg | ................ A61B 1/0011 |
| 2019/0059702 | A1 * | 2/2019 | Hosogoe | ................ A61B 1/018 |
| 2019/0117045 | A1 * | 4/2019 | Hosogoe | ............ A61B 1/00098 |

OTHER PUBLICATIONS

International Search Report dated Sep. 26, 2017 issued in PCT/JP2017/025146.

* cited by examiner

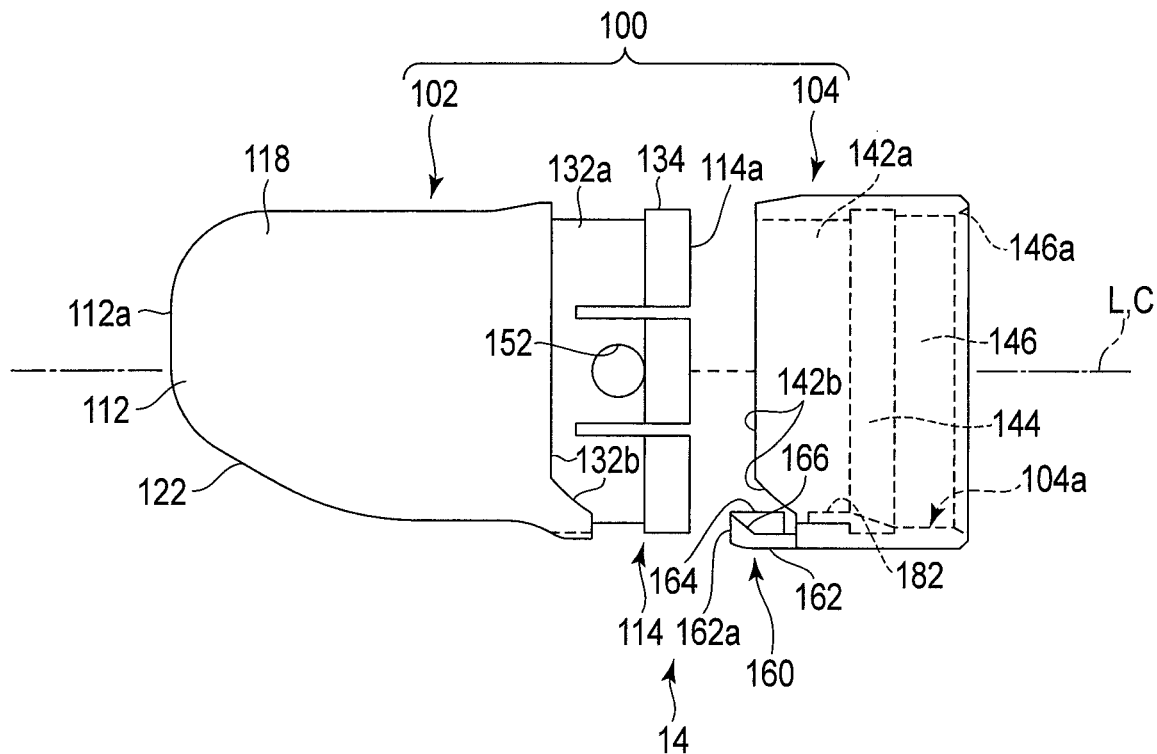
F I G. 4C
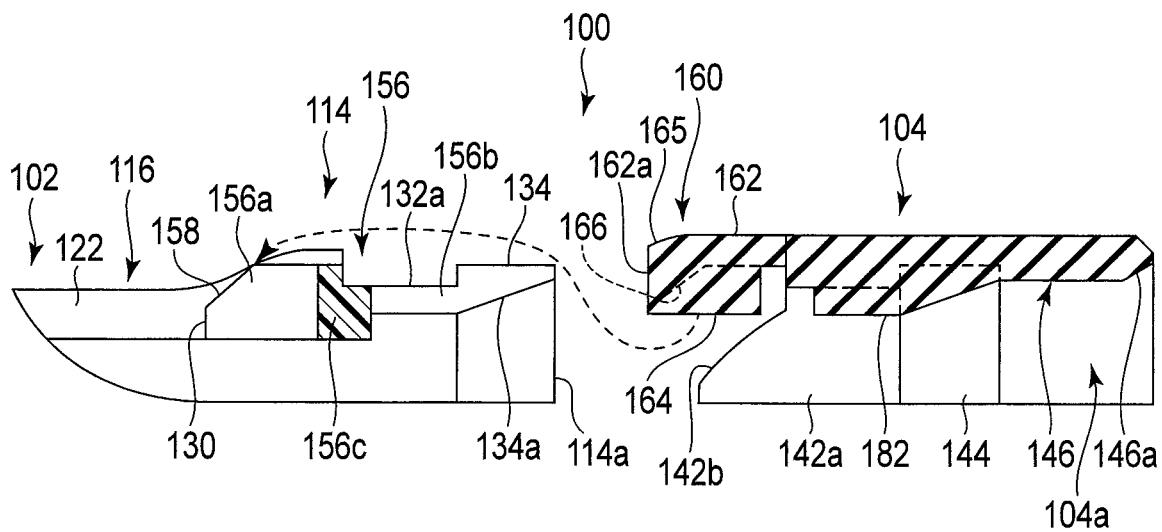
F I G. 4D

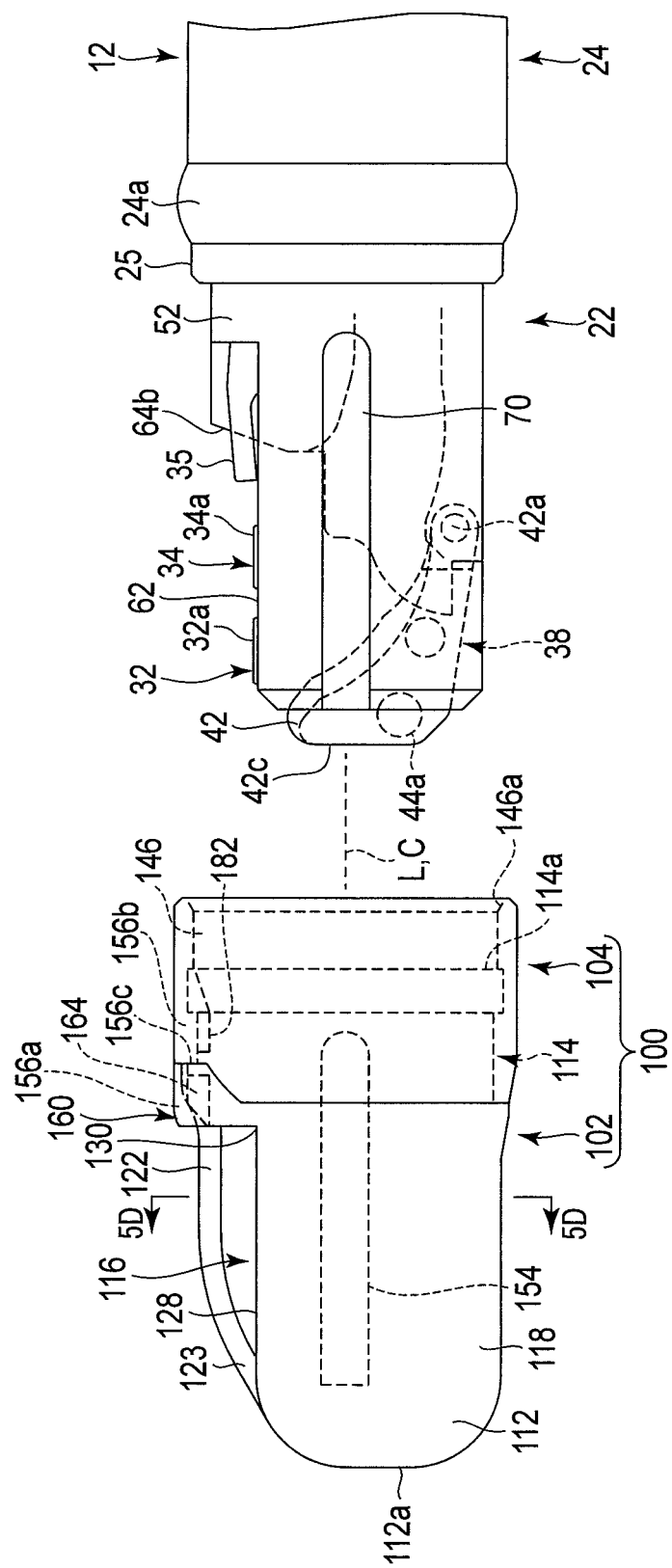
F I G. 5B

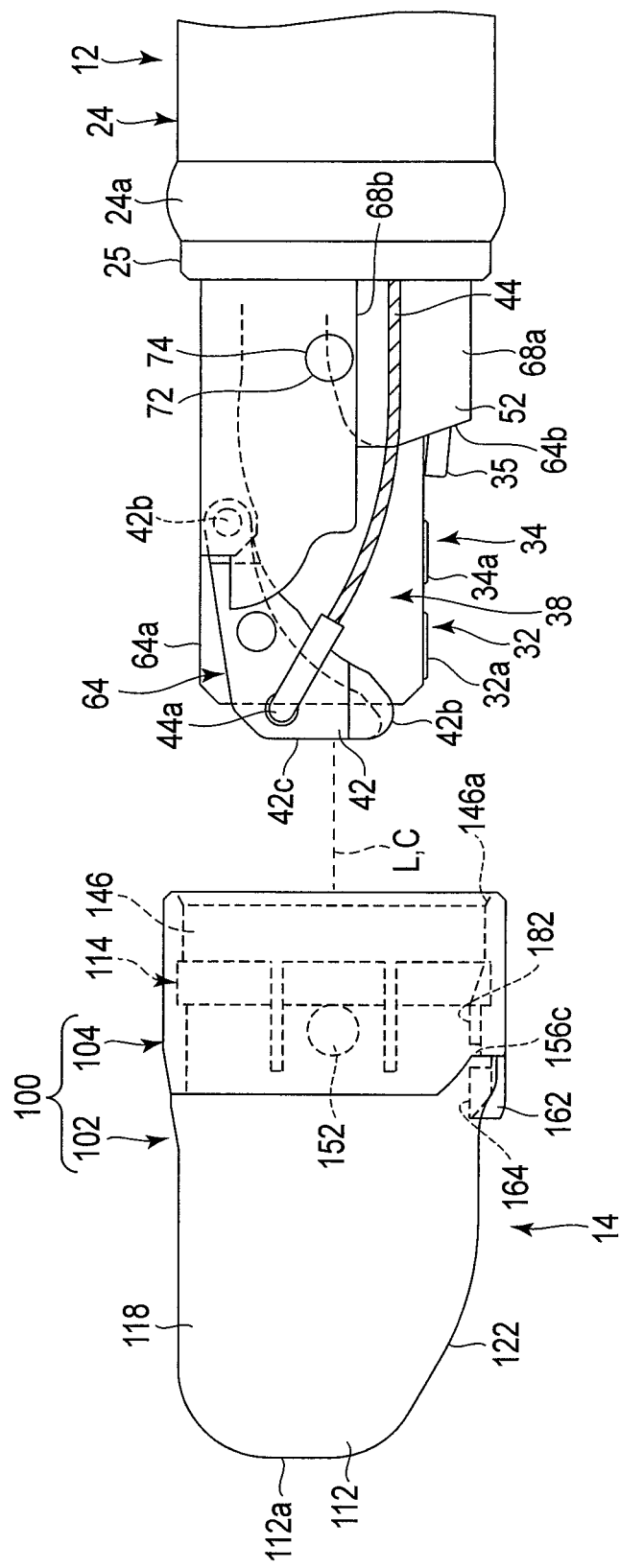
F I G. 5C

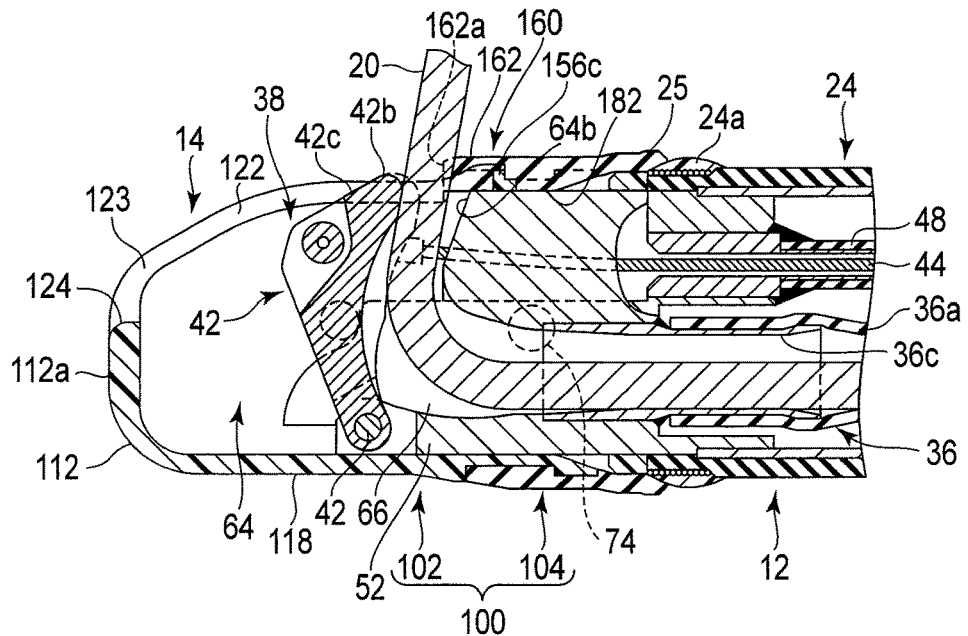
F I G. 6C
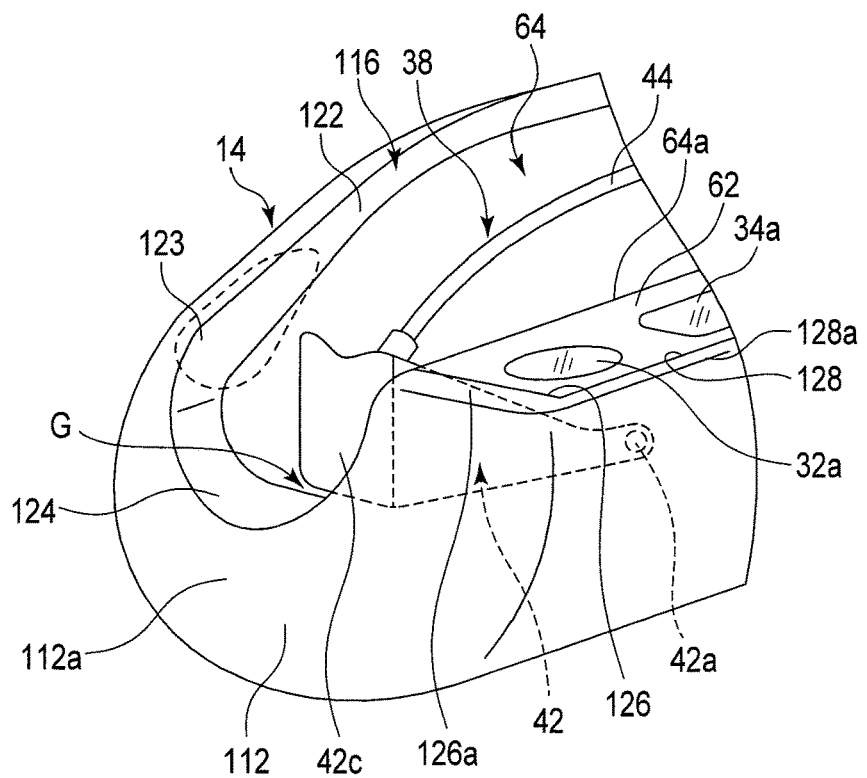
F I G. 7A

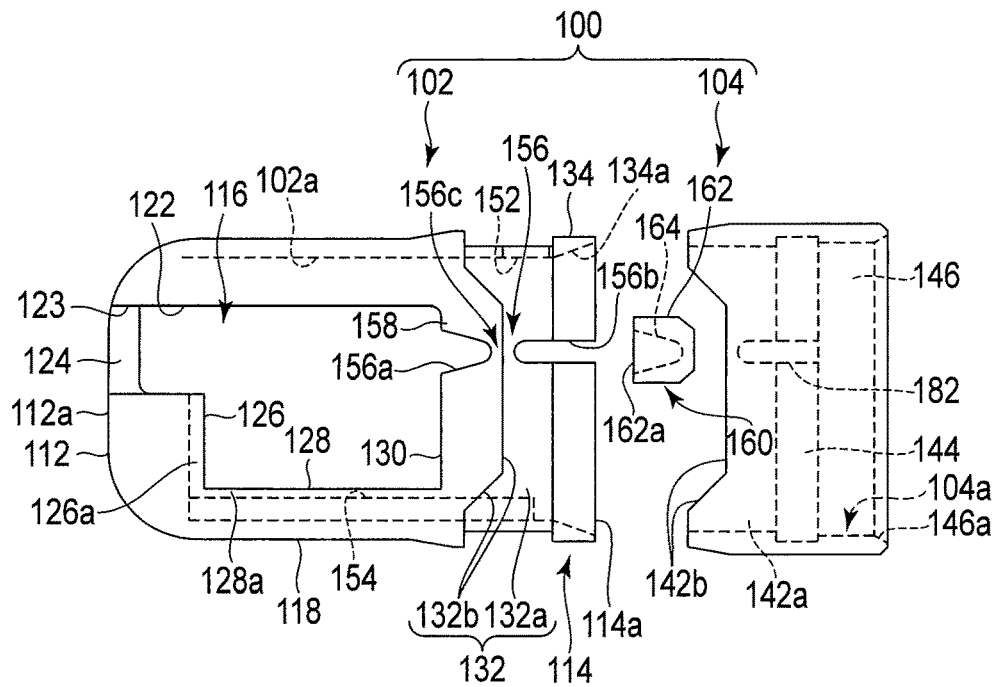
F I G. 12C
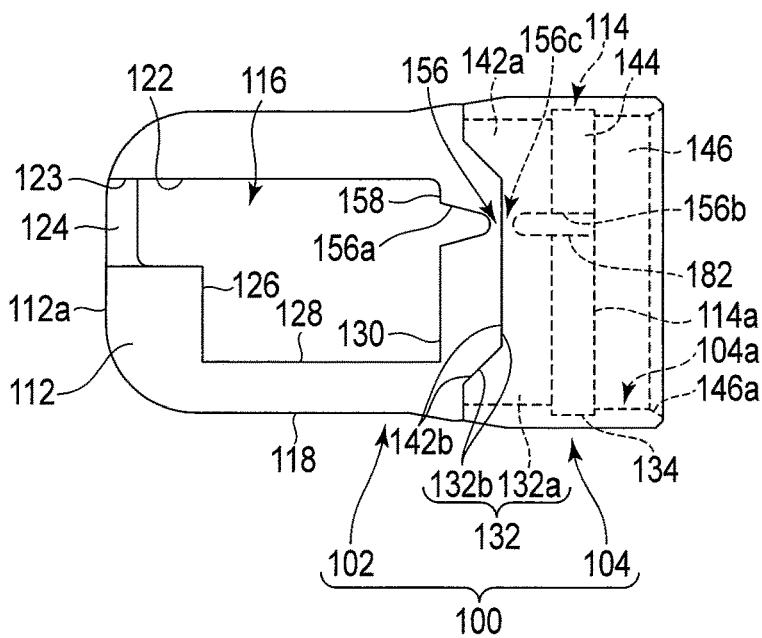
F I G. 12D

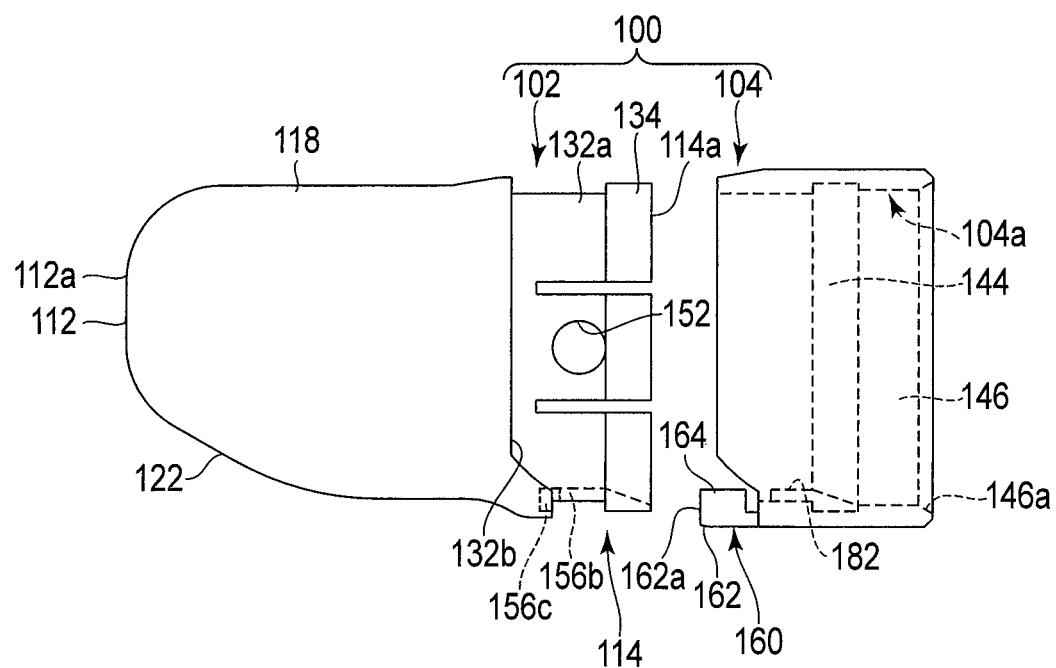
F I G. 19C

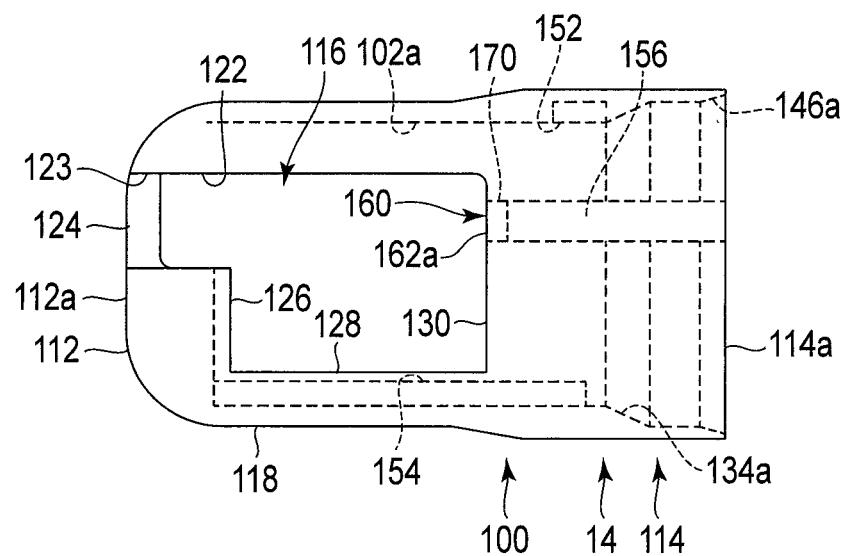
F I G. 25
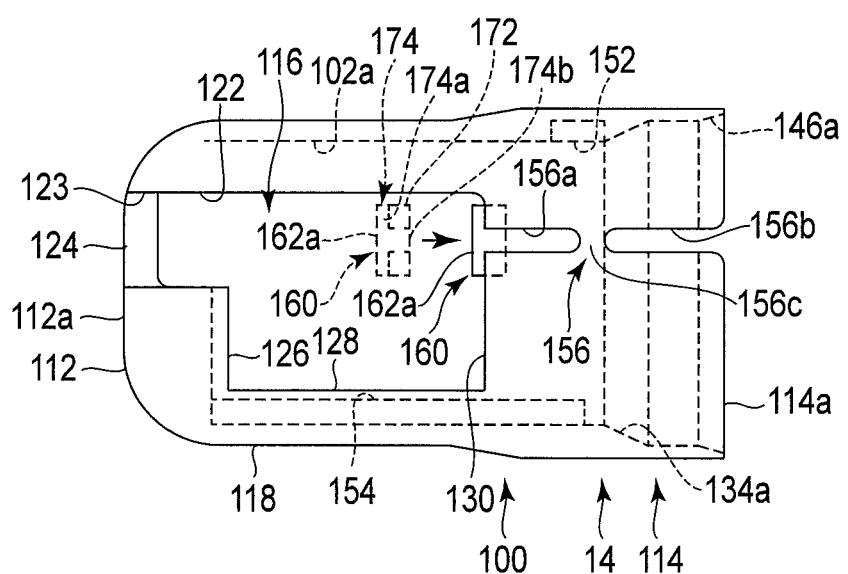
F I G. 26

ENDOSCOPE COVER AND ENDOSCOPE

CROSS-REFERENCE TO RELATED APPLICATIONS

This application is a Continuation Application of PCT Application No. PCT/JP2017/025146, filed Jul. 10, 2017 and based upon and claiming the benefit of priority from prior Japanese Patent Application No. 2016-181383, filed Sep. 16, 2016, the entire contents of all of which are incorporated herein by reference.

BACKGROUND OF THE INVENTION

1. Field of the Invention

This invention relates to an endoscope cover to be attached to the distal framing portion of an insertion section inserted into the body and an endoscope.

2. Description of the Related Art

For example, US 2007/0246506 A1 discloses a cover attached to the distal framing portion of the insertion section of an endoscope. A groove as a fragile portion is formed in this cover. The cover is removed from the distal framing portion by being torn apart and broken along the groove.

BRIEF SUMMARY OF THE INVENTION

According to one aspect of the present invention, an endoscope cover that is to be attached to a distal framing portion of an insertion section of an endoscope, includes a cover main body, a fragile portion, and a buffer portion. The cover main body is to be attached to the distal framing portion from a distal side along a longitudinal axis of the insertion section. The cover main body includes a window and an annular portion. The window opens in a radial direction of the longitudinal axis of the insertion section. The annular portion is provided on a proximal side of the window along the longitudinal axis of the insertion section and surrounding the distal framing portion. The fragile portion is provided at a position on the annular portion. The position is adjacent to the window. The fragile portion forms a region being reduced in mechanical strength relative to other regions of the annular portion. The buffer portion is provided on the cover main body. The buffer portion includes an end portion. The end portion of the buffer portion is located at the same position as a distal end position of the fragile portion along the longitudinal axis or at a position distal to the distal end position of the fragile portion. The end portion of the buffer portion is configured to reduce a force exerted from a distal side of the fragile portion onto the fragile portion along the longitudinal axis.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4C is a view showing an exploded state of the cover attached to the distal framing portion of the endoscope according to the first embodiment, as viewed from the arrow 4C side in FIG. 4A;

FIG. 4D is a schematic sectional view taken along line 4D-4D in FIG. 4A;

FIG. 5B is a view showing a state in which the distal framing portion of the endoscope according to the first embodiment is made to face the proximal side of the cover to be inserted into the cover, as viewed from the arrow 5B side in FIG. 5A;

FIG. 5C is a view showing a state in which the distal framing portion of the endoscope according to the first embodiment is made to face the proximal side of the cover to be inserted into the cover, as viewed from the arrow 5C side in FIG. 5A;

FIG. 6C is a schematic sectional view taken along line 6B-6B in FIG. 6A, showing a state in which a swing table is raised while the cover is attached to the distal framing portion of the endoscope according to the first embodiment and a treatment instrument is inserted in a channel, and the treatment instrument is raised so as to be held on the buffer portion of the cover;

FIG. 7A is a schematic perspective view showing near a distal end portion while the cover is attached to the distal framing portion of the endoscope according to the first embodiment;

FIG. 12C is a schematic view showing a state in which the cover attached to the distal framing portion of the endoscope according to the third modification example of the first embodiment is exploded and the buffer portion is separated from a second cover main body;

FIG. 12D is a schematic view showing the cover attached to the distal framing portion of the endoscope according to the third modification example of the first embodiment in a state in which the second cover main body from which the buffer portion is separated is attached to the first cover main body shown in FIG. 12C;

FIG. 19C is a view showing an exploded state of the cover attached to the distal framing portion of the endoscope according to the seventh modification example of the first embodiment, as viewed from the arrow 19C side in FIG. 19A;

FIG. 25 is a schematic view showing the endoscope cover attached to the distal framing portion of the endoscope according to the first modification example of the second embodiment; and FIG. 26 is a schematic view showing the endoscope cover attached to the distal framing portion of the endoscope according to the second modification example of the second embodiment.

DETAILED DESCRIPTION OF THE INVENTION

Embodiments of the present invention will be described below with reference to the drawings.

The first embodiment is described with reference to FIGS. 1 to 9F.

Figure 1:
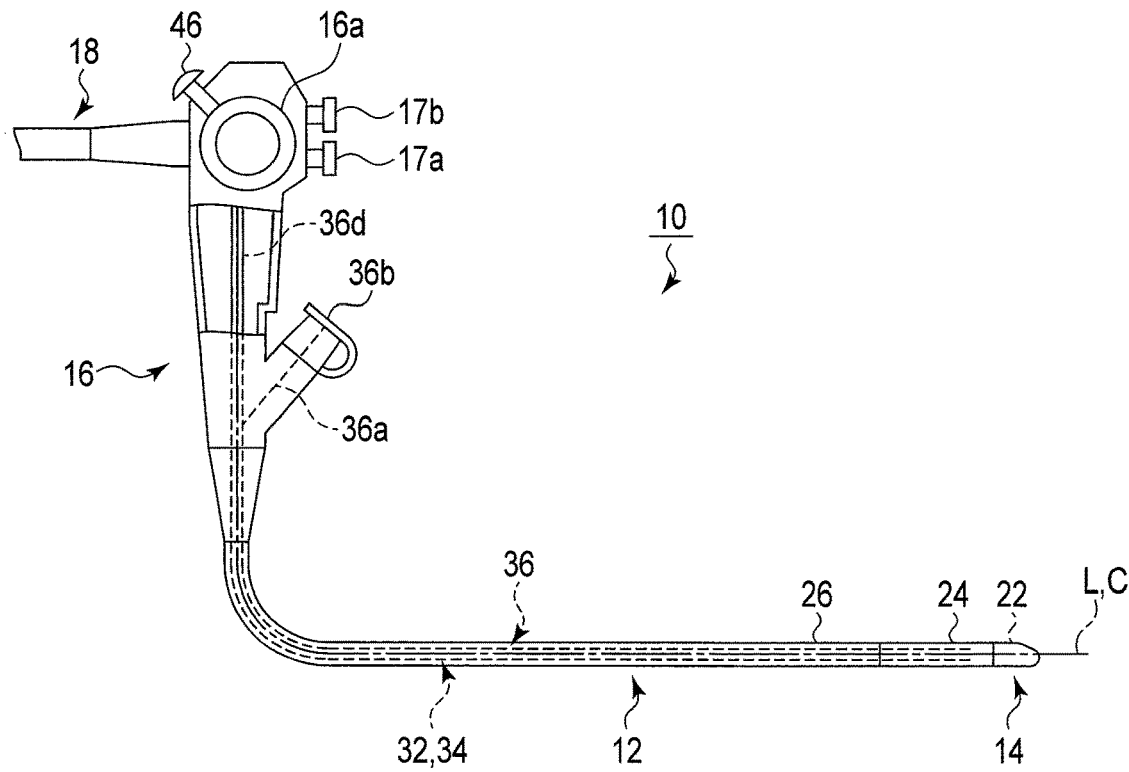
FIG. 1 is a schematic view of an endoscope according to first and second embodiments.

As shown in FIG. 1, an endoscope (insertion device) 10 according to the embodiment includes an insertion section 12 that is configured to be inserted into the body, for example, a lumen, an endoscope cover (hereinafter mainly referred to as a cover) 14 that is configured to be attached to a distal end of the insertion section 12, an operation section 16 that is provided at a proximal end of the insertion section 12 and held by a user, and a universal cord 18 that extends from the operation section 16. The cover 14 is detachably formed with respect to a distal framing portion 22, as will be described in detail later. The cover 14 is preferably formed to be disposable. The cover 14 is easily attachable to the distal framing portion 22 of the insertion section 12 with the shape of the cover 14 maintained, but is configured so as not to be easily removed from the distal framing portion 22 unless at least part of the cover 14 is broken.

The insertion section 12 defines a longitudinal axis L by a distal end and proximal end of the insertion section 12. The insertion section 12 includes, in the order from the distal end to the proximal end, the distal framing portion 22, a bending portion 24, and a tubular portion 26. The tubular portion 26 may be a so-called flexible scope, which has flexibility, or may be a so-called rigid scope, which maintains a straight state and is resistant to bending. The bending portion 24 can be bent in multiple directions such as in two directions or in four directions in response to the operation of a knob 16a of the operation section 16, using a publicly known mechanism.

The endoscope 10 is publicly known and therefore will be briefly discussed. The endoscope 10 includes an illumination optical system 32, an observation optical system 34, and a treatment instrument insertion channel 36. Additionally, the endoscope 10 includes an air/water supply mechanism and a suction mechanism that are not shown. The air/water supply mechanism includes a nozzle 35 and is operated by a button 17a provided in the operation section 16. The suction mechanism communicates with the treatment instrument insertion channel 36, and is operated by a button 17b provided in the operation section 16.

The illumination optical system 32 and the observation optical system 34 are inserted through the distal framing portion 22, the bending portion 24, and the tubular portion 26 of the insertion section 12, the operation section 16, and the distal end portion of the universal cord 18 which corresponding to the operation section 16 in the endoscope 10. The illumination optical system 32 has an illumination window 32a in the distal framing portion 22. The observation optical system 34 has an observation window 34a in the distal framing portion 22.

The channel 36 has a distal end that is open into the distal framing portion 22 of the distal end of the insertion section 12 of the endoscope 10, and has a proximal end that is open in the vicinity of a proximal portion of the tubular portion 26 of the insertion section 12 or into the operation section 16. Here, as shown in FIG. 1, the operation section 16 has an opening (not shown) at the proximal end of the channel 36, and a forceps plug 36b is attachable to and detachable from this opening via a pipe sleeve. The channel 36 has a tube 36a with its distal end fixed to the distal framing portion 22 via a pipe sleeve 36c. Accordingly, the distal framing portion 22 can guide a treatment instrument 20 (see FIGS. 6B and 6C) outside the distal framing portion 22 via the insertion section 12. Furthermore, the tube 36a of the channel 36 includes a suction path 36d that is publicly known, which is branched therefrom inside the operation section 16, for example. The suction path 36d is coupled to the button 17b, and when a press operation of the button 17b is performed, a suctioned object is discharged through a later-described opening 66 at the distal end of the channel 36 via the pipe sleeve 36c, the tube 36a, the suction path 36d, and the universal cord 18.

According to the present embodiment, the distal framing portion 22 is formed as a side-viewing type, in which the direction of observation differs from the direction along the longitudinal axis L of the insertion section 12. For the sake of simplicity, this embodiment will exemplify a case in which the direction of observation of the observation optical system 34 is perpendicular to the longitudinal axis L. In addition, the direction of observation of the observation optical system 34 may be of an oblique-viewing type, which is not perpendicular to the longitudinal axis L. The endoscope 10 includes a swing mechanism 38, which suitably adjusts, at the distal framing portion 22, the orientation of a treatment instrument 20 (see FIG. 6C) or the like passing through the channel 36 so that the treatment target can be observed in the field of view.

The swing mechanism 38 is publicly known and therefore will be briefly discussed. The swing mechanism 38 has a distal end in the distal framing portion 22 of the insertion section 12 of the endoscope 10, and a proximal end in the operation section 16. The swing mechanism 38 includes a swing table (desk table) 42, a wire 44, and a lever 46, in the order from the distal end to the proximal end of the insertion section 12. For example, a known structure using an O-ring (not shown) near the operation section 16 prevents a liquid or gas from entering the tubular portion 26 of the insertion section 12, i.e., between a tube 48 through which the wire 44 is inserted, the bending portion 24, and the tubular portion 26 (see FIG. 1). The swing table 42 is supported on the distal framing portion 22 with a support pin 42a. The support pin 42a is preferably orthogonal to the longitudinal axis L. The distal end of the wire 44 is supported on the swing table 42. The proximal end of the wire 44 is supported on the lever 46. Note that a known mechanism prevents a liquid or gas from entering the insertion section 12 along the wire 44, more specifically, the tubular portion 26 of the insertion section 12. More preferably, this mechanism prevents a liquid or gas from entering the operation section 16 and the tubular portion 26 of the insertion section 12.

As shown in FIGS. 2A to 3C, the distal framing portion 22 has a block-shaped main body 52. The main body 52 may be a cylindrical component of a rigid material such as stainless steel, which includes a flat portion 62, a storage portion (storage space) 64, an opening 66, a wire moving portion (wire moving space) 68, a guide groove (first guide) 70, and a pin fixing portion 72 (to be described later). The main body 52 defines a central axis C (to be described later) common to the cover 14. For the sake of simplicity, it is assumed here that the above-described longitudinal axis L coincides with the central axis C.

Figure 2A:
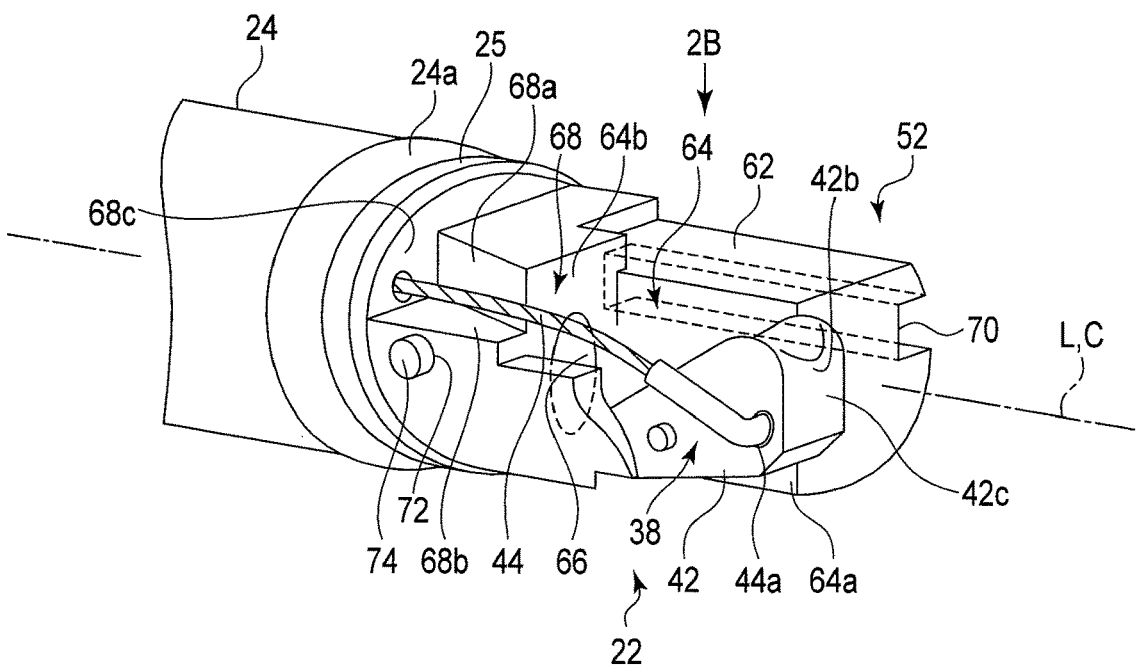
FIG. 2A is a schematic perspective view showing a distal framing portion of the endoscope according to the first embodiment.
Figure 2B:
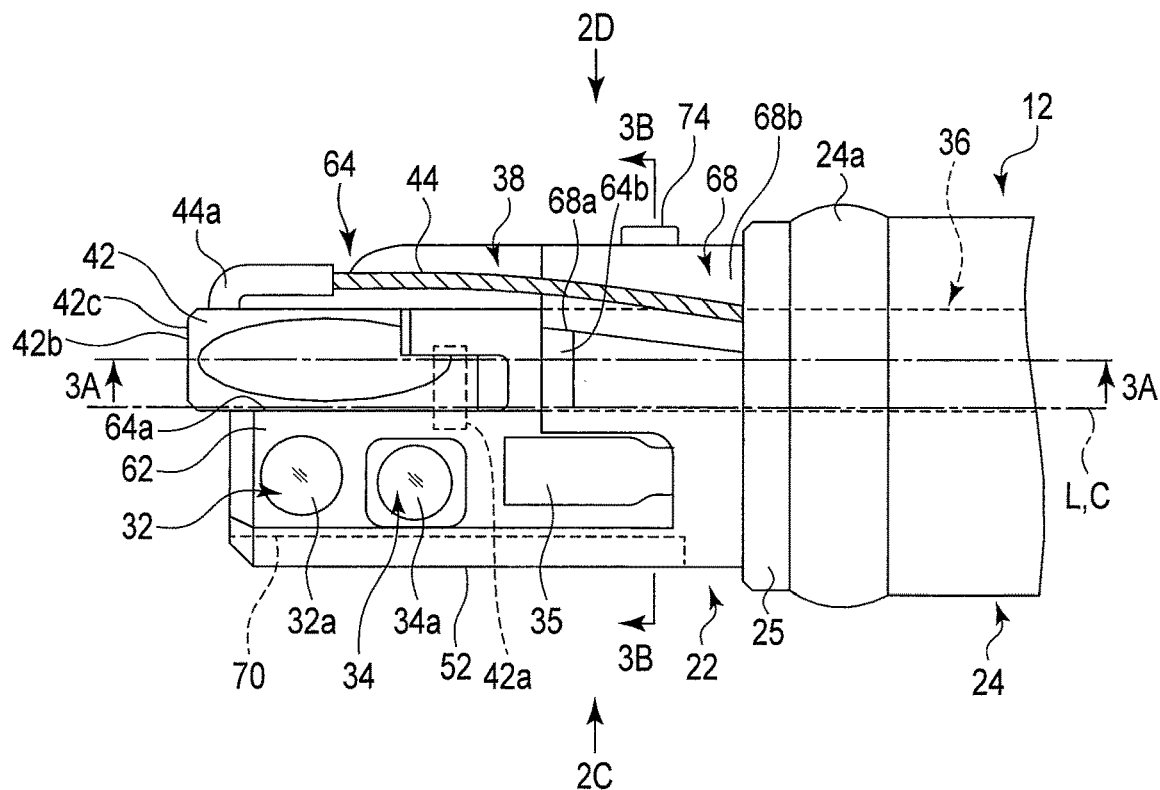
FIG. 2B is a diagram of the distal framing portion of the endoscope according to the first embodiment viewed from an arrow 2B side in FIG. 2A.
Figure 2C:
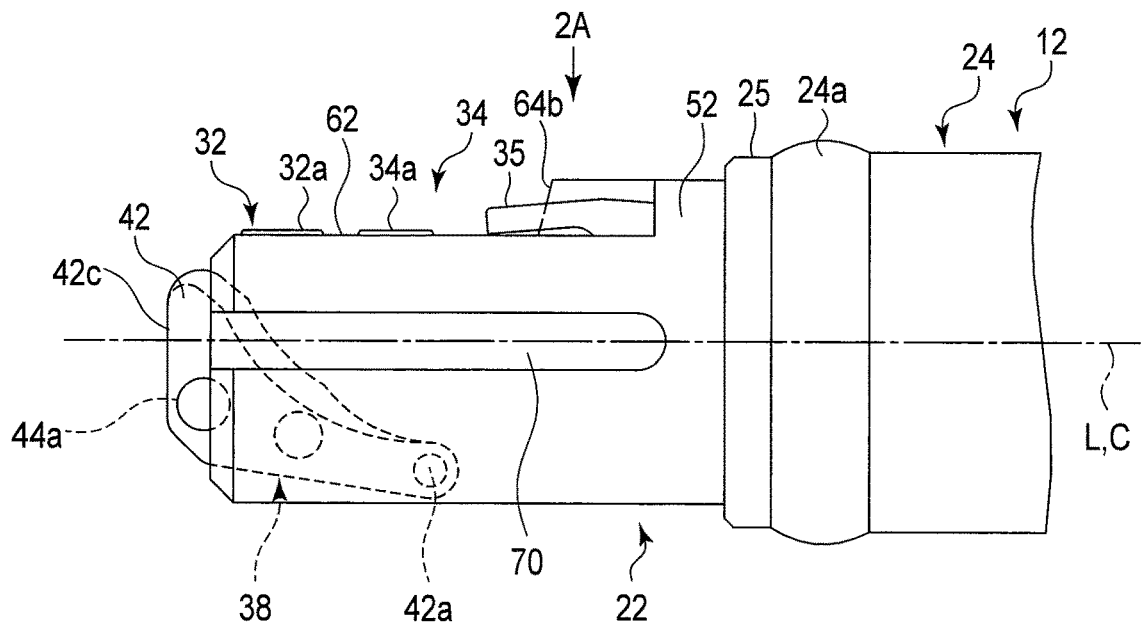
FIG. 2C is a diagram of the distal framing portion of the endoscope according to the first embodiment viewed from an arrow 2C side in FIG. 2B.
Figure 2D:
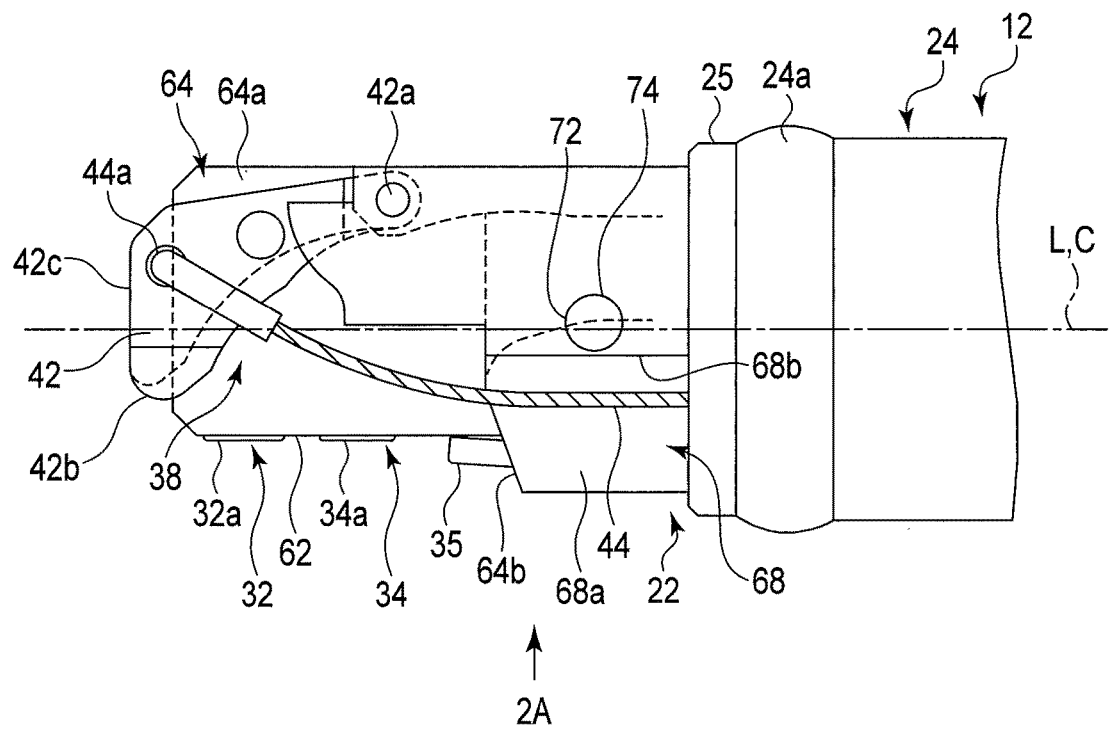
FIG. 2D is a diagram of the distal framing portion of the endoscope according to the first embodiment viewed from an arrow 2D side in FIG. 2B.

As shown in FIGS. 2B to 2D, the main body 52 is provided with the illumination window 32a at the distal end of an illumination optical system 32, the observation window 34a at the distal end of an observation optical system 34, the pipe sleeve 36c (see FIG. 3A) at the distal end of the tube 36a of the channel 36, and the swing table 42 at the distal end of the swing mechanism 38. The distal framing portion 22 is therefore constituted by the main body 52, the illumination window 32a of the illumination optical system 32, the observation window 34a of the observation optical system 34, the pipe sleeve 36c of the distal end portion of the tube 36a of the channel 36, the swing table 42 of the swing mechanism 38, and the wire 44.

Figure 3A:
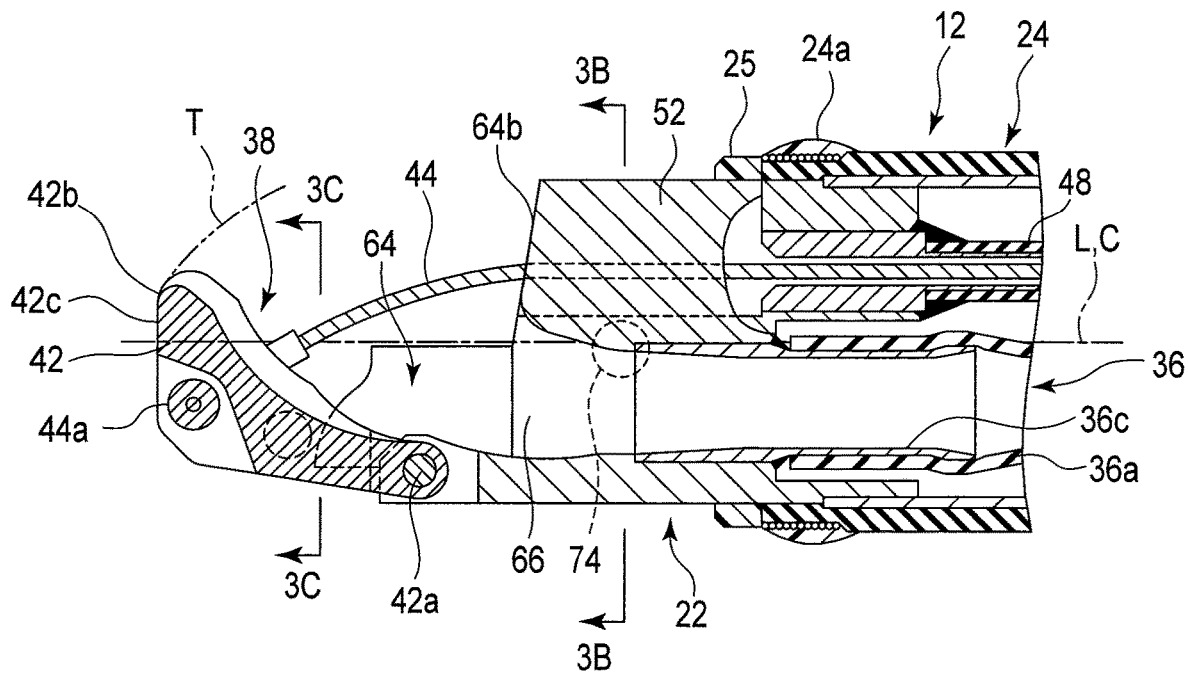
FIG. 3A is a schematic longitudinal sectional view of the distal framing portion of the endoscope according to the first embodiment, taken along the line 3A-3A in FIG. 2B.

The main body 52 includes the flat portion 62 in which the illumination window 32a and the observation window 34a are fixed, a recess portion 64 that accommodates the swing table 42 swingably within a predetermined range, and the opening 66 that communicates with the recess portion 64 to guide a treatment instrument to the swing table 42. As shown in FIG. 3A, the distal end of the tube 36a of the channel 36 is fixed to the opening 66. It is preferable that the distal side of the recess portion 64 along the longitudinal axis L, or in other words, the distal end of the main body 52, is open. A wire moving portion 68 is formed in the recess portion 64 so as to move the wire 44 continuously from the recess portion 64. The wire moving portion 68 is formed on the upper side with respect to the opening 66 in FIG. 3B. The wire moving portion 68 is positioned adjacent to the flat portion 62 in the main body 52. Walls 68a, 68b, and 68c (see FIG. 2A) are formed on the proximal side of the wire moving portion 68 so as to guide the wire 44. The proximal side of the wire moving portion 68, i.e., the walls 68a, 68b, and 68c, preferably form a closed space between themselves and a first cover main body 102.

For the simplicity of explanation, the flat portion 62 of the main body 52 is formed so that a normal N (see FIGS. 3B and 3C) to the flat portion 62 is directed to a direction substantially orthogonal to the longitudinal axis L. In the flat portion 62 of the main body 52, the illumination window 32a is arranged on the distal side, and the observation window 34a is arranged on the proximal side adjacent to the illumination window 32a. The nozzle 35 is provided on the proximal side of the observation window 34a. The nozzle 35 is directed to the observation window 34a and the illumination window 32a. The nozzle 35 is configured to discharge a liquid such as physiological saline toward the observation window 34a and the illumination window 32a, and also to supply air or water and blow off substances adhered on the observation window 34a and the illumination window 32a.

The recess portion 64 is arranged adjacent to the flat portion 62 in a direction orthogonal to the longitudinal axis L. The recess portion 64 forms a space in which the swing table 42 can turn in a predetermined range. The swing table 42 is swingably supported on the main body 52 by the support pin 42a. When the swing table 42 is disposed at a position (lowered position) shown in FIGS. 2A and 3A, a distal face 42c of the swing table 42, including a distal end portion 42b relative to the support pin 42a, protrudes from the distal end of the main body 52 along the longitudinal axis L.

A distal end 44a of the wire 44 of the swing mechanism 38 is supported by the swing table 42. The proximal end (not shown) of the wire 44 of the swing mechanism 38 is supported by the lever 46 of the operation section 16. The length of the wire 44 is adjusted. Accordingly, the swing table 42 is disposed at the position (lowered position) shown in FIGS. 2A to 3A, and 6B with the lever 46 shown in FIG. 1 at a first position (when the lever 46 is raised to the maximum). As the lever 46 is pushed down from the first position, the wire 44 is pulled so that the distal end portion 42b of the swing table 42 that is provided away from the support pin 42a swings along a virtual line T shown in FIG. 3A, with the support pin 42a serving as a pivot. When the lever 46 is pushed down to the maximum, the corresponding position is defined as a second position. At this position, the swing table 42 is disposed at a raised position where the swing table 42 is raised to the maximum shown in FIG. 6C.

As illustrated in FIGS. 2A to 2C, 3B, and 3C, the main body 52 of the distal framing portion 22 includes, on its outer peripheral surface, the guide groove (first restriction portion) 70 as the first guide along the longitudinal axis L. The guide groove 70 is positioned adjacent to the flat portion 62, but is separate from the recess portion 64, or in other words, separate from the wire 44 and the swing table 42 of the swing mechanism 38. It is preferable that the guide groove 70 be continuously formed from the distal end to the proximal side of the main body 52.

The pin fixing portion 72 is formed on the outer peripheral surface of the main body 52 of the distal framing portion 22. It is preferable that the pin fixing portion 72 be formed adjacent to the wire moving portion 68 and on the side substantially opposite to the guide groove 70 across the central axis C of the main body 52 of the distal framing portion 22. A lock pin (lock portion) 74 protruding in the direction orthogonal to the central axis C is fixed to the pin fixing portion 72.

Figure 3B:
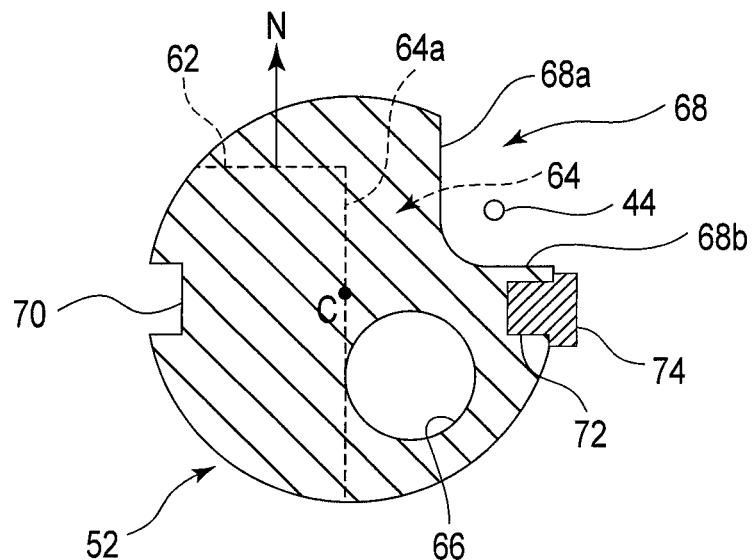
FIG. 3B is a schematic cross sectional view of the distal framing portion of the endoscope according to the first embodiment, taken along the line 3B-3B in FIG. 3A.
Figure 3C:
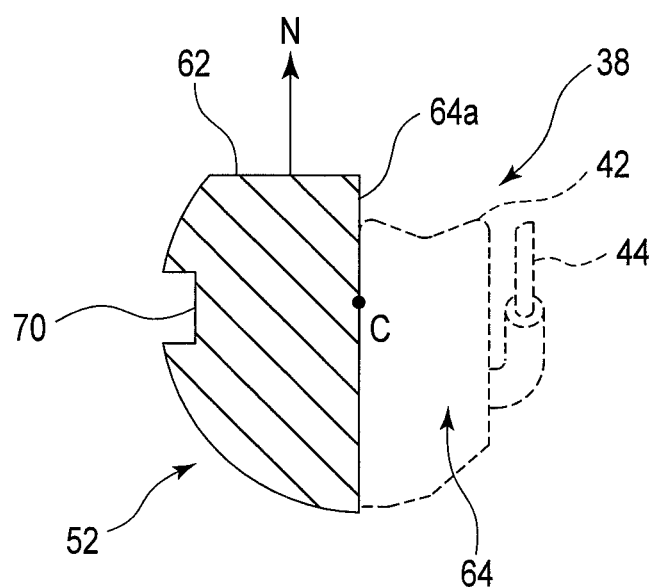
FIG. 3C is a schematic cross sectional view of the distal framing portion of the endoscope according to the first embodiment, taken along the line 3C-3C in FIG. 3A.

With respect to the wall surface 64a of the recess portion 64 shown in FIGS. 3B and 3C as a reference surface, the right side where the swing mechanism 38 is provided is referred to as a first region, and the left side including the flat portion 62 where the illumination optical system 32 and the observation optical system 34 are provided is referred to a second region. The lock pin 74 is positioned in the first region, and the guide groove (first restriction portion) 70 is positioned in the second region, separate from the lock pin 74.

Figure 6A:
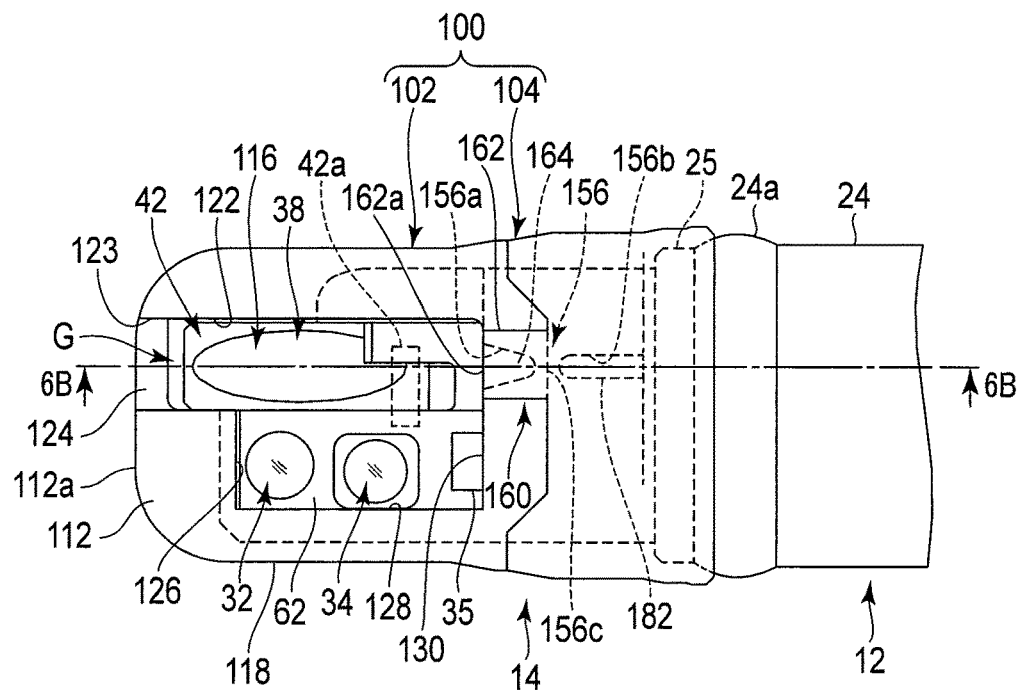
FIG. 6A is a schematic view showing a state in which the cover is attached to the distal framing portion of the endoscope according to the first embodiment.
Figure 6B:
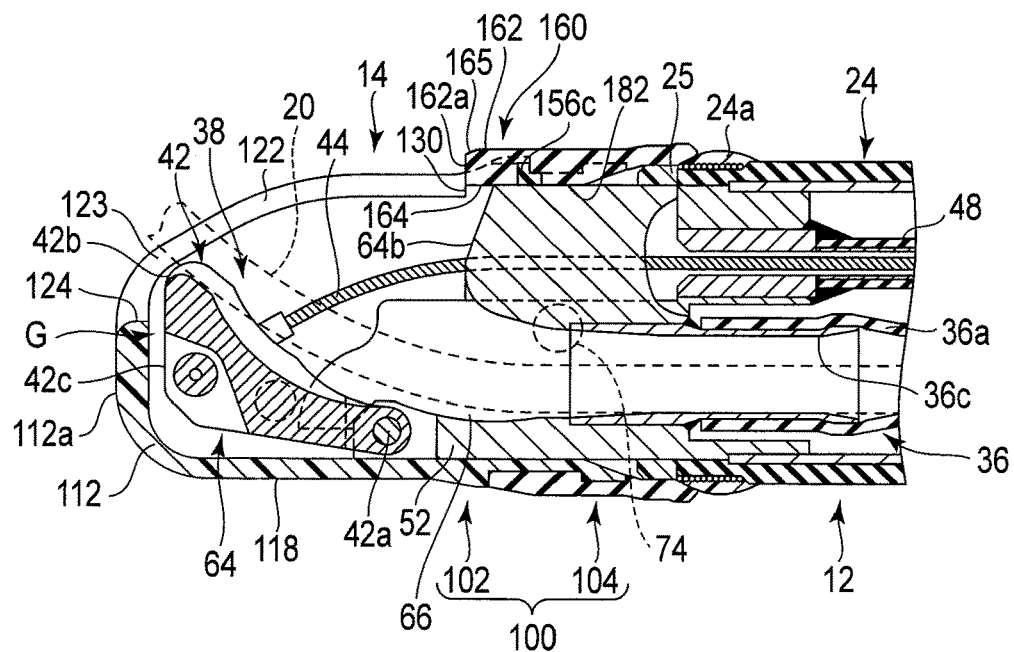
FIG. 6B is a schematic sectional view taken along line 6B-6B in FIG. 6A.

Note that as shown in FIGS. 6B and 6C, when the swing table 42 is raised to the maximum, the block-shaped main body 52 of the distal framing portion 22 forms a wall surface 64b that allows the treatment instrument 20 to be bent through an appropriate angle, preferably 90° or more. In this manner, the recess portion 64 defines the moving range of the swing table 42 together with the wall surfaces 64a and 64b.

The endoscope cover (insertion device cover) 14 configured to be attached to the distal framing portion 22 will be describe next with reference to FIGS. 4A to 5E.

The cover 14 is used while being attached to the distal framing portion 22 of the insertion section 12. The cover 14 according to this embodiment includes a cover main body 100 configured to be attached to the distal framing portion 22 of the insertion section 12 along the longitudinal axis L of the insertion section 12. According to this embodiment, the cover main body 100 includes the first cover main body 102 covering the distal framing portion 22 and a second cover main body (presser ring) 104. The first cover main body 102 and the second cover main body 104 each are preferably formed from a material having electrical insulation properties. The first cover main body 102 is formed from, for example, a resin material (plastic material) in an integrally cylindrical shape (bombshell shape). The second cover main body 104 is formed from a material having higher flexibility than that of the first cover main body 102, for example, a rubber material, in a cylindrical or annular shape. Examples of the plastic material of the first cover main body 102 include polysulfone, polyethylene, and polycarbonate. Examples of the rubber material of the second cover main body 104 include silicone rubber and fluororubber. The inner diameters of the first cover main body 102 and the second cover main body 104, that is, inner peripheral surfaces 102a and 104a are formed in appropriate sizes and shapes based on the size of the distal framing portion 22.

The first cover main body 102 has a closed portion 112 at a distal end of the first cover main body 102, and an annular portion 114 at a proximal end of the first cover main body 102 along the longitudinal axis L. The closed portion 112 is formed into a substantially semispherical surface. The proximal end of the first cover main body 102, or in other words, the proximal end 114a of the annular portion 114, is open. As shown in FIG. 5D, the first cover main body 102 has a rotation peripheral surface 118 which forms an open edge (window) 116 having a substantially C-shaped cross section between the closed portion 112 and the annular portion 114. Accordingly, the annular portion 114 surrounds a portion, of the distal framing portion 22, which is proximal to the open edge 116. The rotation peripheral surface 118 is formed as part of a cylinder. The rotation peripheral surface 118 defines the central axis C of the cover 14 and the distal framing portion 22. The rotation peripheral surface 118 is fitted to a support peripheral surface 214 of a jig 200, which will be described later. The open edge (window) 116 is open in, for example, a direction orthogonal to the longitudinal axis L. That is, the open edge 116 is open in a radial direction of the longitudinal axis L. The open edge 116 is configured to expose the illumination window 32a, the observation window 34a, the nozzle 35, and the swing table 42 of the distal framing portion 22 to the outside.

Figure 5A:
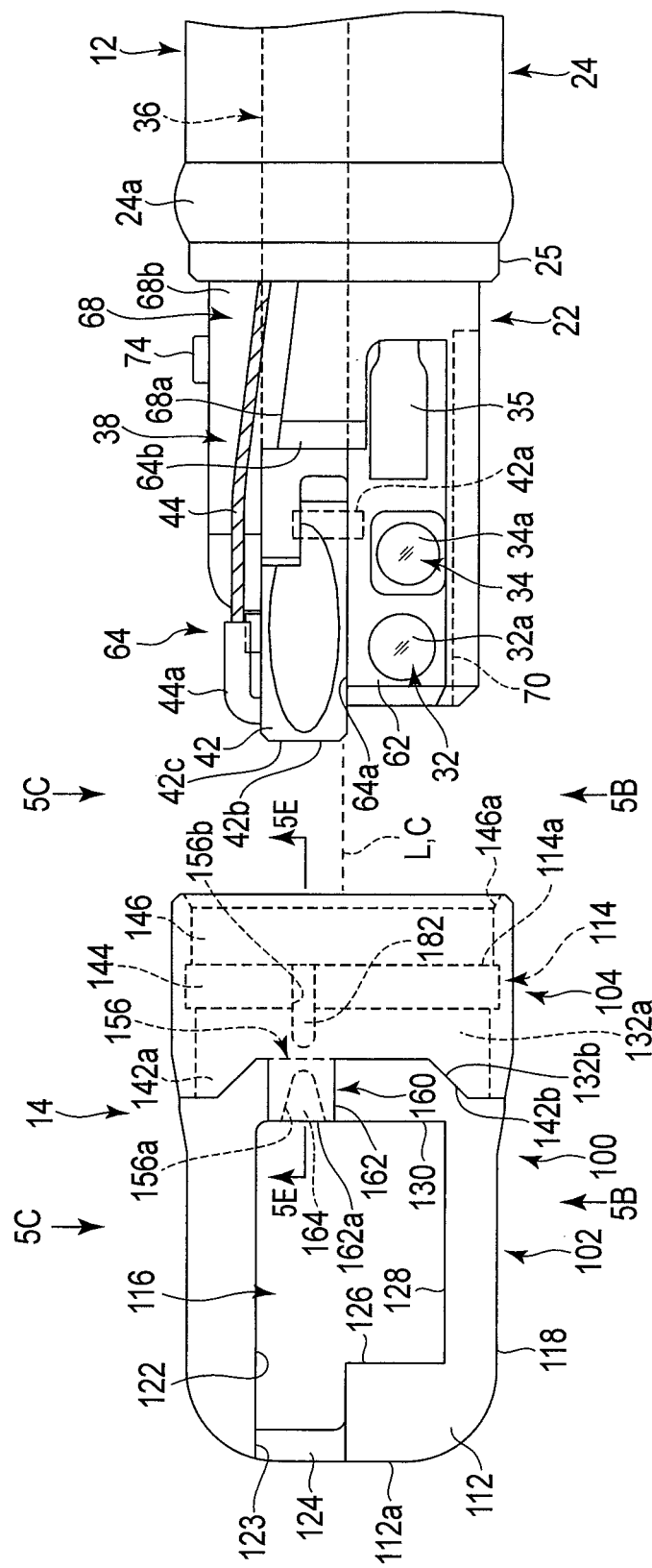
FIG. 5A is a schematic view showing a state in which the distal framing portion of the endoscope according to the first embodiment is made to face the proximal side of the cover to be inserted into the cover.
Figure 5D:
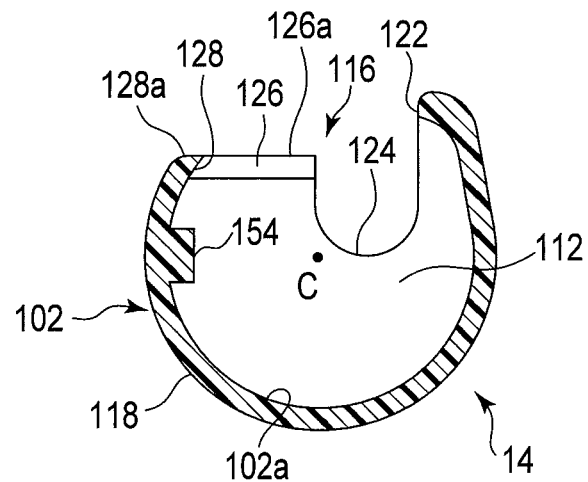
FIG. 5D is a schematic sectional view taken along line 5D-5D in FIG. 5B.

As shown in FIGS. 5A, 5B, and 5D, the open edge 116 includes a right side edge 122 on the right side of the longitudinal axis L when viewed from the proximal side to the distal side, a U-shaped depressed portion 124 continuous with the right side edge 122, a distal side edge 126 continuous with the depressed portion 124, a left side edge 128 provided continuous with the distal side edge 126 on the left side of the longitudinal axis L when viewed from the proximal side to the distal side, and a proximal side edge 130 between the right side edge 122 and the left side edge 128 on the proximal side. The open edge 116 forms a closed ring by the right side edge 122, the depressed portion 124, the distal side edge 126, the left side edge 128, and the proximal side edge 130. It is preferable that the right side edge 122 and the left side edge 128 are parallel, or substantially parallel, to each other, and that the distal side edge 126 and the proximal side edge 130 be parallel, or substantially parallel, to each other.

The right side edge 122 cooperates with the annular portion 114 and the rotation peripheral surface 118 (see FIGS. 5A to 5D) to cover the wire 44 of the swing mechanism 38 in a movable manner. The distal side edge 126 has a distal side covering portion 126a that covers the distal side of the flat portion 62 of the main body 52 with respect to the illumination window 32a. Similarly, the left side edge 128 has a left side covering portion 128a that covers the left side of the flat portion 62 of the main body 52 with respect to the illumination window 32a and the observation window 34a.

The U-shaped depressed portion 124 is formed at the distal end of the right side edge 122 continuously with the right side edge 122. The depressed portion 124 is formed to face a distal end 112a of the closed portion 112. As shown in FIGS. 5B and 5C, the portion in which the depressed portion 124 is formed is tapered toward the distal side along the longitudinal axis L.

Figure 4A:
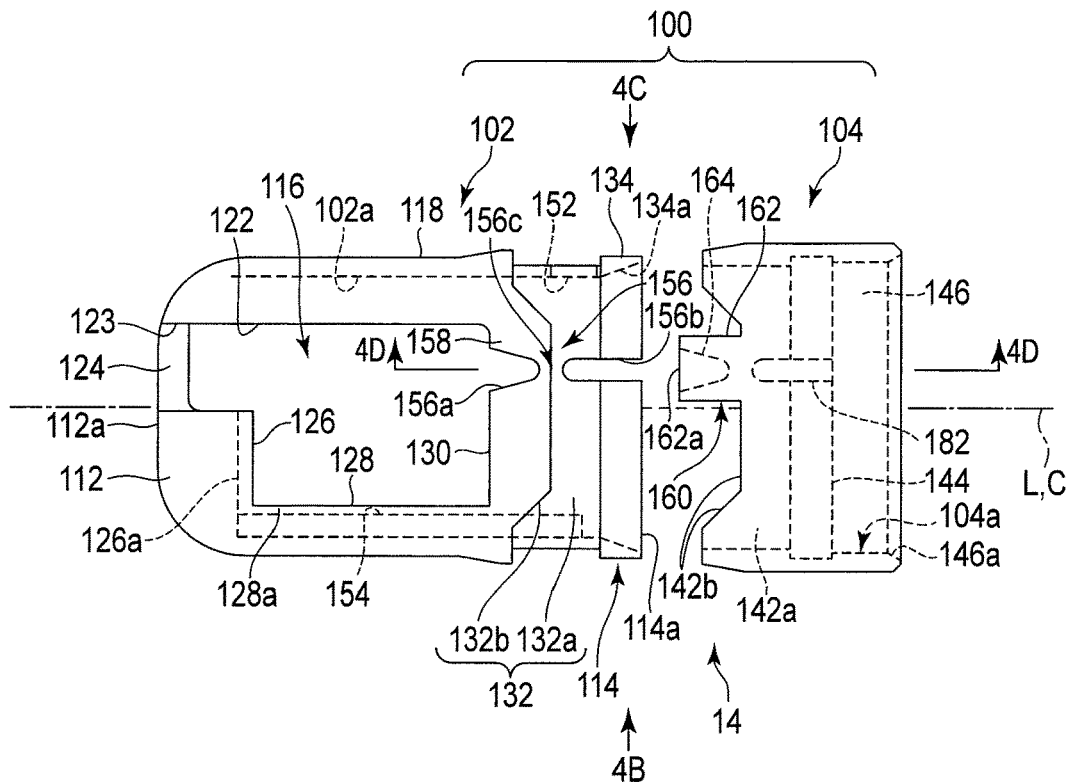
FIG. 4A is a schematic view showing an endoscope cover that is to be attached to the distal framing portion of the endoscope, in a state that the endoscope cover is disassembled, according to the first embodiment.
Figure 4B:
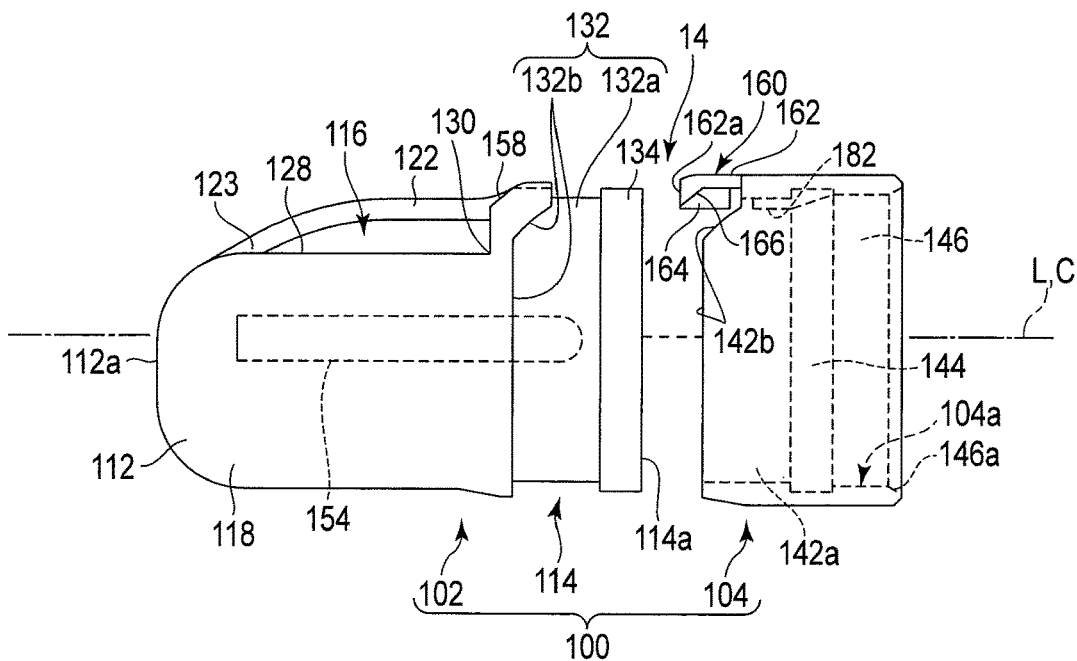
FIG. 4B is a view showing the cover attached to the distal framing portion of the endoscope according to the first embodiment, as viewed from the arrow 4B side in FIG. 4A.

As shown in FIGS. 4A to 4C, the annular portion 114 includes, on its outer peripheral surface, an attachment portion 132 to which the second cover main body 104 is fitted. The attachment portion 132 is formed circumferentially on the proximal side of the proximal side edge 130 of the open edge 116 along the longitudinal axis L, at a position away from the proximal side edge 130. The attachment portion 132 includes an annular depressed portion 132a that prevents the second cover main body 104 from moving along the longitudinal axis L with respect to the first cover main body 102, and an attachment depressed portion 132b that prevents the second cover main body 104 from moving around the longitudinal axis L. The annular depressed portion 132a and the attachment depressed portion 132b are formed integrally and continuously with each other. The annular portion 114 has an annular flange portion 134 that is formed on the proximal end of the attachment portion 132 to protrude from the annular depressed portion 132a outwardly in a radial direction of the longitudinal axis L. Formed on the inner periphery of the flange portion 134 is a skirt portion 134a, which is configured to be thinner toward the proximal side along the longitudinal axis L. The inner diameter of the skirt portion 134a increases toward the proximal side. It is preferable that the skirt portion 134a be tapered.

It is preferable that the inner diameter of the inner peripheral surface 102a of the first cover main body 102 stay constant from the vicinity of the distal ends of the right side edge 122 and the left side edge 128 of the open edge 116 to the distal end of the skirt portion 134a of the flange portion 134.

The second cover main body 104 includes an annular protruding portion 142a formed in the inner peripheral surface 104a of the second cover main body 104 to be to the annular depressed portion 132a, and an attachment protruding portion 142b which is to be attached to the attachment depressed portion 132b. The second cover main body 104 includes an annular attachment depressed portion 144 formed in the inner peripheral surface 104a of the second cover main body 104, to which the flange portion 134 is to be attached on the proximal side of the annular protruding portion 142a. In this manner, the second cover main body 104 is fitted to the annular portion 114 of the first cover main body 102, as shown in FIGS. 5A to 5C and 6. The second cover main body 104 further includes an attachment portion 146 formed on the inner peripheral surface 104a on the proximal side of the attachment depressed portion 144 to be attached to the thread wound portion 24a at the distal end portion of the bending portion 24 and the insulation member 25 at the front side of the thread wound portion 24a. A skirt portion 146a that is configured to be thinner toward the proximal side along the longitudinal axis L is formed on the inner periphery of the proximal end of the attachment portion 146. The inner diameter of the skirt portion 146a increases toward the proximal side.

As shown in FIGS. 4A, 4C, and 5C, a lock depressed portion (lock portion) 152 is formed in the inner peripheral surface 102a of the annular portion 114 at the proximal end of the first cover main body 102 to be engaged with the lock pin 74 of the distal framing portion 22. That is, the lock depressed portion (lock portion) 152 engages the first cover main body 102 with the distal framing portion 22. The lock depressed portion 152 may be formed in a manner that the inner peripheral surface 102a of the first cover main body 102 communicates with the outer peripheral surface, or may be formed simply to be depressed in the inner peripheral surface 102a of the first cover main body 102. It is preferable that the lock depressed portion 152 be formed in the annular depressed portion 132a.

A guide protruding portion (second guide) 154 is formed in the inner peripheral surface 102a of the first cover main body 102 to be movable along the guide groove 70.

That is, the guide protruding portion 154 protrudes inwardly from the inner peripheral surface 102a of the first cover main body 102 in the radial direction. It is preferable here that the guide protruding portion 154 be formed to extend from the vicinity of the distal end to the vicinity of the proximal end of the inner peripheral surface 102a of the first cover main body 102. The guide protruding portion 154 may be formed into a suitable shape, and may be formed to have substantially a rectangular cross section, as shown in FIG. 5D. Otherwise, although not shown, more than one guide protruding portion 154 may be formed and spaced apart at suitable intervals.

Figures 17A, 17B:
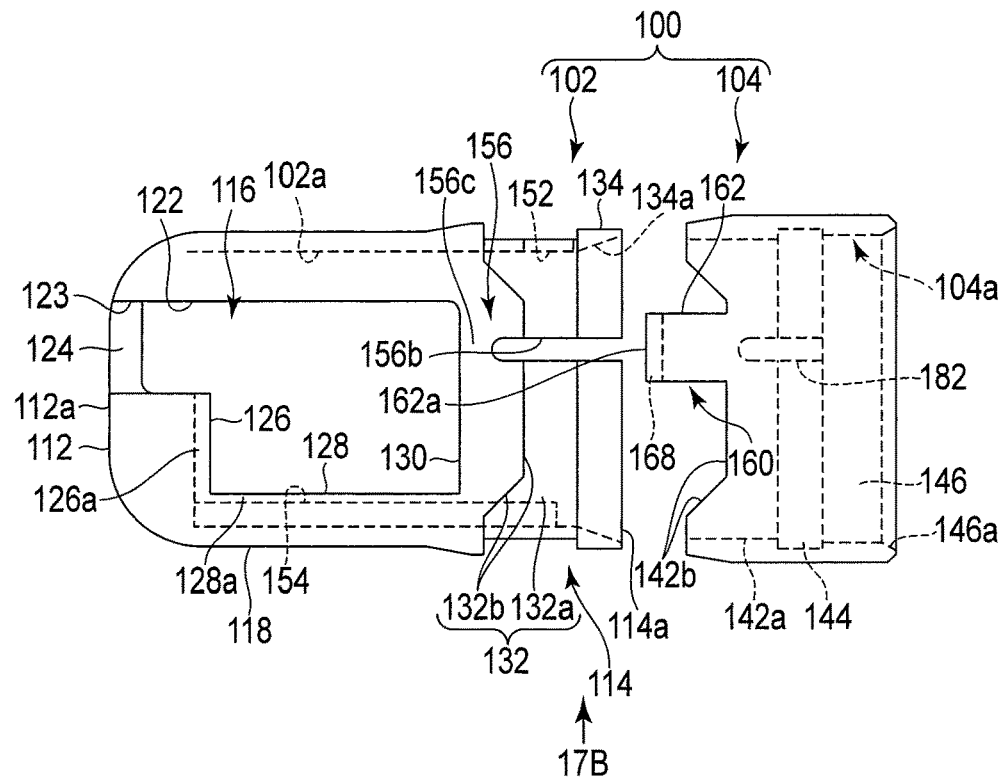
FIG. 17A is a schematic view showing an exploded state of the endoscope cover attached to the distal framing portion of the endoscope according to the sixth modification example of the first embodiment.
FIG. 17B is a view showing an exploded state of the cover attached to the distal framing portion of the endoscope according to the sixth modification example of the first embodiment, as viewed from the arrow 17B side in FIG. 17A.
Figure 18A:
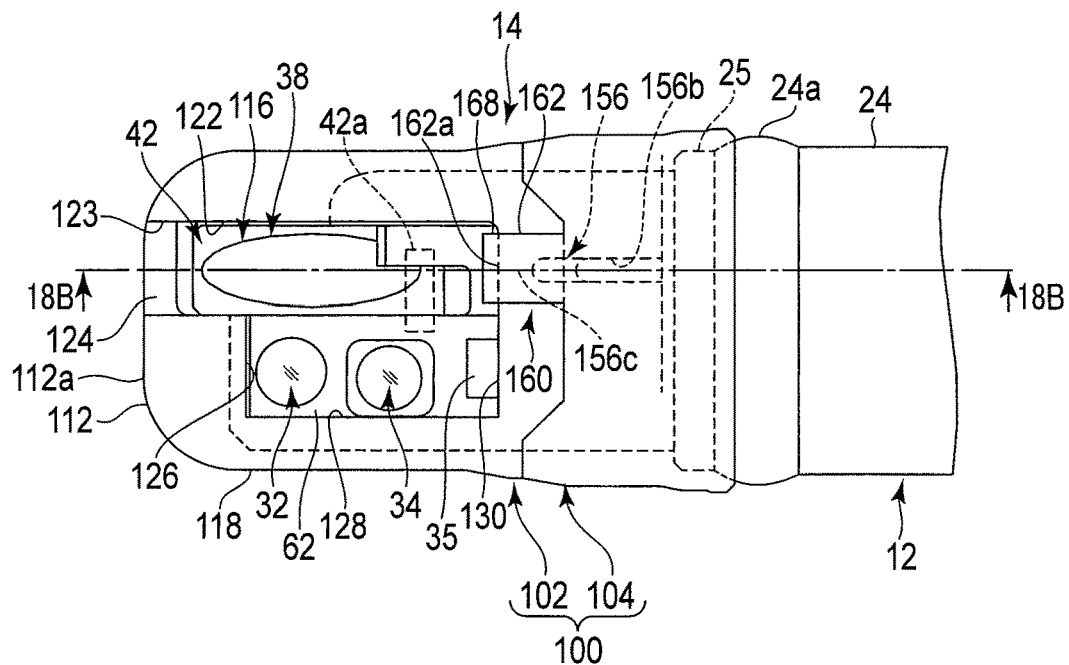
FIG. 18A is a schematic view showing a state in which the cover is attached to the distal framing portion of the endoscope according to the sixth modification example of the first embodiment.
Figure 18B:
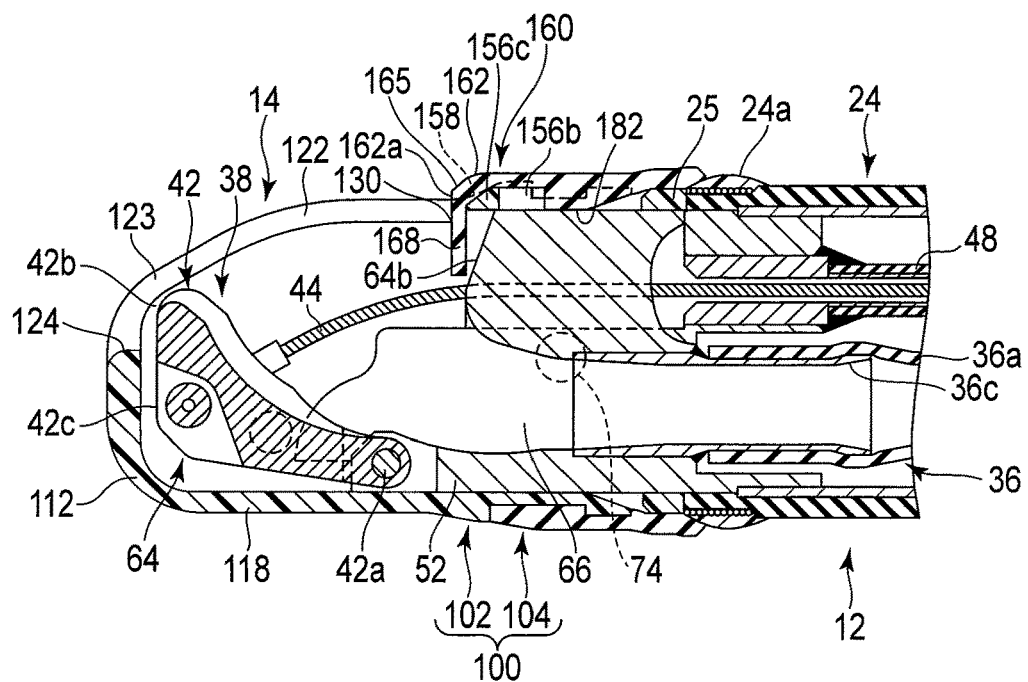
FIG. 18B is a schematic sectional view taken along line 18B-18B in FIG. 18A.
Figure 19A:
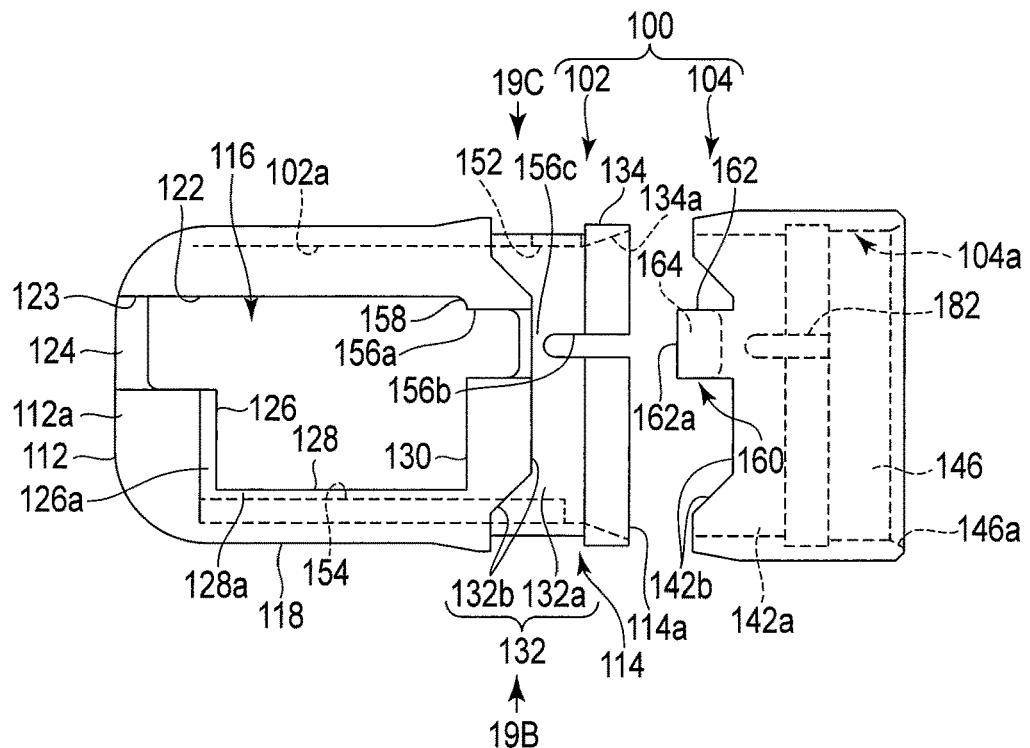
FIG. 19A is a schematic view showing an exploded state of the endoscope cover attached to the distal framing portion of the endoscope according to the seventh modification example of the first embodiment.
Figure 19B:
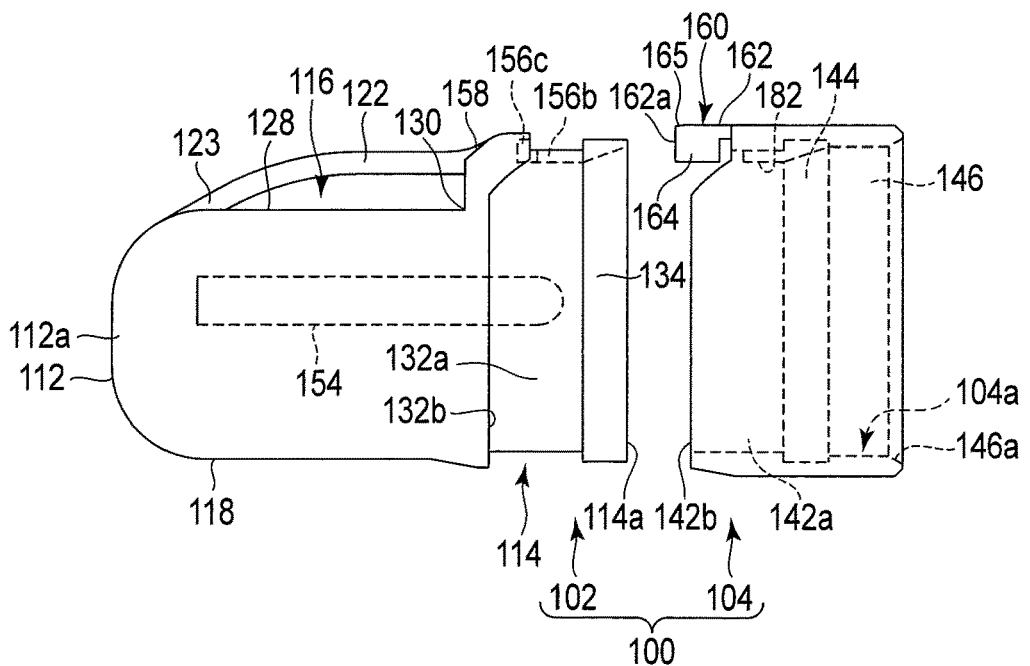
FIG. 19B is a view showing an exploded state of the cover attached to the distal framing portion of the endoscope according to the seventh modification example of the first embodiment, as viewed from the arrow 19B in FIG. 19A.
Figure 20A:
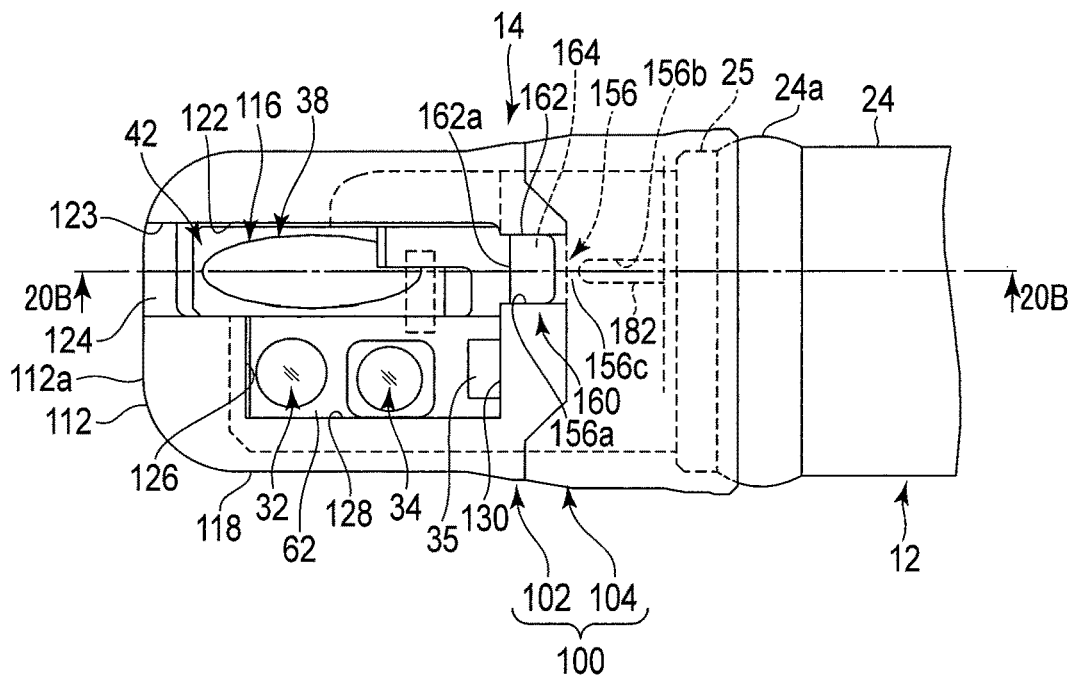
FIG. 20A is a schematic view showing a state in which the cover is attached to the distal framing portion of the endoscope according to the seventh modification example of the first embodiment.
Figure 20B:
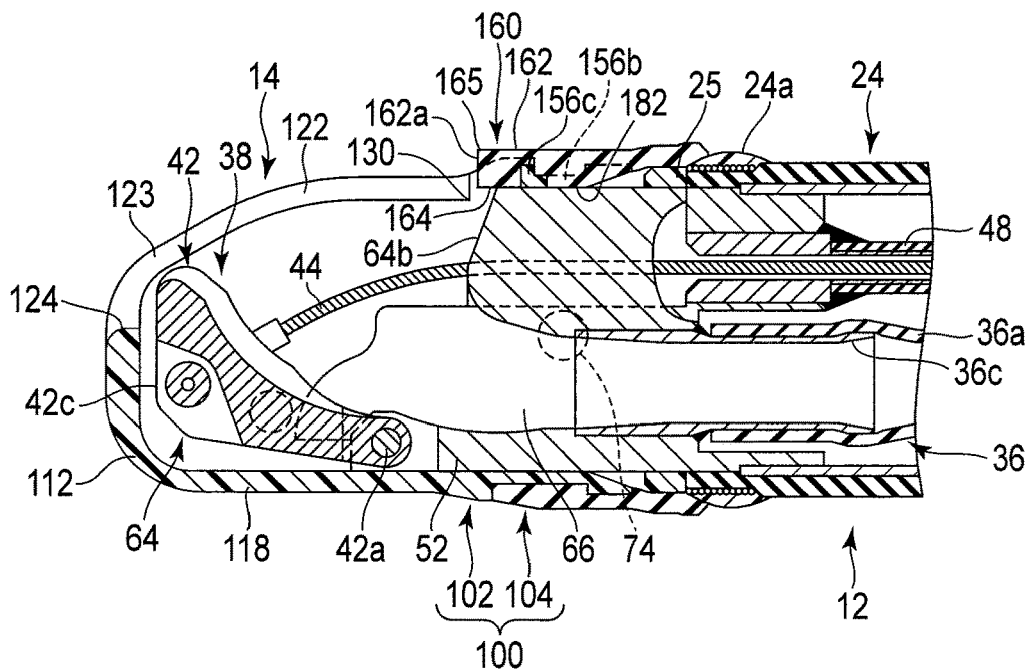
FIG. 20B is a schematic sectional view taken along line 20B-20B in FIG. 20A.
Figure 21A:
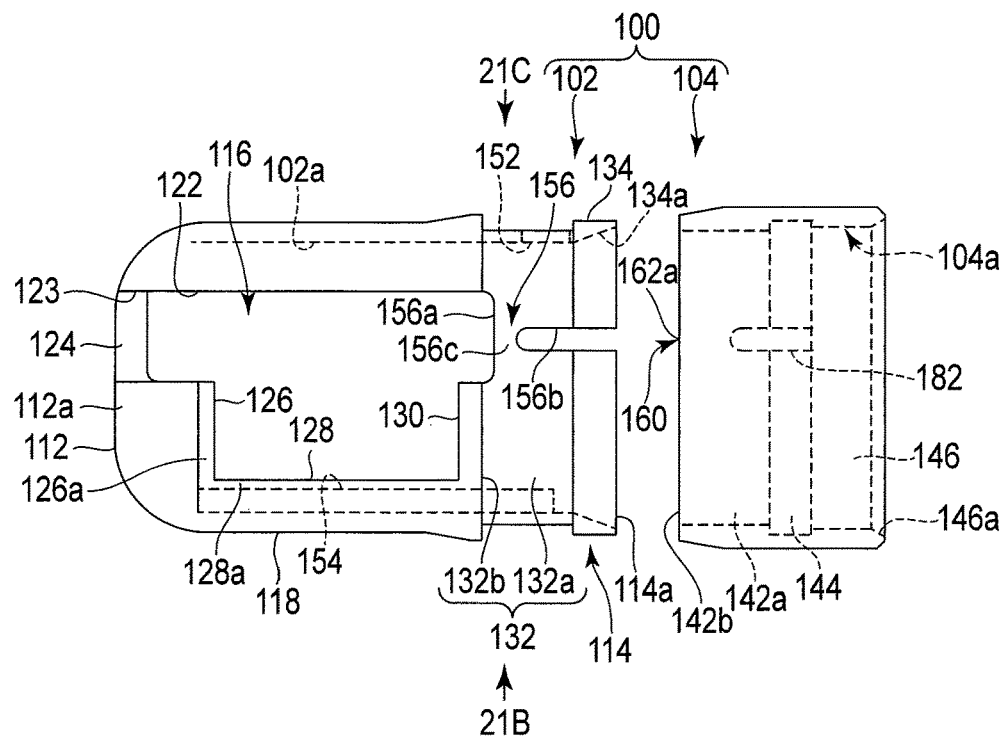
FIG. 21A is a schematic view showing an exploded state of the endoscope cover attached to the distal framing portion of the endoscope according to the eighth modification example of the first embodiment.
Figure 21B:
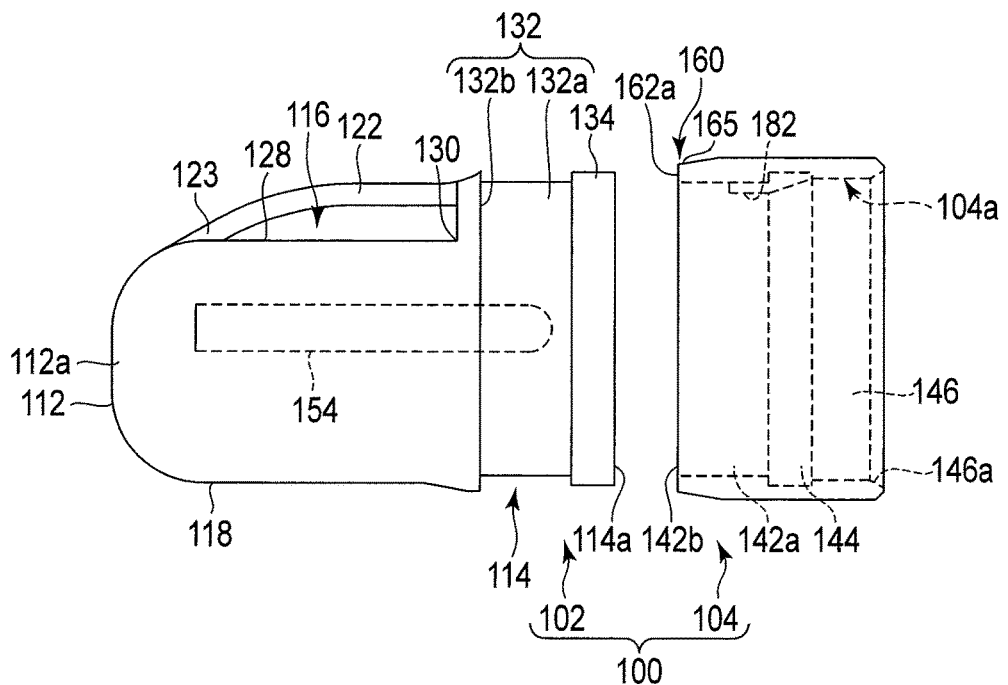
FIG. 21B is a schematic view showing an exploded state of the cover attached to the distal framing portion of the endoscope according to the eighth modification example of the first embodiment, as viewed from the arrow 21B side in FIG. 21A.
Figure 21C:
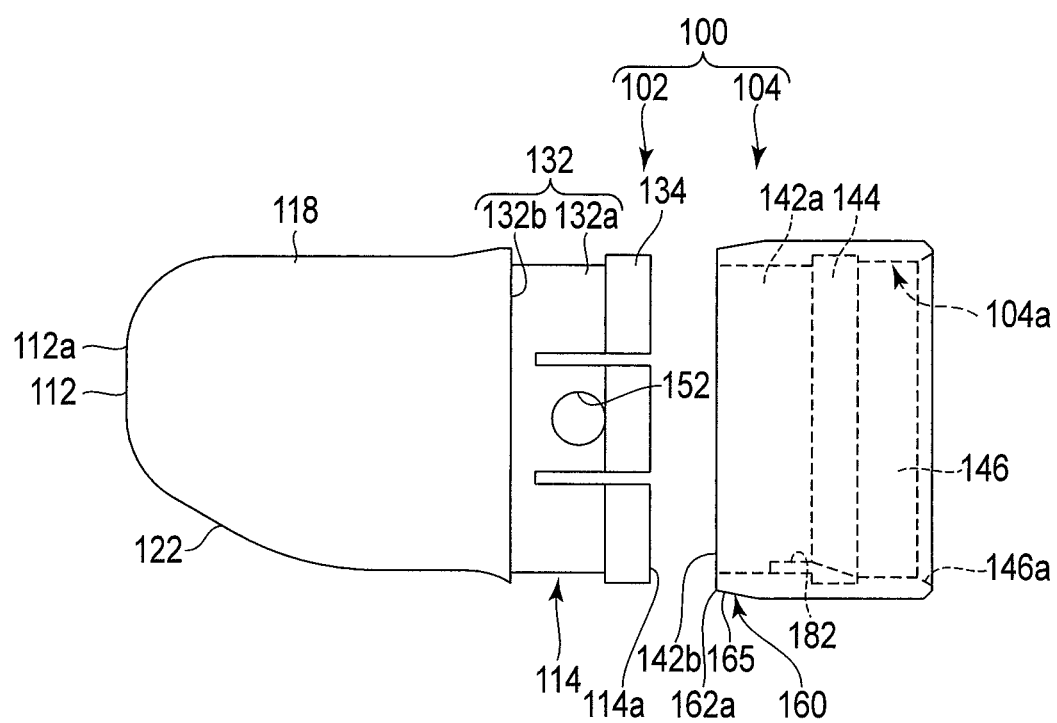
FIG. 21C is a schematic view showing an exploded state of the cover attached to the distal framing portion of the endoscope according to the eighth modification example of the first embodiment, as viewed from the arrow 21C side in FIG. 21A.

As shown in FIGS. 4A and 4B, a fragile portion 156 is formed between the proximal side edge 130 of the open edge 116 of the first cover main body 102 and the proximal end 114a of the annular portion 114. The fragile portion 156 is formed at a position in the first region with reference to the wall surface 64a of the recess portion 64 on the proximal side along the longitudinal axis L while the cover 14 is attached to the distal framing portion 22. The fragile portion 156 is provided at a position on the annular portion 114, in particular, a position adjacent to the open edge 116. In this case, "a position adjacent to the open edge 116" includes both a state in which the fragile portion 156 is continuous with the open edge 116 and a state in which the fragile portion 156 is not continuous as in the case shown in FIG. 17A (described later), as described in this embodiment.

The fragile portion 156 forms a region that is made fragile by being reduced in mechanical strength relative to other regions adjacent to the fragile portion 156 (other regions of the annular portion 114). Accordingly, the fragile portion 156 has low proof stress against a force in a predetermined direction with respect to the other regions, and hence is susceptible to breakage. The fragile portion 156 is a region inducing breakage (breakage inducing region) between the proximal side edge 130 or the right side edge 122 of the open edge (window) 116 when the cover main body 100 is removed from the distal framing portion 22. The region formed from the fragile portion 156 is broken when the cover 14 is removed from the distal framing portion 22.

In this case, the fragile portion 156 is provided on the annular portion 114 of the first cover main body 102, and is formed so as to break the annular portion 114 by exerting a stress on the annular portion 114 in a predetermined direction. The fragile portion 156 has low mechanical strength with respect to other regions of the annular portion 114. The fragile portion (breakage inducing region) 156 has slits (breakage inducting portions) 156a and 156b and a coupling portion 156c. One slit (notched portion) 156a is formed continuously with the proximal side edge 130 of the open edge 116. The slit 156a causes breakage between the open edge 116 of the first cover main body 102 of the cover main body 100 and the proximal end of the cover main body 100 (the proximal end 114a of the annular portion 114 in this case), i.e., part of the annular portion 114, and induces breakage in a predetermined region between the open edge 116 and the proximal end 114a of the cover main body 100 along the longitudinal axis L, when the cover main body 100 is removed from the distal framing portion 22.

An inclined plane 158 is formed near the distal end of the slit 156a of the fragile portion 156, i.e., at a position near the proximal side edge 130 of the open edge 116. The inclined plane 158 is directed to both outward in the radial direction relative to the longitudinal axis L and the distal side along the longitudinal axis L.

The other slit (the other notched portion) 156b is formed continuously with the proximal end 114a of the annular portion 114. The other slit 156b induces breakage in a predetermined region when part of the annular portion 114 of the first cover main body 102 of the cover main body 100 is broken when the cover main body 100 is removed from the distal framing portion 22. In this case, the slits 156a and 156b are formed adjacent to each other along the longitudinal axis L. The slits 156a and 156b do not communicate with each other, and the coupling portion 156c is formed. For this reason, the annular depressed portion 132a of the annular portion 114 is formed annularly around the longitudinal axis L.

The lock depressed portion 152 is formed at a position approximately 90° away from the coupling portion 156c of the fragile portion 156 in the peripheral direction with respect to the longitudinal axis L. The guide protruding portion 154 is formed at a position approximately 90° away from the coupling portion 156c on the side opposite to the lock depressed portion 152 in the peripheral direction of the longitudinal axis L. It is preferable that the fragile portion 156 be positioned approximately 90° away from each of the guide protruding portion 154 and the lock depressed portion 152 in the peripheral direction of the central axis C. That is, the position of the guide protruding portion 154 differs from the position of the lock depressed portion 152 in the peripheral direction with respect to the longitudinal axis L. It is further preferable that the fragile portion 156 is positioned more than 90° away from the guide protruding portion 154 in the peripheral direction, and that the distance between the fragile portion 156 and the lock depressed portion 152 is shorter than the distance between the guide protruding portion 154 and the fragile portion 156.

Figure 5E:
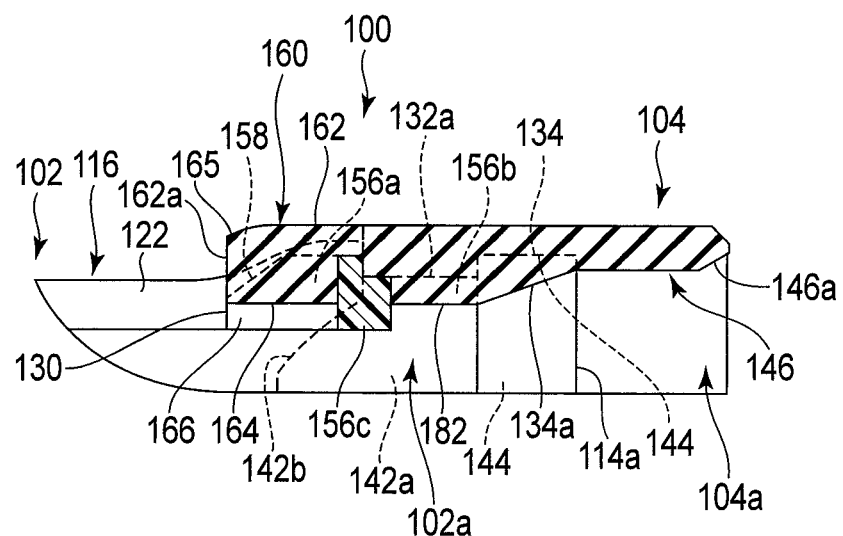
FIG. 5E is a schematic sectional view taken along line 5E-5E in FIG. 5A.

The slit 156b on the proximal side contributes to the elastic deformation of the annular portion 114. For example, the flange portion 134 of the annular portion 114 is elastically deformed when the engagement is established between the lock depressed portion 152 and the lock pin 74. As shown in FIGS. 5A and 5E, the cover main body 100 is provided with a buffer portion (structure) 160 that has an end portion (distal end portion) 162a at the same position as the distal end position of the fragile portion 156 along the longitudinal axis L, and that is configured to reduce a force exerted from the distal side of the fragile portion 156 onto the fragile portion 156. The buffer portion 160 is formed at a position in the first region with reference to the wall surface 64a of the recess portion 64 on the proximal side along the longitudinal axis L while the cover 14 is attached to the distal framing portion 22. FIG. 5E shows a state in which the end portion 162a of the buffer portion 160 is located at the same position as the distal end position of the fragile portion 156 along the longitudinal axis L. However, the end portion 162a may be located at a position which is distal to the position of the distal end of the fragile portion 156. The cover main body may be structured such that when some object comes into contact with the cover 14, the end portion 162a of the buffer portion 160 comes into contact with the object before the distal end of the fragile portion 156 comes into contact with the object.

In this embodiment, the buffer portion 160 is integrally provided on the distal end of the second cover main body 104 along the longitudinal axis L. The buffer portion 160 is provided at the distal end of the second cover main body 104, and has an extending portion (protruding portion) 162 extending (protruding) toward the distal side of the annular portion 114 of the first cover main body 102. The extending portion 162 has the end portion (distal end portion) 162a at the same position as the distal end position of the slit 156a of the fragile portion 156 along the longitudinal axis L or at the position distal to the distal end position of the fragile portion 156. Note that in this embodiment, the proximal end of the extending portion 162 coincides with the distal end (attachment protruding portion 142b) of the second cover main body 104.

The extending portion 162 of the buffer portion 160 is provided distal to the second cover main body 104 and is shaped to cover the outside (the edge portion and its peripheral region) of the slit 156a of the fragile portion 156. The extending portion 162 may extend straight or may be bent as appropriate. The extending portion 162 has a protruding portion (attachment portion) 164 that protrudes toward the longitudinal axis L inside the cover 14 and can be externally fitted in the slit 156a. The extending portion 162 of the buffer portion 160 is integrally formed with the second cover main body 104, and hence the protruding portion 164 of the buffer portion 160 integrally formed with the extending portion 162 has higher flexibility than the material of the first cover main body 102 which forms the slit 156a. The extending portion 162 of the buffer portion 160 surrounds the slit 156a and its surroundings while the protruding portion 164 is fitted in the slit 156a. This prevents part of a duct in the body into which the insertion section 12 is inserted from being caught by an edge portion (edge) of the slit 156a.

The extending portion 162 of the buffer portion 160 has an inclined plane 165 on the opposite side to the side on which the protruding portion 164 is formed. The inclined plane 165 approaches the longitudinal axis L as the inclined plane 165 extends toward the distal side along the longitudinal axis L. The inclined plane 165 is continuous with the end portion 162a of the buffer portion 160. When an external force is exerted on the inclined plane 165 from the distal side to the proximal side along the longitudinal axis L and/or an external force is exerted from outside to inside in the radial direction, the extending portion 162 of the buffer portion 160 comes into tight contact with the outer peripheral surface of the first cover main body 102 and keeps resistant to curling up.

The extending portion 162 of the buffer portion 160 has an inclined plane 166 on the side on which the protruding portion 164 is formed. The inclined plane 166 is directed to the longitudinal axis L, and is also directed to the proximal side along the longitudinal axis L. The inclined plane 166 of the extending portion 162 of the second cover main body 104 is brought into contact with the inclined plane 158 of the slit 156a of the first cover main body 102. In addition, a surface (a portion adjacent to the proximal side of the end portion 162a) of the extending portion 162 of the buffer portion 160 which is located on the opposite side to the inclined plane 166 is the inclined plane 165 that approaches the central axis C as the inclined plane 165 extends toward the distal side along the longitudinal axis L. Accordingly, when a load is exerted on the end portion 162a (and a region including the inclined plane 165) of the extending portion 162 from the distal side along the longitudinal axis L during the use of the endoscope 10, the inclined plane 166 of the extending portion 162 is kept in contact with (fitted to) the inclined plane 158 near the distal end of the slit 156a of the fragile portion 156. This prevents the inclined plane 166 of the extending portion 162 from unintentionally separating and curling up from the inclined plane 158 near the distal end of the slit 156a of the fragile portion 156, resulting in disengaging the protruding portion 164 from the slit 156a. On the other hand, the user can check the state of the coupling portion 156c of the fragile portion 156 by peeling back the extending portion 162.

The inner peripheral surface of the second cover main body 104 has a protruding portion (attachment portion) 182 that protrudes toward the central axis C and can be fitted in the other slit 156b of the fragile portion 156 from outside. The protruding portion 182 is integrally formed with the second cover main body 104, and hence has higher flexibility than the material of the first cover main body 102 forming the slit 156b. The first cover main body 104 covers the slit 156b and its surroundings while the protruding portion 182 is fitted in the slit 156b. This prevents part of a duct in the body into which the insertion section 12 is inserted from being caught by an edge portion of the slit 156b.

When forming the cover 14, the user attaches the second cover main body 104 to the first cover main body 102 shown in FIGS. 4A to 4C. In this case, first of all, the user checks that the coupling portion 156c exists between the slit 156a and the slit 156b of the first cover main body 102 without any breakage, and the slits 156a and 156b are not continuous. Thereafter, as shown in FIGS. 5A to 5C, the user fits the second cover main body 104 to the first cover main body 102. The second cover main body 104 is then covered by the outer periphery of the annular portion 114 on the proximal side of the first cover main body 102. The buffer portion 160 provided on the distal side of the second cover main body 104 coverts the outside of the slit 156a of the fragile portion 156. The second cover main body 104 covers the outside of the slit 156b of the fragile portion 156. More specifically, the annular protruding portion 142a of the second cover main body 104 is fitted in the annular depressed portion 132a of the first cover main body 102, and the attachment protruding portion 142b of the second cover main body 104 is fitted in the attachment depressed portion 132b of the first cover main body 102. At this time, the protruding portion (attachment portion) 164 of the extending portion (protruding portion) 162 is fitted in the slit 156a of the first cover main body 102, and the protruding portion (attachment portion) 182 of the second cover main body 104 is fitted in the slit 156b of the first cover main body 102. With this operation, the first cover main body 102 and the second cover main body 104 according to this embodiment are fitted while being positioned at predetermined positions.

Note that the first cover main body 102 and the second cover main body 104 according to this embodiment may be positioned at the predetermined positions relative to each other by only fitting the annular protruding portion 142a of the second cover main body 104 in the annular depressed portion 132a of the first cover main body 102 and fitting the attachment protruding portion 142b of the second cover main body 104 in the attachment depressed portion 132b of the first cover main body 102. Alternatively, when the annular depressed portion 132a of the first cover main body 102 and the annular protruding portion 142a of the second cover main body 104 are formed into simple annular shapes, the first cover main body 102 and the second cover main body 104 may be positioned by only fitting the protruding portion (attachment portion) 164 of the extending portion (protruding portion) 162 in the slit 156a of the first cover main body 102 and fitting the protruding portion (attachment portion) 182 of the second cover main body 104 in the slit 156b of the first cover main body 102.

The inclined plane 166 of the extending portion 162 of the second cover main body 104 is brought into contact with and fitted to the inclined plane 158, of the slit 156a of the first cover main body 102, which is formed near the proximal side edge 130 of the open edge 116. With this operation, the second cover main body 104 is fitted to the first cover main body 102 to form the cover 14. At this time, the end portion 162a of the buffer portion 160 is located at the same position as that of the proximal side edge 130 of the open edge 116 along the longitudinal axis L. In addition, the end portion 162a of the buffer portion 160 slightly protrudes with respect to the proximal side edge 130 of the open edge 116 on the distal side along the longitudinal axis L.

As shown in FIGS. 5A to 6B, the cover 14 is attached to the distal framing portion 22 by aligning the cover 14 with the distal framing portion 22 in the peripheral direction with respect to the longitudinal axis L. The guide protruding portion 154 of the cover 14 is engaged with the guide groove 70 of the main body 52 of the distal framing portion 22, and the cover 14 is moved along the longitudinal axis L. This prevents the cover 14 from being displaced with respect to the distal framing portion 22 in the peripheral direction.

Furthermore, when the cover 14 is attached to the distal framing portion 22, the skirt portion 146a of the attachment portion 146 of the second cover main body 104 of the cover 14 is in contact with the lock pin 74 of the distal framing portion 22. At this point, the attachment portion 146, which has elasticity, is elastically deformed to move on the lock pin 74. The lock pin 74 of the distal framing portion 22 is therefore brought into contact with the skirt portion 134a of the annular portion 114 of the first cover main body 102. At this point, the annular portion 114 is elastically deformed by the slit 156b. As a result, the lock depressed portion 152 is locked to the lock pin 74 of the distal framing portion 22. Then, the displacement of the cover 14 with respect to the distal framing portion 22 in the axial direction and in the peripheral direction can be prevented.

The skirt portion 146a of the attachment portion 146 of the second cover main body 104 may be in contact with the thread wound portion 24a at the distal end of the bending portion 24 and/or the insulation member 25 on the distal side of the thread wound portion 24a. The inner peripheral surface of the skirt portion 146a is elastically deformed and stretched out in a radial direction outwardly from the insulation member 25 and the thread wound portion 24a. As a result, the inner peripheral surface of the skirt portion 146a is brought into tight contact with the insulation member 25 and/or the thread wound portion 24a. The thread wound portion 24a is prepared by annularly winding a thread and applying an adhesive to the outer periphery of the thread to provide an electrically insulated portion in which the applied adhesive is fixed.

When the cover 14 attached to the distal framing portion 22 is viewed in a section perpendicular to the longitudinal axis L and then the section is divided into the first region and the second region different from each other as described above, the lock depressed portion 152 is located in the first region, and the guide protruding portion 154 is located in the second region.

The fragile portion 156 is positioned not on the flat portion 62, but on the wire moving portion (wire moving region) 68 of the main body 52 of the distal framing portion 22, according to the present embodiment. In other words, the wire moving portion (wire moving region) 68 is provided inside at a position corresponding to where the fragile portion 156 of the first cover main body 102 is formed. This means that the breakable coupling portion 156c of the fragile portions 156 is positioned in the same space as the wire moving portion 68. Note that the recess portion 64 of the swing table 42 is located on the distal side of the wire moving portion 68 of the wire moving portion 68 along the longitudinal axis L. Accordingly, the buffer portion 160 and the fragile portion 156 each are formed at a position, in the first region with reference to the wall surface 64a of the recess portion 64, which is located on the proximal side along the longitudinal axis L. At this time, as shown in FIG. 6A, the cover main body 100 is positioned to the distal framing portion 22 in a state in which the swing table 42 and the end portion 162a and the fragile portion 156 of the buffer portion 160 are provided on a straight line along the longitudinal axis L. The illumination window 32a, the observation window 34a, and the nozzle 35 are exposed with respect to the open edge 116 of the cover 14, and the swing table 42 is exposed so as to be swingable within an appropriate range. Accordingly, when the cover main body 100 is attached to the distal framing portion 22, the open edge 116 exposes the illumination optical system 32, the observation optical system 34, and the nozzle 35 provided for the distal framing portion 22. In addition, the open edge 116 allows the treatment instrument 20 extending from the swing table 42 of the distal framing portion 22 through the insertion section 12 to protrude outside through the open edge 116.

Part of the distal face 42c and the distal end portion 42b of the swing table 42 are exposed when viewed from the distal side along the longitudinal axis L while the cover 14 is properly attached to the distal framing portion 22. Accordingly, when the treatment instrument 20 is guided by the swing table 42 to protrude relative to the swing table 42, the depressed portion 124 can prevent the treatment instrument 20 from interfering with the cover 14. Note that a gap G is formed between the swing table 42 and the first cover main body 102 to prevent friction between the swing table 42 and the first cover main body 102 while the first cover main body 102 is properly attached to the distal framing portion 22. That is, the gap G is formed between the distal face 42c of the swing table 42 and the depressed portion 124 of the cover 14. Even if the swing table 42 swings, although the volume of gap between the distal face 42c of the swing table 42 and the depressed portion 124 of the cover 14 varies, the presence of the gap is maintained. This prevents the first cover main body 102 from interfering with the movement of the swing table 42. In the cross section of the distal framing portion 22 to which the cover 14 is attached, the outer peripheral surface as indicated with a reference number 118 forms a partial ring shape shown in FIG. 5D.

Observation and treatment by inserting the insertion section 12 of the endoscope 10 into a duct such as a lumen is performed when the cover 14 is attached to the distal framing portion 22. It should be noted that part of the fragile portion 156 is covered and protected by the extending portion 162 of the buffer portion 160 and the second cover main body 104 from outside. For this reason, even if the fragile portion 156 hits the interior wall or the like during the insertion into a duct in a body cavity or the like, or during a treatment using the treatment instrument 20 inserted into the insertion section 12, the buffer action obtained by a rubber material or the like prevents loads from being exerted on the slits 156a and 156b of the fragile portion 156 toward the opposite sides along the circumferential direction and suppresses the breakage of the fragile portion 156.

As shown in FIG. 6C, the treatment instrument 20 such as an elongated guide wire or appropriate forceps is made to extend from the open edge 116 to outside of the distal framing portion 22 of the endoscope 10 and the cover 14 through the channel 36 inside the insertion section 12 along the swing table 42 of the swing mechanism 38. The direction of the treatment instrument 20 is changed by the swinging movement of the swing table 42 of the swing mechanism 38. As the user moves the lever 46 of the operation section 16 from the first position (i.e., when the lever 46 is raised to the maximum) to the second position (i.e., when the lever 46 is lowered to the maximum), the swing table 42 moves from the position (lowered position) indicated by FIG. 6B to the position (raised position) indicated by FIG. 6C. Accordingly, the treatment instrument 20 is bent as shown in, for example, FIG. 6C. At this time, the outer peripheral surface of the treatment instrument 20 comes into contact with the end portion 162a of the extending portion 162 of the buffer portion 160 of the cover 14. This allows the treatment instrument 20 to be supported between the swing table 42 and the end portion 162a of the buffer portion 160 of the cover 14. Accordingly, when the treatment instrument 20 protruding from the distal framing portion 22 through the insertion section 12 comes into contact with the end portion 162a of the buffer portion 160 as the position of the swing table 42 is changed, the end portion 162a of the buffer portion 160 can support the treatment instrument 20 in a state in which the movement of the treatment instrument 20 in the axial direction is suppressed. That is, the treatment instrument 20 can be held and fixed between the swing table 42 and the end portion 162a of the buffer portion 160 of the cover 14. At this time, friction is generated between the outer peripheral surface of the treatment instrument 20 and the end portion 162a of the buffer portion 160 of the cover 14, and hence the displacement of the treatment instrument 20 in its axial direction can be suppressed.

Note that the distal end of the slit 156a of the fragile portion 156 is continuous with the proximal side edge 130 of the open edge 116. For this reason, if the end portion 162a of the buffer portion 160 does not exist, the distal end of the slit 156a of the fragile portion 156 directly receives a load from the treatment instrument 20. In this embodiment, the end portion 162a of the buffer portion 160 is located at the same position as that of the proximal side edge 130 or on the distal side. That is, the outer peripheral surface of a portion, of the treatment instrument 20 raised to the maximum by the swing table 42, which faces the proximal side with respect to the longitudinal axis L is at a position to come into contact with the end portion 162a of the buffer portion 160. For this reason, even if the distal end of the fragile portion 156 receives a load, the distal end receives the load immediately after the end portion 162a of the buffer portion 160 receives the load from the treatment instrument 20. This prevents the distal end of the fragile portion 156 from directly receiving the load from the treatment instrument 20. The end portion 162a of the buffer portion 160 supports the treatment instrument 20, and also reduces a force exerted on the fragile portion 156.

At this time, when the treatment instrument 20 comes into contact with the end portion 162a of the buffer portion 160, an external force is exerted on the treatment instrument 20. This brings the inclined plane 166 of the second cover main body 104 into tight contact with the inclined plane 158 of the first cover main body 102. Although the inclined planes 158 and 166 come into tight contact with each other upon exertion of an external force, the inclined planes 158 and 166 are formed in inclined states (fitted states) in which they are difficult to separate from each other. This prevents the extending portion 162 having flexibility from curling up and exposing the fragile portion 156 upon reception of a load from the treatment instrument 20.

Note that when the treatment instrument 20 is supported by the end portion 162a of the buffer portion 160, the end portion 162a is pressed on the proximal side along the longitudinal axis L. This can make the protruding portion 164 of the buffer portion 160 come into contact with the proximal end of the slit 156a of the fragile portion 156, i.e., the distal end of the coupling portion 156c. As described above, because the protruding portion 164, of the buffer portion 160, which is fitted in the slit 156a of the first cover main body 102 is integrally formed with the second cover main body 104, the protruding portion 164 has higher flexibility than the material of the first cover main body 102 forming the slit 156a. In addition, the fragile portion 156 has resistance to breakage while the treatment instrument 20 is supported and fixed on the end portion 162a of the buffer portion 160. More specifically, even when the end portion 162a of the buffer portion 160 moves from the distal side to the proximal side along the longitudinal axis L due to elastic deformation, the coupling portion 156c of the fragile portion 156 has resistance to breakage that makes the slits 156a and 156b be continuous with each other. Accordingly, even if the protruding portion 164 comes into contact with the coupling portion 156c while the treatment instrument 20 is supported (fixed) on the end portion 162a of the buffer portion 160, the buffer function of the buffer portion 160 makes it difficult to cause breakage in the fragile portion 156.

Even if an object unintentionally comes into contact with the end portion 162a of the buffer portion 160, the buffer portion 160 can suppress a load on the fragile portion 156. This can prevent the fragile portion 156 from being broken by an external force (including an intentional force exerted by the treatment instrument 20 or the like and an unintentional force). In addition, this can prevent the end portion 162a of the buffer portion 160 from causing tissue or the like in the body to be caught by the end portion of the slit 156a of the fragile portion 156, and can prevent the extending portion 162 of the buffer portion 160 from causing tissue or the like in the body to be caught by the edge portion of the slit 156a of the fragile portion 156.

After the use of the endoscope 10, the cover 14 is removed from the distal framing portion 22. The first cover main body 102 and the second cover main body 104 of the cover 14 are disposed of as-is. The distal framing portion 22, from which the cover 14 is removed, is washed, disinfected, and sterilized. In other words, the endoscope 10, from which the cover 14 is removed, is washed, disinfected, and sterilized to be reused. Because the cover 14 is removed from the distal framing portion 22, washing can be readily conducted, not only for the vicinity of the illumination window 32a of the illumination optical system 32 and the observation window 34a of the observation optical system 34, but also for the channel 36 and the swing mechanism 38.

Figure 7B:
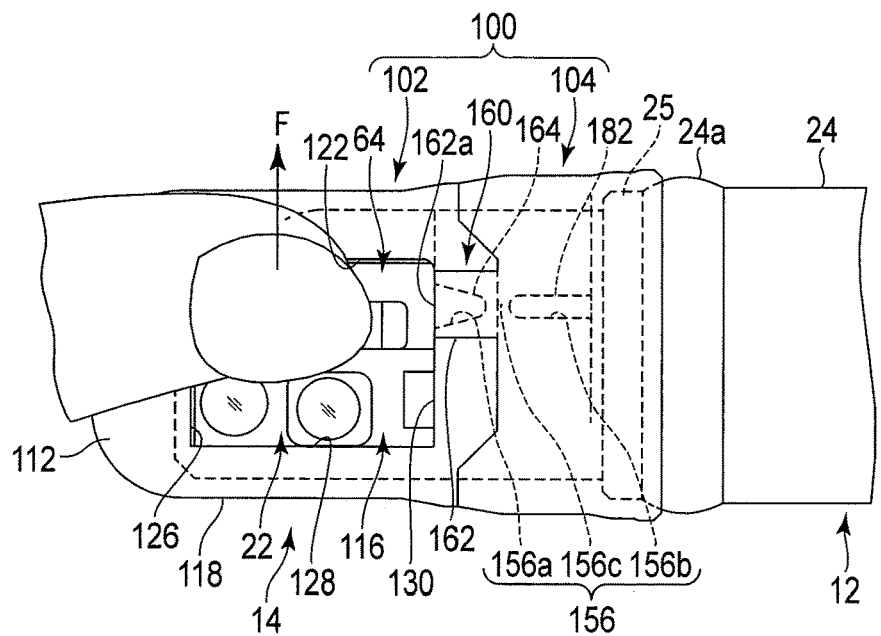
FIG. 7B is a schematic top view showing the cover attached to the distal framing portion of the endoscope according to the first embodiment in a state in which the user tries to break a fragile portion.
Figure 8:
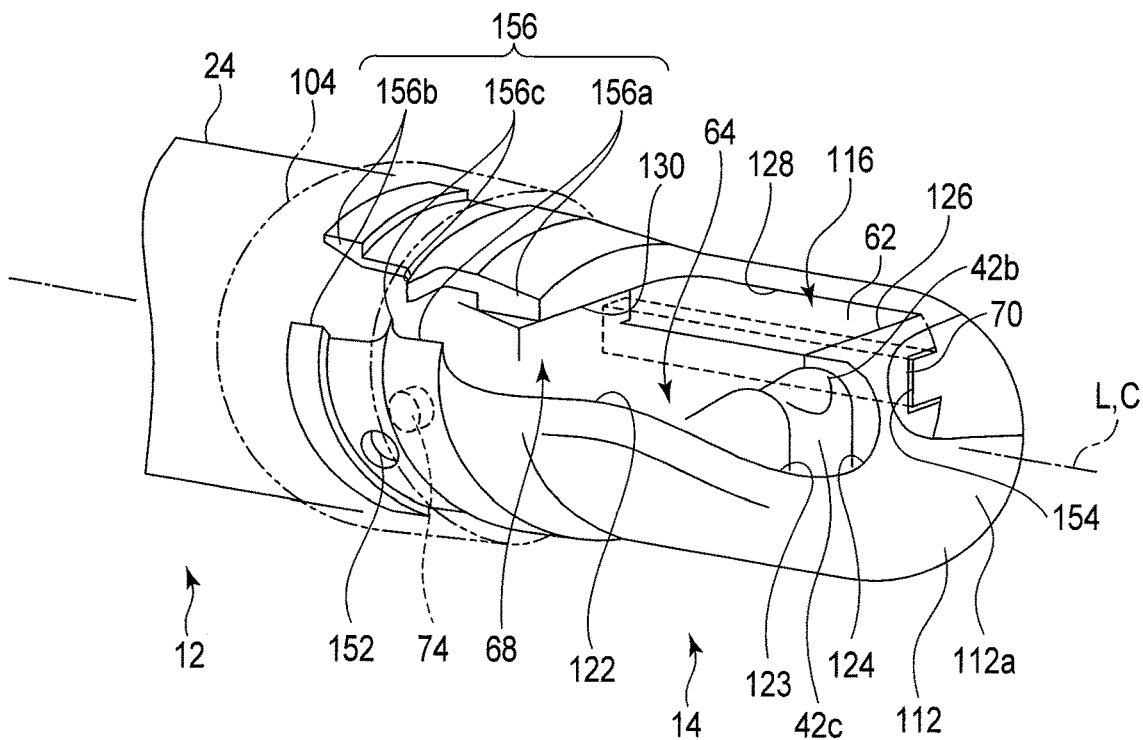
FIG. 8 is a schematic perspective view showing a state in which the fragile portion of the cover attached to the distal framing portion of the endoscope according to the first embodiment is broken so as to allow the user to remove the cover from the distal framing portion.

When the cover 14 is removed from the distal framing portion 22, the user presses the pressure receiving portion 123 shown in FIG. 7A in the direction indicated by symbol F and spreads the right side edge 122 away from the wall surface 64a of the recess portion 64 using the force of his/her finger (see FIG. 7B). With the guide groove 70 engaged with the guide protruding portion 154, the cover 14 is prevented from being turned in the circumferential direction of the longitudinal axis L. A crack (breakage portion) is produced in the coupling portion 156c of the fragile portion 156 in a direction (a direction along the longitudinal axis L) orthogonal to the direction to which a breaking force is applied (i.e., the circumferential direction of the longitudinal axis L), and the coupling portion 156c is broken along the longitudinal axis L. Thus, when the coupling portion 156c of the fragile portion 156 is broken along the longitudinal axis L, as shown in FIG. 8, the annular portion 114 is split at the slits 156a and 156b formed in advance at a position along the fragile portion 156 (predetermined position). Because the slits 156a and 156b are provided, the fragile portion 156 can break the coupling portion 156c within a predetermined short cut length range.

With the breakage of the fragile portion 156, the engagement of the lock depressed portion 152 with the lock pin 74 of the distal framing portion 22 is released.

A portion, of the coupling portion 156c of the fragile portion 156, which is located near the slit 156a can peel back the extending portion 162. This allows the user to directly visually check the breakage portion of the fragile portion 156. Note that the coupling portion 156c of the fragile portion 156 generates a sound when the coupling portion 156c is broken. In particular, the walls 68a, 68b, and 68c of the wire moving portion 68 form a closed space between themselves and the first cover main body 102. Accordingly, when the fragile portion 156 is broken, a breaking sound reverberates through the wire moving portion 68. The user can directly visually check and recognize whether a breakage portion is formed and also can recognize the breakage portion by hearing the breaking sound.

The position at which the user presses the cover 14 with his/her finger (see FIG. 7B) is not limited to the pressure receiving portion 123 shown in FIG. 7A. The position at which the user presses the cover 14 with his/her finger may be a position on the right side edge 122 which is near the fragile portion 156. In this case as well, the user can break the fragile portion 156.

The wire moving portion (wire moving region) 68 is formed on the lower side of the fragile portion 156. Accordingly, the user may peel back the extending portion 162 and directly press the fragile portion 156 with his/her finger to break the coupling portion 156c. In this case as well, the annular portion 114 is broken at a position (predetermined position) along the fragile portion 156. Therefore, the exerting direction of a force to break (rupture) the fragile portion 156 may be a circumferential direction relative to the longitudinal axis L or a radial direction toward the longitudinal axis L.

Note that when the user breaks the cover 14 by exerting a force F on the pressure receiving portion 123 and/or the right side edge 122 with his/her finger in the circumferential direction relative to the longitudinal axis L, a load is exerted on the coupling portion 156c of the fragile portion 156 in a direction to separate from the coupling portion 156c along the circumferential direction of the annular portion 114. At this time, although friction is generated between the extending portion 162 of the buffer portion 160 and the outer peripheral surface of the annular portion 114, the extending portion 162 is not structured to exert a buffer function against a load in the circumferential direction of the fragile portion 156. For this reason, when breaking the cover 14 by exerting a force on the pressure receiving portion 123 and/or the right side edge 122 with his/her finger in the circumferential direction relative to the longitudinal axis L, the user can break the fragile portion 156 of the cover 14 without peeling back the extending portion 162 of the buffer portion 160. That is, when the user intentionally breaks the cover 14, it is difficult for the buffer portion 160 to interfere with the breakage of the cover main body 100 of the cover 14.

After breaking the fragile portion 156 and releasing the engagement of the lock depressed portion 152 with the lock pin 74 by turning the cover 14 around the central axis C with respect to the distal framing portion 22, the cover 14 can be removed by moving it toward the distal side along the center axis C. At this time, when the user breaks the coupling portion 156c of the fragile portion 156 of the cover main body 100, the proximal side edge 130 of the open edge 116 is continuous with the proximal end of the cover main body 100. This makes it possible to more easily spread the annular portion 114 of the first cover main body 102 in the circumferential direction of the longitudinal axis L by elastic deformation. The second cover main body 104 is elastically deformable. This allows the user to remove the second cover main body 104, together with the first cover main body 102, from the distal framing portion 22.

When the user removes the cover 14 from the distal framing portion 22 with the finger, the manner of removal may differ depending on the user, for example, the position of the placement of the finger. This may make it difficult to stably perform the breakage of the fragile portion 156. The fragile portion 156 may be reliably broken by use of the jig (removal tool for the cover 14) 200 (see FIGS. 9A to 9F) described below. It is therefore preferable that the jig 200 be used when the cover 14 is removed from the distal framing portion 22 after the use of the endoscope 10. The jig 200 may be employed for the purpose of reliably breaking the cover 14 and preventing the reuse of the cover 14.

Figure 9A:
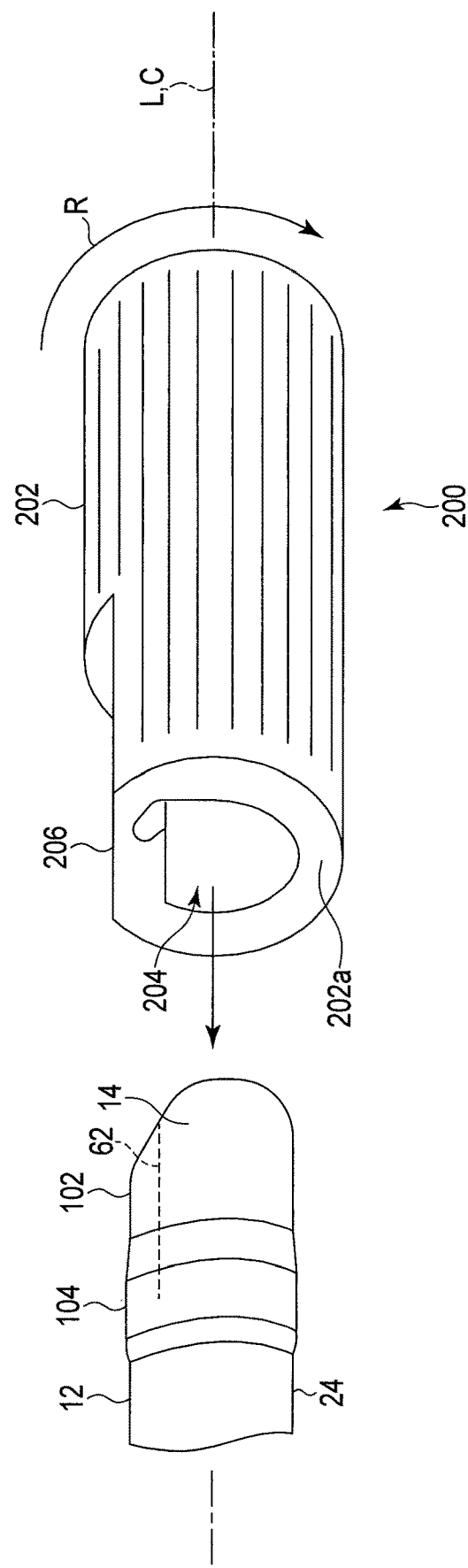
FIG. 9A is a schematic perspective view showing a state in which the user tries to remove the cover attached to the distal framing portion of the endoscope according to the first embodiment by using a jig.

The cover removal jig 200 is made of a rigid material such as a resin material that is more rigid than the first cover main body 102 of the cover 14, or made of a metallic material. For example, polycarbonate, modified PPE resin, glass-containing polysulfone, polyphenylsulfone, or stainless steel is used for the jig 200. As shown in FIG. 9A, the outer periphery of the jig 200 has a column 202 formed into an appropriate shape. An acting portion 204, which acts on the cover 14 when removing the cover 14 attached to the distal framing portion 22, is formed at one end 202a of the column 202. The acting portion 204 is shaped into a depression which covers the vicinity of the distal end 112a of the closed portion 112 of the cover 14.

Figure 9B:
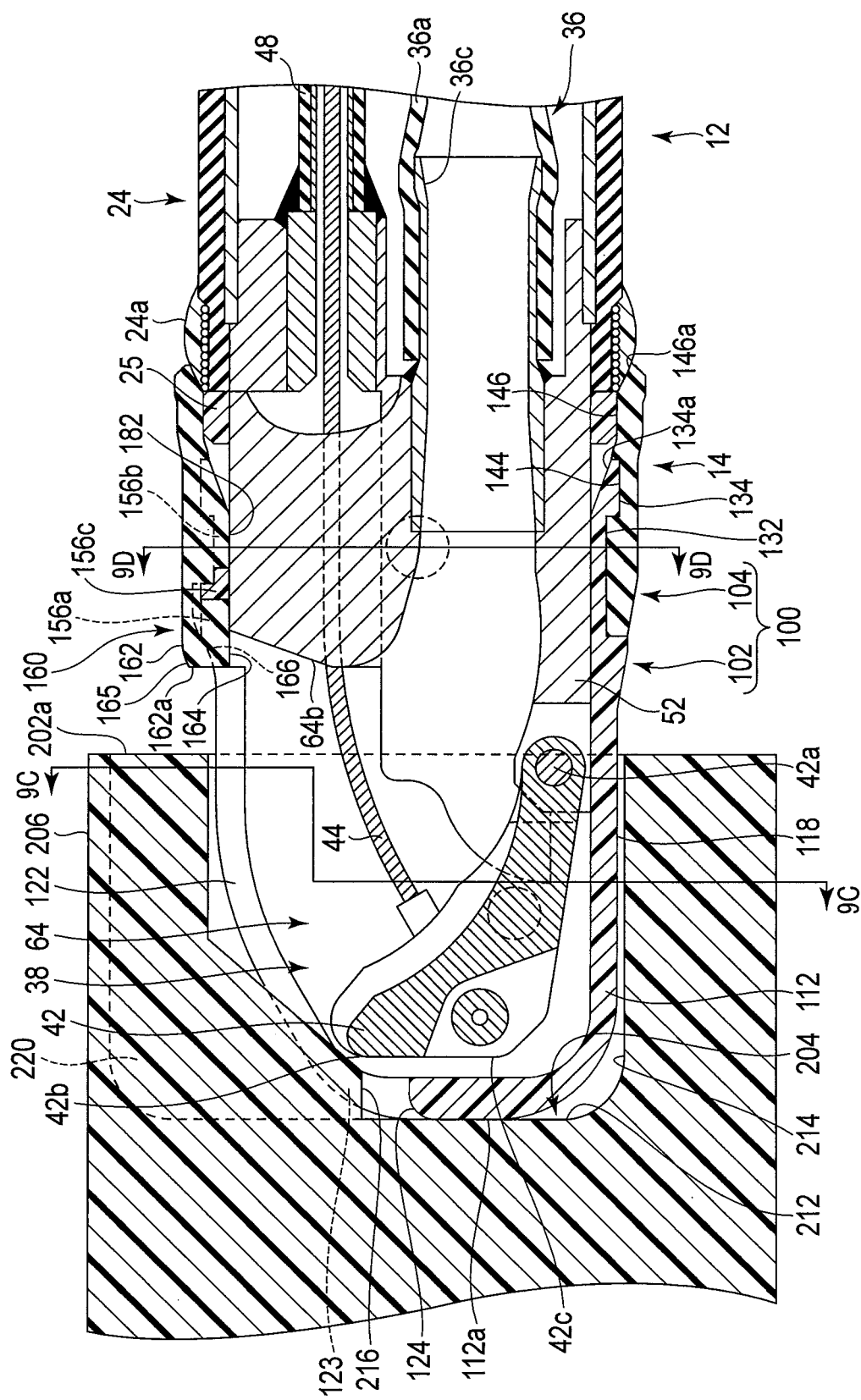
FIG. 9B is a schematic longitudinal sectional view showing a state in which the jig is fitted on the cover attached to the distal framing portion of the endoscope according to the first embodiment to remove the cover.
Figure 9C:
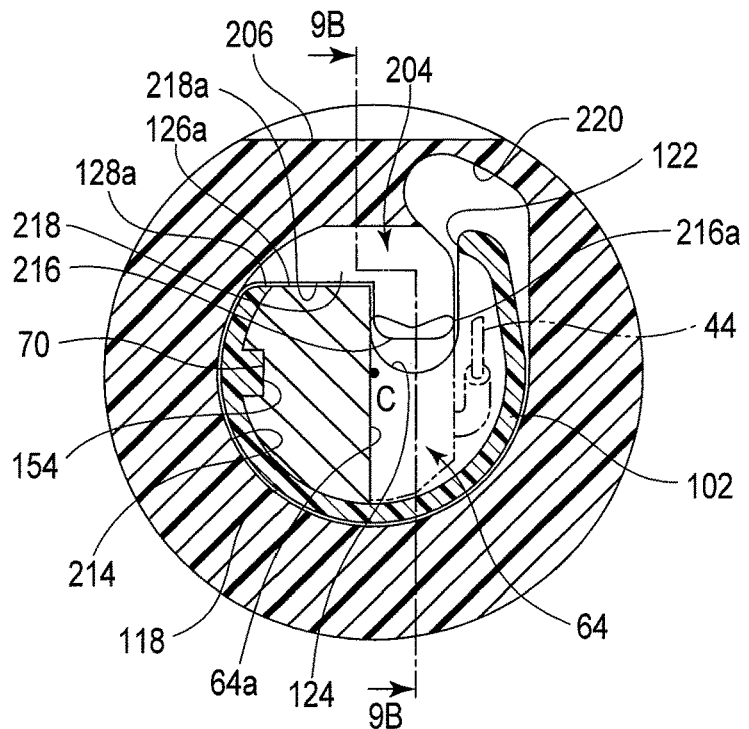
FIG. 9C is a schematic cross sectional view taken along line 9C-9C in FIG. 9B.

As shown in FIGS. 9B and 9C, the acting portion 204 has a bottom surface 212, a support peripheral surface 214 that is preferably orthogonal to the bottom surface 212, a first protruding portion 216 that is fitted to the U-shaped depressed portion 124 of the open edge 116 of the cover 14, a second protruding portion 218 that is fitted to the distal side covering portion 126a of the cover 14, and a retraction portion 220 into which part of the right side edge 122 of the open edge 116 of the broken cover 14 is retracted.

As shown in FIGS. 9A to 9D, the acting portion 204 at the one end 202a of the column 202 of the jig 200 is fitted to the distal framing portion 22 with the endoscope cover 14 attached.

As shown in FIG. 9B, the distal end 112a of the closed portion 112 of the cover 14 is brought into contact with the bottom surface 212. Thus, the bottom surface 212 regulates the length of the cover 14 to be inserted in the depressed acting portion 204 from the one end 202a of the jig 200, to be a certain length.

Figure 9D:
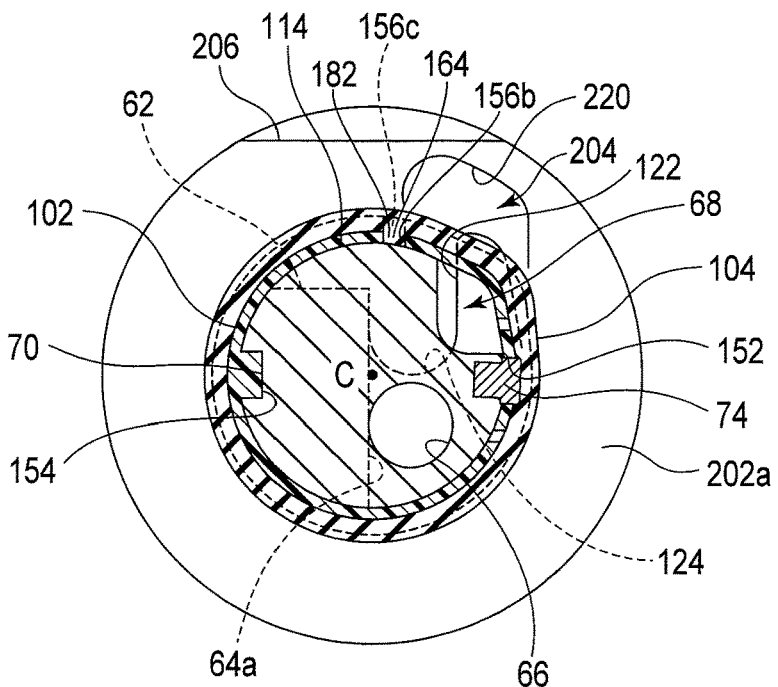
FIG. 9D is a schematic cross sectional view taken along line 9D-9D in FIG. 9B.

As shown in FIGS. 9C and 9D, the support peripheral surface 214 is formed as a part of the circular form. The central axis C of the acting portion 204 is defined by the support peripheral surface 214. The distance between the central axis C and the support peripheral surface 214, or in other words the radius of the acting portion 204, is formed to be slightly larger than the radius defined by the rotation peripheral surface 118, which forms a part of the circular cylinder of the cover 14. The rotation peripheral surface 118 of the cover 14 therefore abuts on and is thus supported by, the support peripheral surface 214. At this point, the support peripheral surface 214 is movable relative to the rotation peripheral surface 118 of the cover 14 around the central axis C.

As shown in FIG. 9B, the first protruding portion 216 protrudes from the bottom surface 212 toward the one end 202a of the column 202. The amount of protrusion of the first protruding portion 216 from the bottom surface 212 corresponds to the distance from the distal end portion 42b and the distal face 42c of the swing table 42, although the first protruding portion 216 is able to be brought into contact with the depressed portion 124 of the cover 14, while the distal end 112a of the closed portion 112 of the cover 14 is in contact with the bottom surface 212. Even if the swing table 42 is swung with the distal end 112a of the closed portion 112 of the cover 14 being in contact with the bottom surface 212, the first protruding portion 216 will not be brought into contact with the distal end portion 42b and the distal face 42c of the swing table 42. Moreover, the width of the first protruding portion 216 is determined to be slightly smaller than the width of the depressed portion 124 of the cover 14. The first protruding portion 216 of the jig 200 is provided with a pressure portion 216a which is brought into contact with the pressure receiving portion 123 provided between the depressed portion 124 and the right side edge 122 of the open edge 116 of the cover 14 (see FIG. 7A) when the jig 200 is turned with respect to the cover 14 in the peripheral direction of the central axis C.

The second protruding portion 218 shown in FIG. 9C protrudes toward the one end 202a of the column 202 from the bottom surface 212. The second protruding portion 218 is adjacent to the first protruding portion 216 in the peripheral direction of the central axis C. The second protruding portion 218 has an opposed surface 218a, which is preferably parallel to the distal side covering portion 126a. The opposed surface 218a may be in contact with the distal side covering portion 126a of the distal side edge 126 of the cover 14. The opposed surface 218a therefore may indirectly hold the flat portion 62 of the main body 52 of the distal framing portion 22.

The use of the jig 200 for removing the cover 14 attached to the distal framing portion 22 will be briefly explained below.

As shown in FIG. 9A, the acting portion 204 of the jig 200 is opposed to the distal framing portion 22 with the cover 14 attached. The orientation of the index 206 that causes the user to recognize the orientation of the jig 200 is determined to be parallel to the flat portion 62 of the distal framing portion 22. As shown in FIG. 9B, in this state, the acting portion 204 of the jig 200 is fitted to the distal framing portion 22 to which the cover 14 is attached. When the distal end 112a of the closed portion 112 of the cover 14 comes into contact with the bottom surface 212 of the acting portion 204 of the jig 200, the support peripheral surface 214 of the jig 200 coincides with the central axis C of the rotation peripheral surface 118 of the cover 14. As shown in FIG. 9C, the first protruding portion 216 of the jig 200 is fitted in the depressed portion 124 of the open edge 116 in the cover 14. The second protruding portion 218 of the jig 200 is located near or in contact with the distal side covering portion 126a of the cover 14.

Figure 9E:
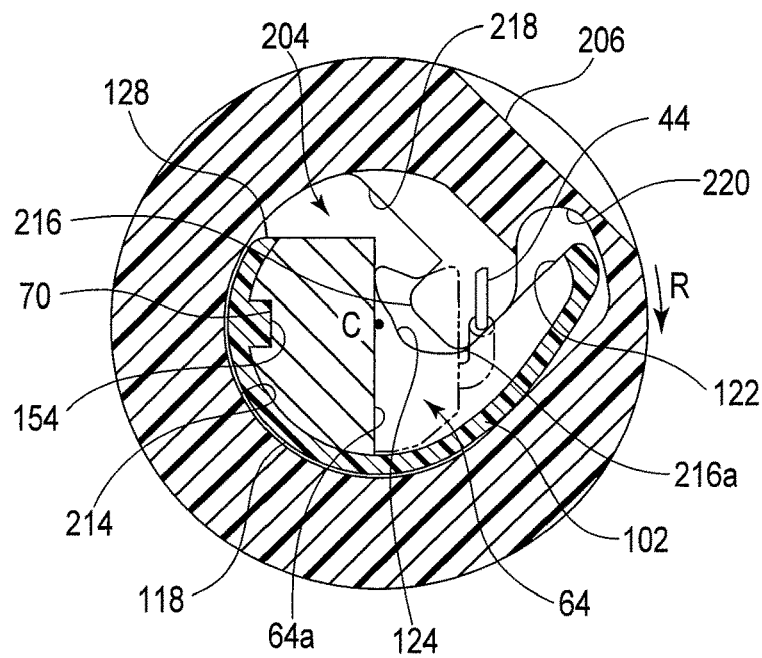
FIG. 9E is a schematic cross sectional view taken along line 9C-9C in FIG. 9B, showing a state in which the jig in the state shown in FIGS. 9B and 9C is rotated relative to the cover in the direction indicated by an arrow R in FIG. 9A.

The user rotates the jig 200 in the direction indicated by an arrow R in FIG. 9E with respect to the distal framing portion 22 and the cover 14. That is, the user causes the support peripheral surface 214 of the jig 200 having the central axis C common to the rotation peripheral surface 118 of the cover 14 to pivot about the central axis C.

As shown in FIGS. 9C and 9E, the pressure receiving portion 123 provided between the right side edge 122 and the depressed portion 124 of the open edge 116 (see FIG. 7A) is being pressed by the pressure portion 216a of the first protruding portion 216, while the opposed surface 218a of the second protruding portion 218 of the jig 200 is being moved away from the distal side covering portion 126a of the cover 14.

Figure 9F:
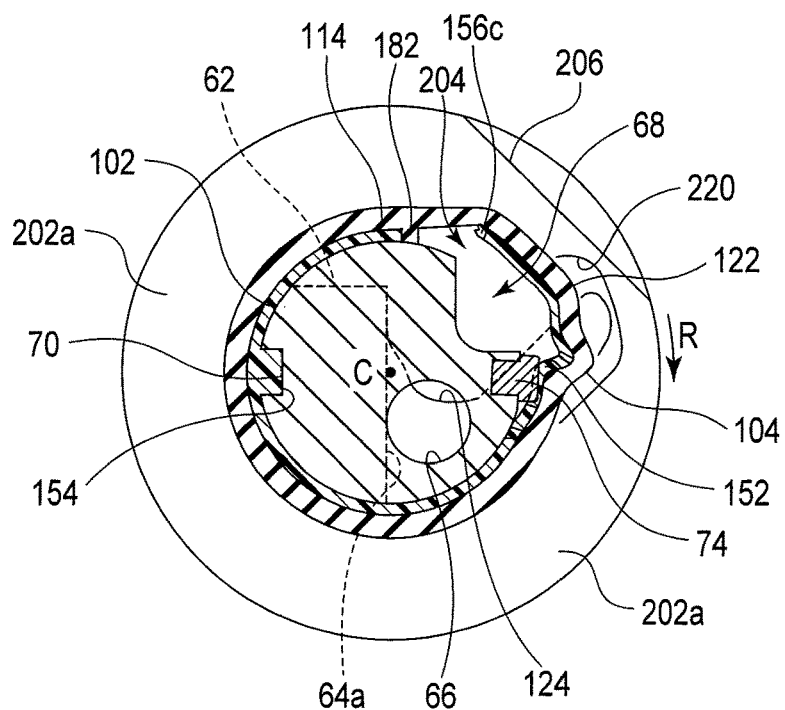
FIG. 9F is a schematic cross sectional view taken along line 9D-9D in FIG. 9B, showing a state in which the jig in the state shown in FIGS. 9B and 9D is rotated relative to the cover in the direction indicated by the arrow R in FIG. 9A.

As shown in FIGS. 9D and 9F, the amount of operation force of the jig 200 is applied to the coupling portion 156c between the slits 156a and 156b of the cover 14 facing the first protruding portion 216 of the jig 200 via the pressure receiving portion 123, the right side edge 122, and the proximal side edge 130, as a result of which the coupling portion 156c is broken. Due to the breakage of the coupling portion 156c, part of the attachment portion 132 of the annular portion 114 including the lock depressed portion 152 moves in the peripheral direction, while the engagement of the guide protruding portion 154 of the cover 14 with the guide groove 70 of the distal framing portion 22 is maintained. In conjunction with the breakage of the coupling portion 156c, the engagement of the lock depressed portion 152 with the lock pin 74 is released.

At this time, when the user tries to break the cover 14 by using the jig 200 as when trying to break the cover 14 with his/her finger, the buffer portion 160 does not easily interfere with the breakage of the cover main body 100 of the cover 14.

Then, the jig 200 is pulled to the distal side along the longitudinal axis L from the cover 14 in which the fragile portion 156 is broken. As shown in FIG. 8, the annular portion 114 of the cover 14 is split by the slits 156a and 156b formed in advance at a position (predetermined position) along the fragile portion 156. The cover 14 may be pinched by the user's fingers, or by a forceps or the like to remove the cover 14 from the distal framing portion 22 to the distal side along the longitudinal axis L. The cover 14 can be easily removed by the jig 200, while sanitation and safety is ensured for users (surgeons and surgical staff).

As described above, the endoscope 10 according to the present embodiment realizes the following.

The end portion 162a of the buffer portion 160 of the cover 14 can support and fix the treatment instrument 20 between itself and the swing table 42 raised by the operation of the lever 46. This allows the buffer portion 160 of the cover 14 to suppress the movement of the treatment instrument 20 in its axial direction while the swing table 42 is raised.

When the swing table 42 is raised, the treatment instrument 20 comes into contact with the end portion 162a of the extending portion 162 of the buffer portion 160 of the cover 14. At this time, although a load is exerted on the fragile portion 156 via the buffer portion 160, the buffer function of the buffer portion 160 and the resistance property of the fragile portion 156 can prevent the fragile portion 156 from being broken. In addition, the fragile portion 156 including the slits 156a and 156b and the coupling portion 156c and its surroundings are covered by the second cover main body 104 and the buffer portion 160 integrally formed with the second cover main body 104. Accordingly, even if an unintentional load is externally exerted (application of unintentional force) on the fragile portion 156, the buffer function of the buffer portion 160 and the second cover main body 104 can prevent the fragile portion 156 from being broken. In addition, not only the fragile portion 156 including the slits 156a and 156b and the coupling portion 156c but also its surroundings are covered. This can prevent the edge portions of the slits 156a and 156b of the fragile portion 156 from being caught by an external object.

The buffer portion 160 can actively buffer a load in a direction along the longitudinal axis L and prevent an object from contacting the end face of the fragile portion 156. On the other hand, the buffer portion 160 is not structured to actively suppress the breakage of the annular portion 114 along the longitudinal axis L. Accordingly, when the user removes the cover 14 from the distal framing portion 22, he/she can break the coupling portion 156c of the fragile portion 156 by exerting a force on the coupling portion 156c in, for example, the circumferential direction, thus easily removing the cover 14 from the distal framing portion 22.

It is possible to prevent the extending portion 162 of the buffer portion 160 from being unintentionally peeled back by the inclined planes 165 and 166 due to an external load. On the other hand, the extending portion 162 of the buffer portion 160 has flexibility, which allows the user to peel back the extending portion 162 by elastic deformation. This allows the user to visually check the state of the fragile portion 156 (whether the coupling portion 156c is broken) before the cover 14 is attached to the distal framing portion 22. In addition, even while the cover 14 is attached to the distal framing portion 22, the user can visually check the state of the fragile portion 156 by peeling back the extending portion 162 of the buffer portion 160. For this reason, even when, for example, the cover 14 is unintentionally brought into contact with some object, the user can visually check the state of the fragile portion 156 by peeling back the extending portion 162 while the cover 14 is attached to the distal framing portion 22.

This embodiment can therefore provide the endoscope cover 14 and the endoscope 10 which can suppress the exertion of a load on the fragile portion 156 when, for example, the insertion section 12 is inserted into the body or while the insertion section 12 is used during insertion into the body.

Note that the fragile portion 156 of the cover 14 is preferably formed at a position separated from the guide protruding portion 154 of the cover 14 in the circumferential direction centered on the central axis C. Accordingly, the deformation amount of the fragile portion 156 can be increased relative to the deformation amount of the guide protruding portion 154 of the cover 14 in the circumferential direction centered on the central axis C. When the user removes the cover 14 from the distal framing portion 22, he/she can reliably break the fragile portion 156.

In the embodiment, the example in which the lock pin 74 is arranged in the distal framing portion 22 to protrude outwardly in the radial direction with the lock depressed portion 152 arranged in the inner endoscope cover 14 has been described, but the arrangement of the projection and depression may be reversed. That is, a lock depressed portion may be formed in the distal framing portion 22, and a lock pin may be formed in the cover 14 to be engaged with the lock depressed portion.

Modification examples of the first embodiment are now briefly described. It should be noted that these modification examples can be suitably combined.

Figure 10A:
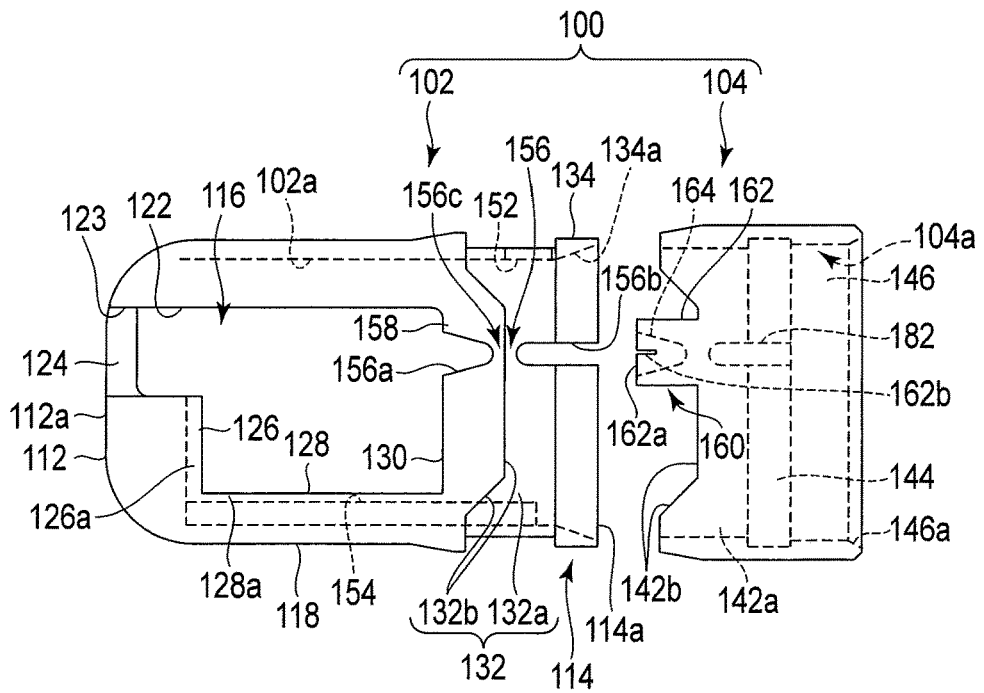
FIG. 10A is a schematic view showing an exploded state of the endoscope cover attached to the distal framing portion of the endoscope according to the first modification example of the first embodiment.
Figure 10B:
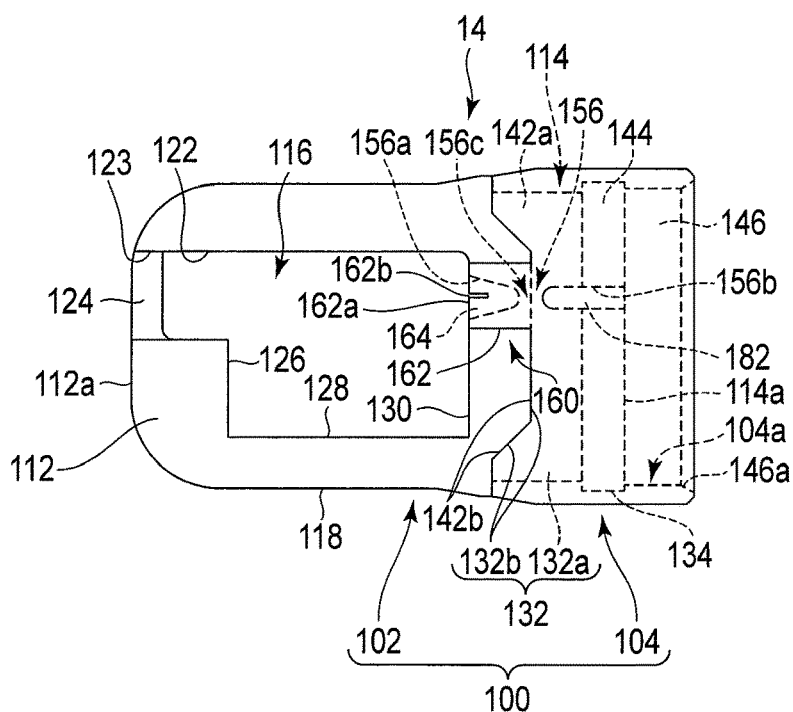
FIG. 10B is a schematic view showing the cover attached to the distal framing portion of the endoscope according to the first modification example of the first embodiment.

The first modification example will be described with reference to FIGS. 10A and 10B.

A notch 162b facing the proximal side along the longitudinal axis L is formed at a position including the end portion 162a of the extending portion 162. The notch 162b can increase the deformation amount of the end portion 162a of the extending portion 162 even with the use of the same material as that in the first embodiment when, for example, the treatment instrument 20 (see FIG. 6C) comes into contact with the end portion 162a of the extending portion 162. This can increase the buffer function of the fragile portion 156 when the treatment instrument 20 comes into contact with the end portion 162a of the extending portion 162 as compared with the first embodiment.

Accordingly, the buffer function of the buffer portion 160 and the second cover main body 104 can prevent the fragile portion 156 from being broken by an unintentional external load (application of unintentional force) on the fragile portion 156. In addition, increasing the deformation amount of the end portion 162a of the extending portion 162 can increase the contact area between the treatment instrument 20 and the end portion 162a of the extending portion 162. This makes it possible to reliably fix the treatment instrument 20 raised by the swing table 42 to the end portion 162a of the extending portion 162.

Therefore, the cover 14 according to this modification example can prevent a load from being exerted on the fragile portion 156 when the insertion section 12 is inserted in the body or when the insertion section 12 is used during insertion.

Figure 11A:
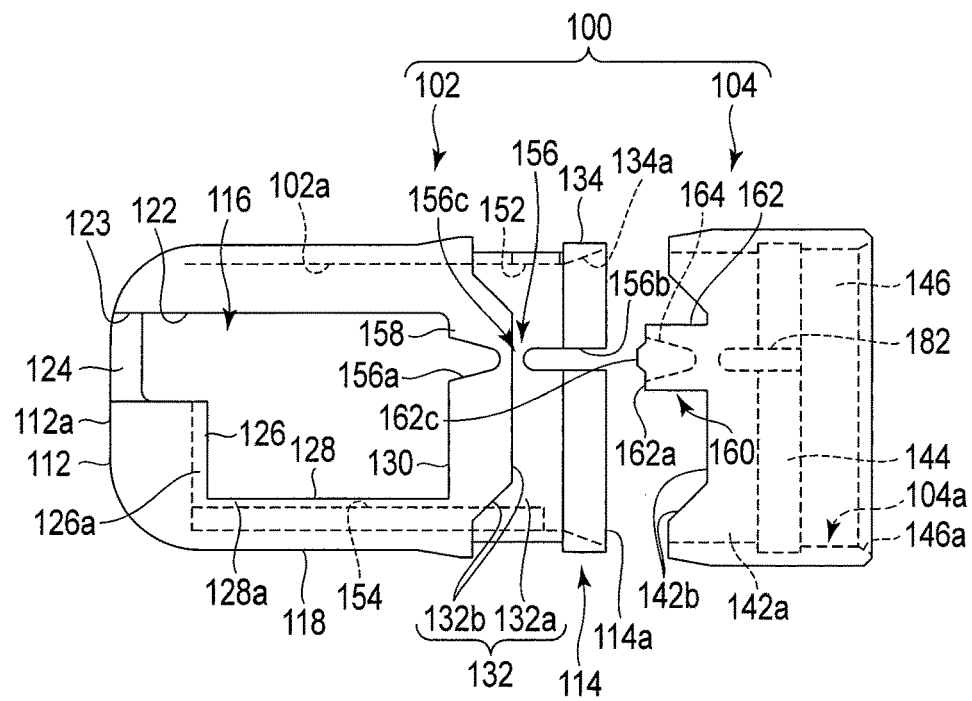
FIG. 11A is a schematic view showing an exploded state of the endoscope cover attached to the distal framing portion of the endoscope according to the second modification example of the first embodiment.
Figure 11B:
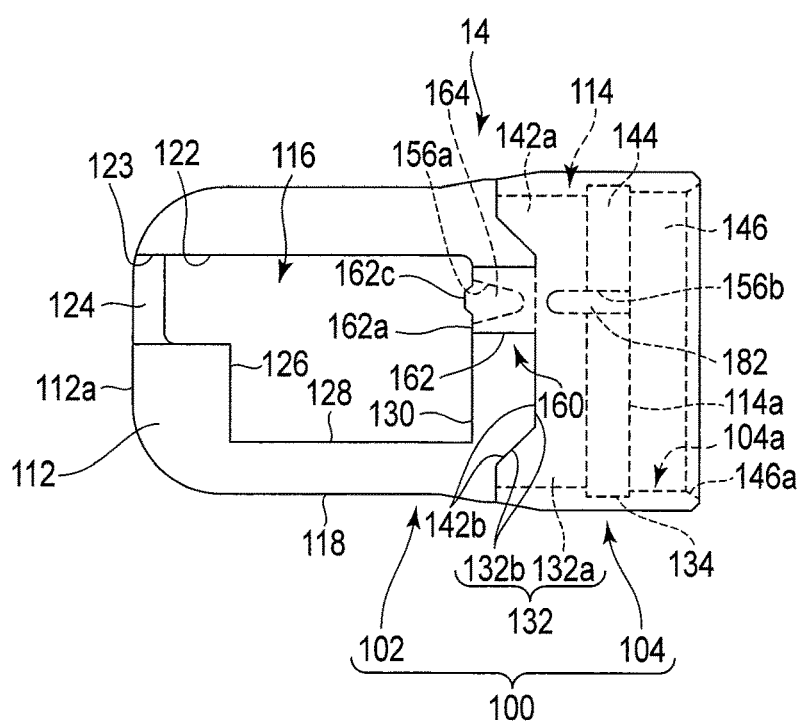
FIG. 11B is a schematic view showing the cover attached to the distal framing portion of the endoscope according to the second modification example of the first embodiment.

The second modification example will be described with reference to FIGS. 11A and 11B.

A projection 162c extending toward the distal side along the longitudinal axis L is formed on the end portion 162a of the extending portion 162. The projection 162c is located at a position which is distal to the proximal side edge 130 of the open edge 116 of the cover 14 along the longitudinal axis L. This modification example clarifies that the buffer portion 160 may have the end portion 162a at a position which is distal to the distal end position of the fragile portion 156 along the longitudinal axis L.

The projection 162c of the end portion 162a of the buffer portion 160 prevents the treatment instrument 20 and the like from directly coming into contact with the fragile portion 156 of the first cover main body 102. This makes it possible to reduce a load on the fragile portion 156 when, for example, the treatment instrument 20 comes into contact with the projection 162c of the end portion 162a of the extending portion 162 as compared with the first embodiment. When the swing table 42 is raised to the same position as that shown in FIG. 6C, the treatment instrument 20 can be fixed more reliably according to the amount of protrusion of the projection 162c. In addition, the projection 162c of the end portion 162a of the buffer portion 160 can prevent the fragile portion 156 from being broken even by an unintentional external load on the fragile portion 156 (application of unintentional force) owing to the buffer function of the projection 162c of the end portion 162a of the buffer portion 160 and the second cover main body 104.

The third modification example will be described with reference to FIGS. 12A to 12D.

Figure 12A:
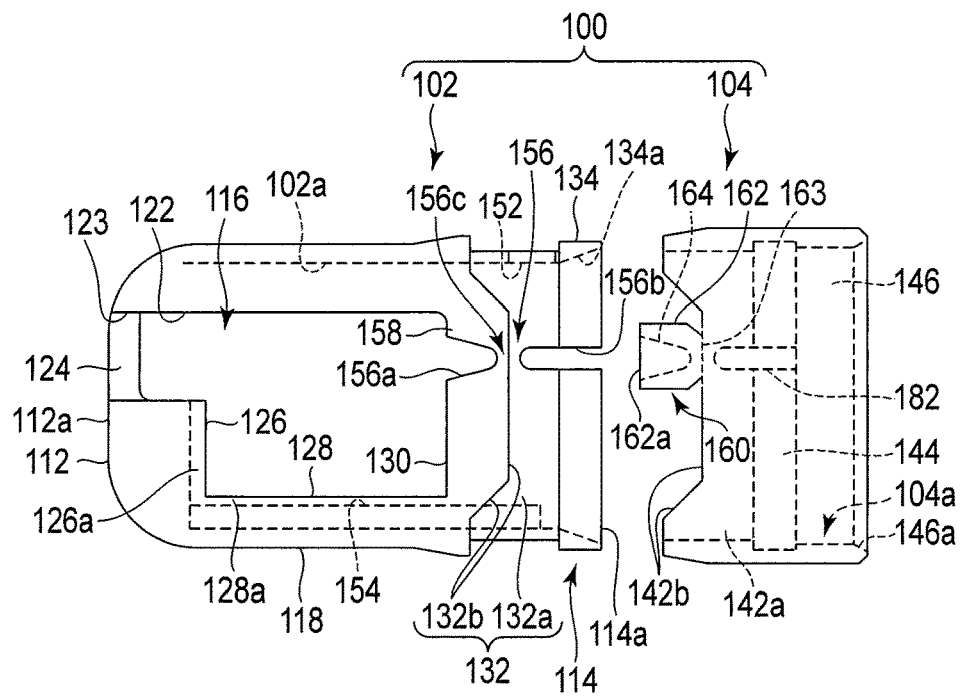
FIG. 12A is a schematic view showing an exploded state of the endoscope cover attached to the distal framing portion of the endoscope according to the third modification example of the first embodiment.
Figure 12B:
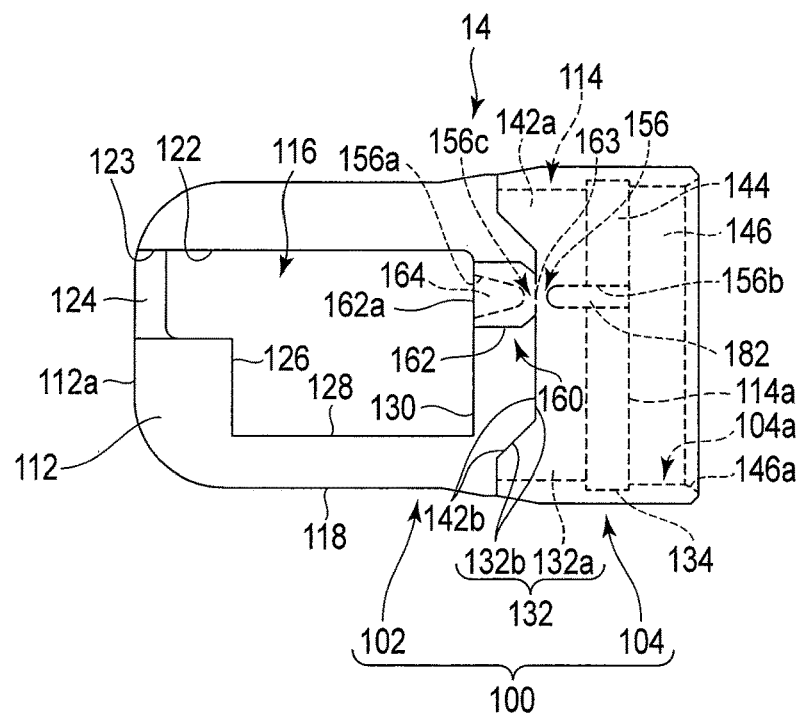
FIG. 12B is a schematic view showing the cover attached to the distal framing portion of the endoscope according to the third modification example of the first embodiment.
Figure 13A:
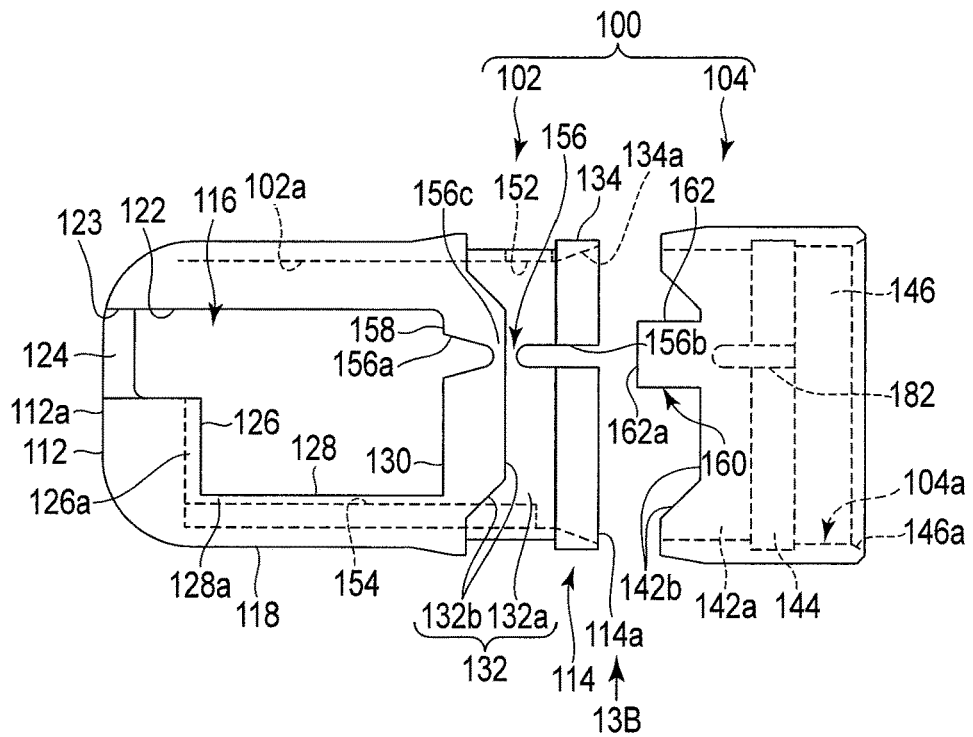
FIG. 13A is a schematic view showing an exploded state of the endoscope cover attached to the distal framing portion of the endoscope according to the fourth modification example of the first embodiment.
Figure 13B:
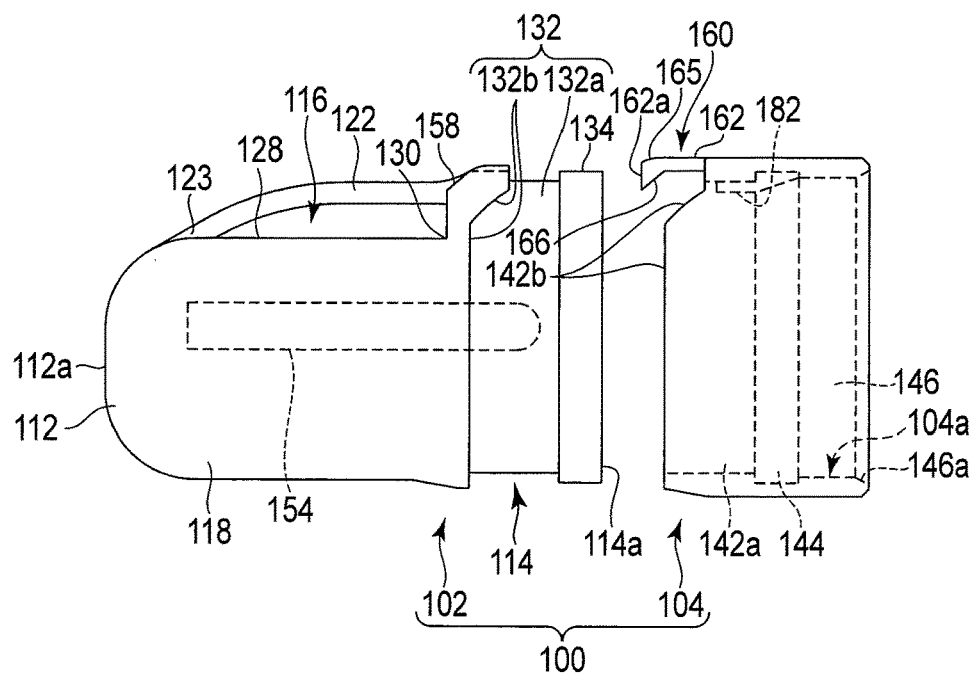
FIG. 13B is a view showing an exploded state of the cover attached to the distal framing portion of the endoscope according to the fourth modification example of the first embodiment, as viewed from the arrow 13B side in FIG. 13A.

A portion between the attachment protruding portion 142b of the second cover main body 104 and the proximal end of the extending portion 162 is formed as a cuttable portion 163 whose width in the circumferential direction with respect to the longitudinal axis L is reduced as appropriate. Referring to FIGS. 12A and 12B, although the second cover main body 104 and the extending portion 162 of the buffer portion 160 are integrally formed, the proximal end of the extending portion 162 can be cut from the attachment protruding portion 142b at the distal end of the second cover main body 104. As shown in FIGS. 12C and 12D, this makes it possible to use the extending portion 162 upon separating it from the distal end of the second cover main body 104. That is, the buffer portion 160 is detachable from the cover main body 100.

Obviously, as shown in FIGS. 12A and 12B, the extending portion 162 can be used without being separated from the distal end of the second cover main body 104.

When, for example, the endoscope 10 is used for a case in which the treatment instrument 20 needs to be fixed while being raised by the swing table 42, the extending portion 162 is used without being separated from the second cover main body 104. In contrast to this, when the endoscope 10 is used for a case in which the treatment instrument 20 need not be fixed while being raised by the swing table 42, the extending portion 162 may be used without being separated from the second cover main body 104 or upon being separated from the second cover main body 104.

The fourth modification example will be described with reference to FIGS. 13A to 14B.

Figure 14A:
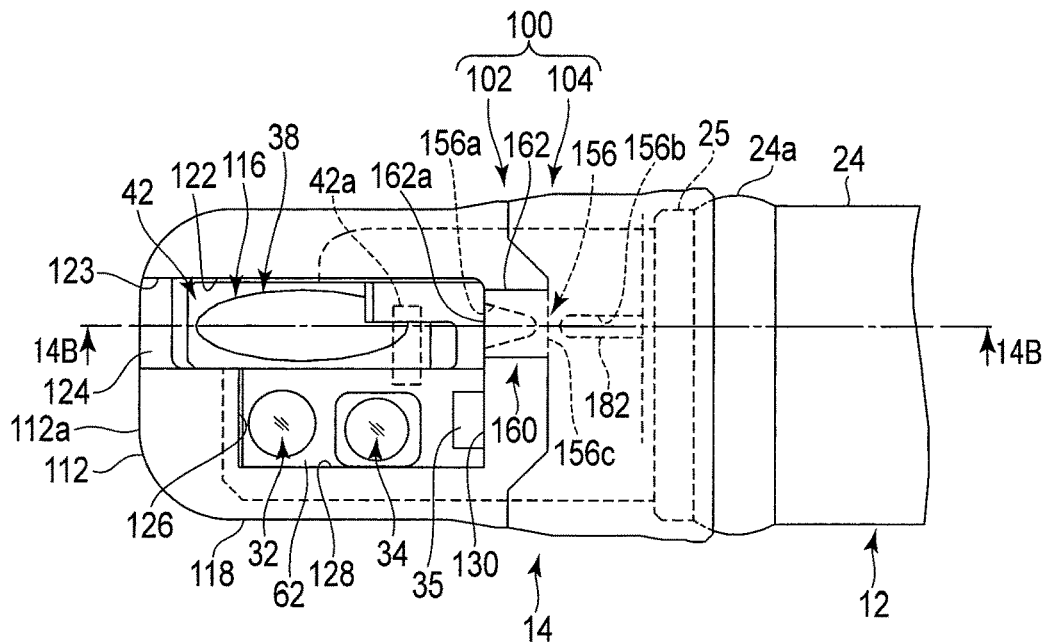
FIG. 14A is a schematic view showing a state in which the cover is attached to the distal framing portion of the endoscope according to the fourth modification example of the first embodiment.
Figure 14B:
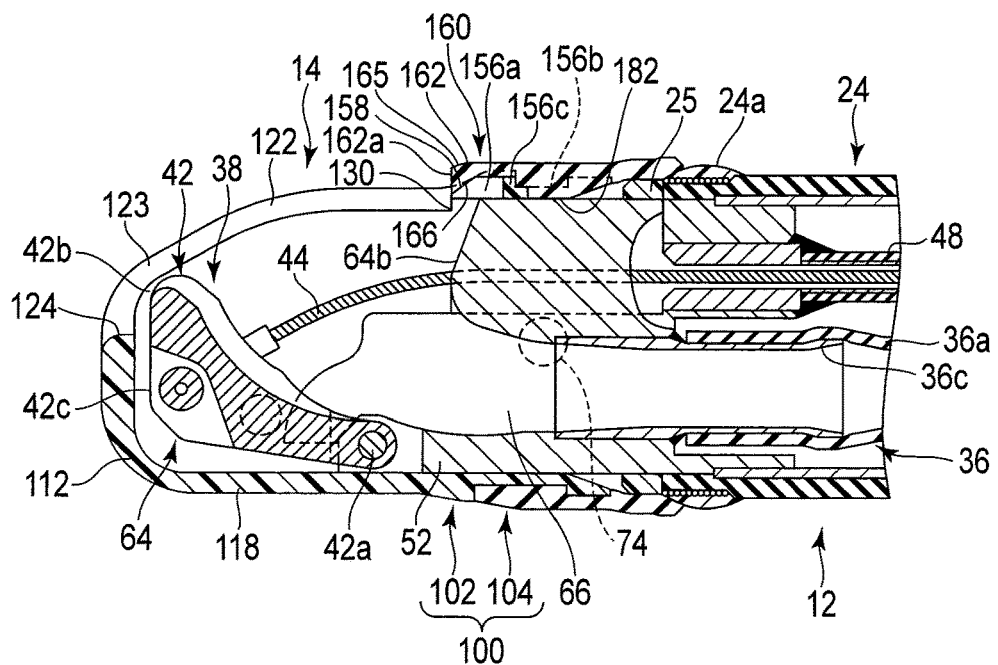
FIG. 14B is a schematic sectional view taken along line 14B-14B in FIG. 14A.
Figure 15A:
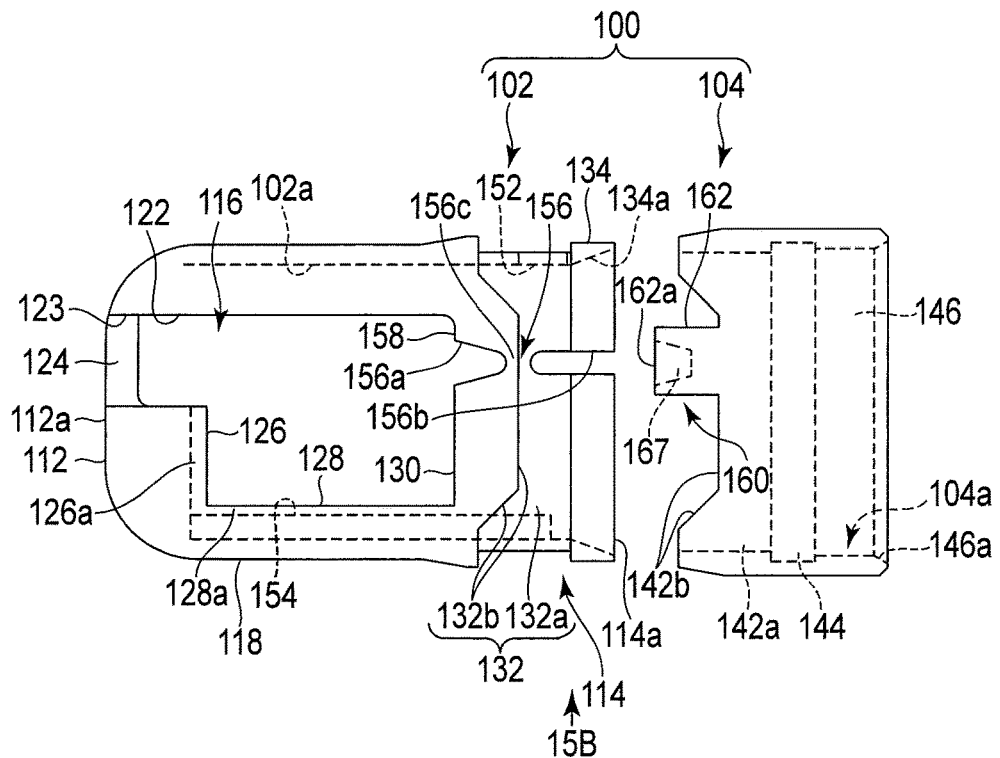
FIG. 15A is a schematic view showing an exploded state of the endoscope cover attached to the distal framing portion of the endoscope according to the fifth modification example of the first embodiment.
Figure 15B:
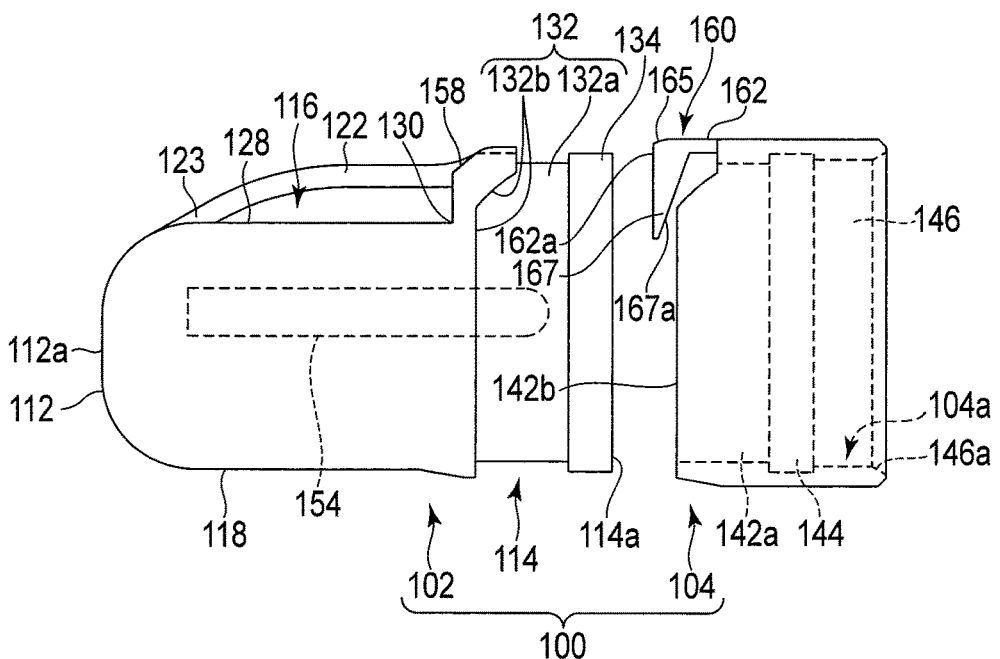
FIG. 15B is a view showing an exploded state of the cover attached to the distal framing portion of the endoscope according to the fifth modification example of the first embodiment, as viewed from the arrow 15B side in FIG. 15A.
Figure 16A:
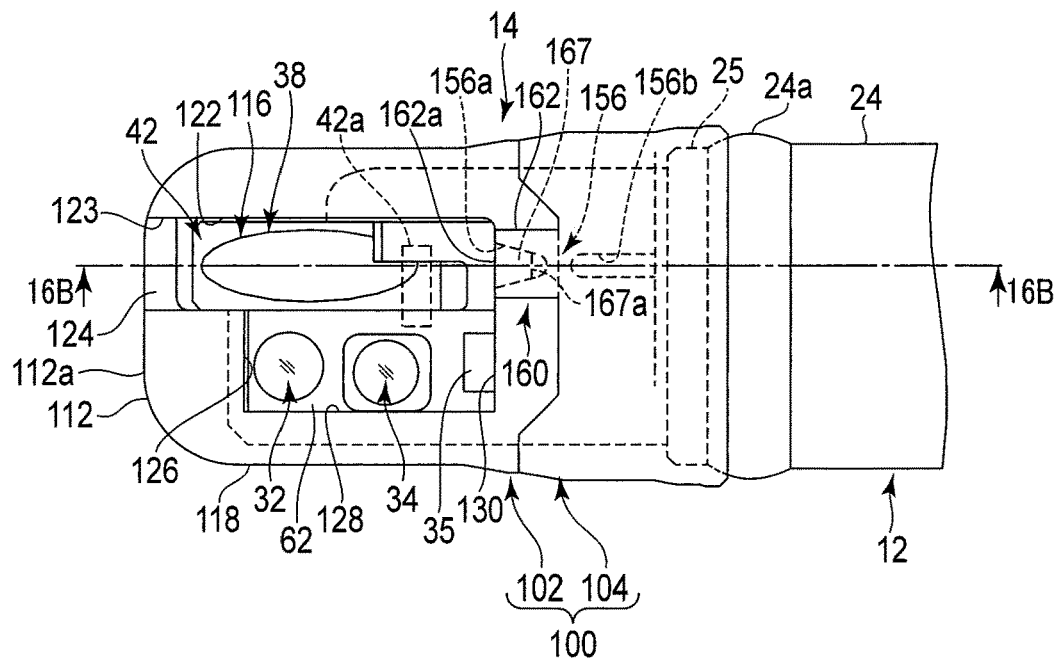
FIG. 16A is a schematic view showing a state in which the cover is attached to the distal framing portion of the endoscope according to the fifth modification example of the first embodiment.
Figure 16B:
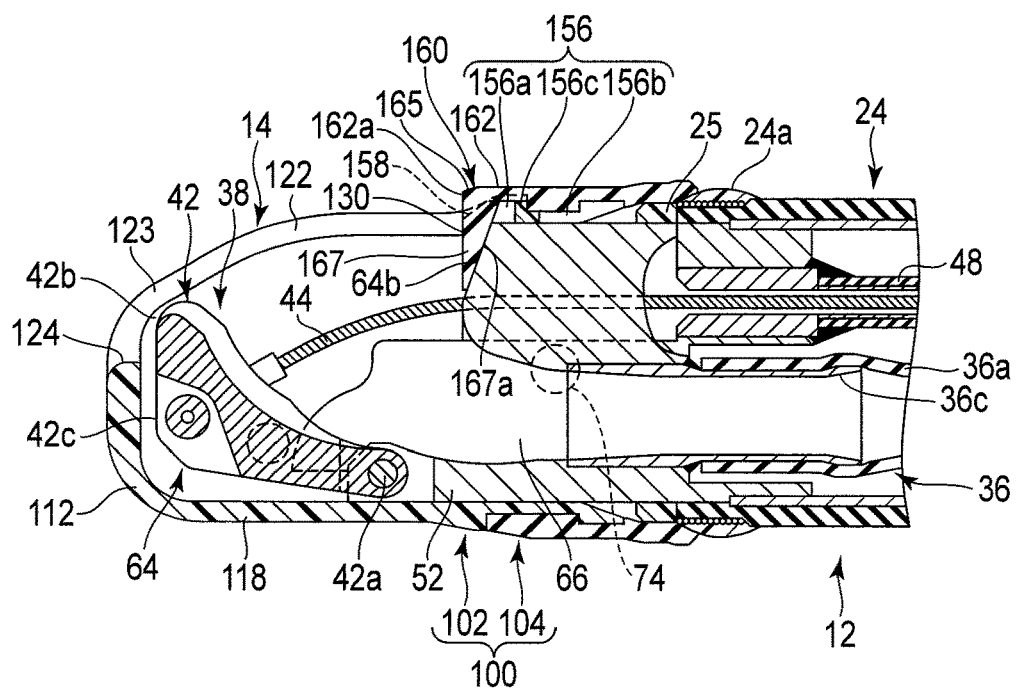
FIG. 16B is a schematic view taken along line 16B-16B in FIG. 16A.

The protruding portion 164 (see FIGS. 4B, 4D, and 5E) is not formed on the extending portion 162. As shown in FIG. 14B, the inclined plane 158 of the first cover main body 102 is brought into contact with the inclined plane 166 of the second cover main body 104. At this time, the inclined plane 166 of the extending portion 162 is separated from the coupling portion 156c of the fragile portion 156. This can reliably prevent a load from being exerted on the coupling portion 156c of the fragile portion 156 when the raised treatment instrument 20 comes into contact with the end portion 162a of the extending portion 162. In addition, the end portion 162a of the buffer portion 160 can prevent the fragile portion 156 from being broken by an unintentional external force on the fragile portion 156 (application of unintentional force) owing to the buffer effect of the buffer portion 160 and the second cover main body 104.

The fifth modification example will be described with reference to FIGS. 15A to 16B.

The extending portion 162 has a protruding portion (attachment portion) 167 protruding toward the inside of the cover 14. The protruding portion 167 of the extending portion 162 has an inclined plane 167a that comes into contact with the wall surface 64b of the recess portion 64 storing the swing table 42. The inclined plane 167a allows the protruding portion 167 of the extending portion 162 to be fitted to the wall surface 64b of the recess portion 64.

Part of the protruding portion 167 is disposed in the slit (breakage inducing path) 156a of the fragile portion 156. On the other hand, the protruding portion 167 is separated from the coupling portion 156c of the fragile portion 156 along the longitudinal axis L. This makes it possible to reliably prevent a load from being exerted on the coupling portion 156c of the fragile portion 156 when the raised treatment instrument 20 comes into contact with the end portion 162a of the extending portion 162. In addition, the end portion 162a of the buffer portion 160 can prevent the fragile portion 156 from being broken even by an unintentional external force on the fragile portion 156 (unintentional exertion of a force) owing to the buffer effect of the buffer portion 160 and the second cover main body 104.

The sixth modification example will be described with reference to FIGS. 17A to 18B.

The following will describe a case in which the slit (breakage inducing path) 156a (see FIG. 4A) continuous with the proximal side edge 130 of the open edge 116 is not formed out of the fragile portion 156. The distal end of the slit (breakage inducing path) 156b of the fragile portion 156, which is continuous with the proximal end 114a of the annular portion 114, is continuously formed to near the proximal side edge 130 of the open edge 116, exceeding the attachment portion 132 of the annular portion 114. This is for the purpose of defining a breakage position (breakage region) at a predetermined position when breaking the fragile portion 156.

The extending portion 162 of the buffer portion 160 has a protruding portion (attachment portion) 168 protruding toward the inside of the cover 14. The protruding portion 168 of the extending portion 162 has the inclined plane 166 that comes into contact with the inclined plane 158 of the first cover main body 102.

Part of the protruding portion 168 is disposed distal to the distal end of the slit 156b of the fragile portion 156 and the proximal side edge 130 of the open edge 116 along the longitudinal axis L. The extending portion 162 covers the outer peripheral surface of the fragile portion 156 in cooperation with the second cover main body 104. This makes it possible to reliably prevent a load from being exerted on the coupling portion 156c of the fragile portion 156 when the raised treatment instrument 20 comes into contact with the end portion 162a of the extending portion 162. Note that the coupling portion 156c in this case is formed between the proximal side edge 130 of the open edge 116 and the distal end of the slit 156b.

According to this modification example, when the cover 14 is broken, breakage is generated in a predetermined region between the proximal side edge 130 of the open edge 116 and the distal end of the slit 156b of the fragile portion 156. As in this case, when the cover 14 is intentionally broken, breakage can be reliably generated in the predetermined region between the proximal side edge 130 of the open edge 116 and the distal end of the slit 156b of the fragile portion 156. In this state, a region in which breakage is generated is adjacent to the fragile portion 156 regardless of distance.

The seventh modification example will be described with reference to FIGS. 19A to 20B.

In this modification example, the width of the slit (breakage inducing path) 156a of the fragile portion 156 in the circumferential direction is changed. That is, the slits 156a and 156b of the fragile portion 156 may have different widths in the circumferential direction. In addition, as the width of the slit 156a is changed, the shape and width of the protruding portion 164 of the extending portion 162 are changed. In this case, the inclined plane 166 is not formed on the extending portion 162. Obviously, however, the inclined plane 166 may be formed on the extending portion 162.

The proximal end of the protruding portion 164 is in contact with the proximal end of the slit 156a of the fragile portion 156, i.e., the distal end of the coupling portion 156c of the fragile portion 156. In this case, the contact area between the proximal end of the protruding portion 164 and the coupling portion 156c is larger than that in the first embodiment. For this reason, even when the raised treatment instrument 20 comes into contact with the end portion 162a of the extending portion 162, stress does not easily concentrate on the coupling portion 156c of the fragile portion 156, and hence the fragile portion 156 is not easily broken.

The eighth modification example will be described with reference to FIGS. 21A to 22B.

The distal end of the slit 156a of the fragile portion 156 of the first cover main body 102 is formed continuously with the right side edge 122 of the open edge 116.

In this case, the buffer portion 160 does not have the extending portion 162 extending from the second cover main body 104. The buffer portion 160 has the end portion 162a at the distal end of the second cover main body 104.

Figure 22A:
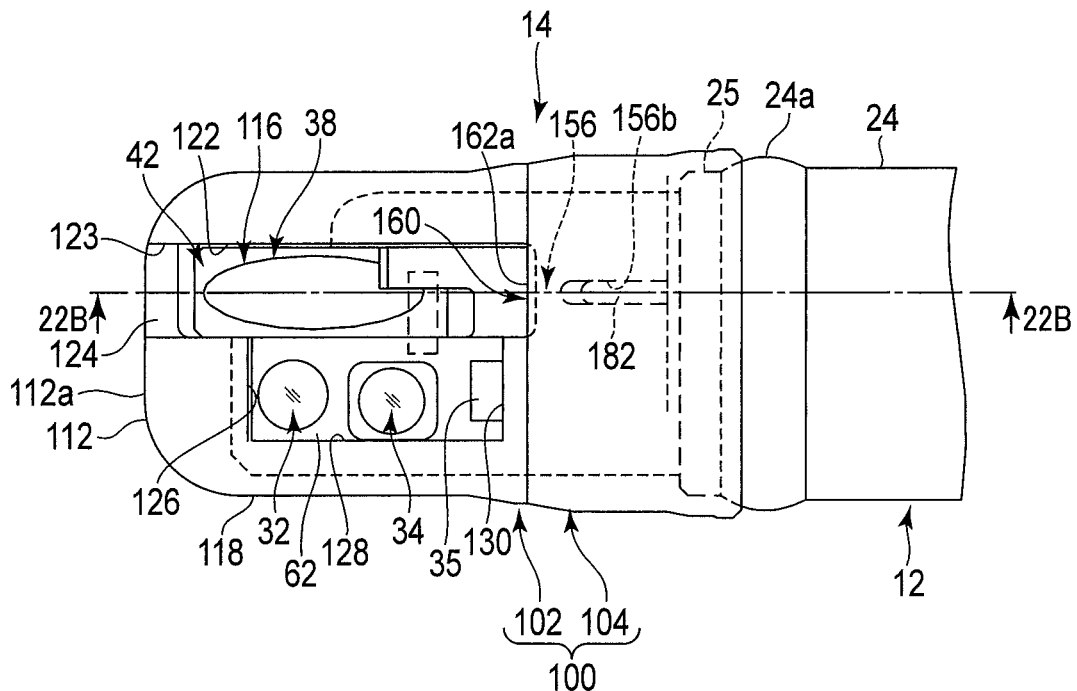
FIG. 22A is a schematic view showing a state in which the cover is attached to the distal framing portion of the endoscope according to the eighth modification example of the first embodiment.
Figure 22B:
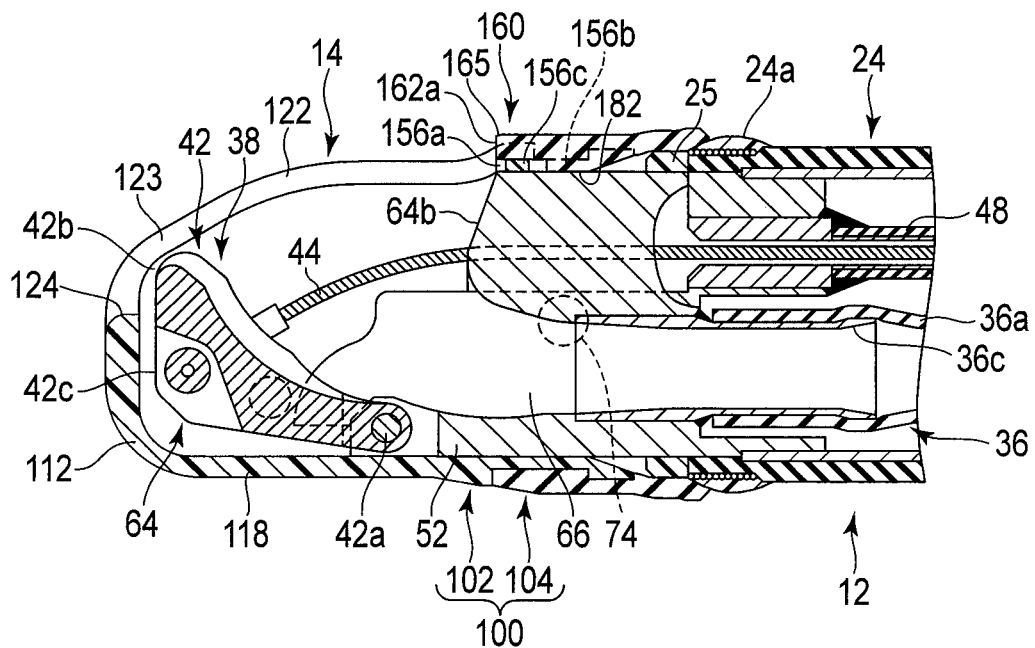
FIG. 22B is a schematic sectional view taken along line 22B-22B in FIG. 22A.

As shown in FIG. 22A, the end portion 162a of the buffer portion 160 comes into contact with the treatment instrument 20 before the distal end of the coupling portion 156c of the fragile portion 156 comes into contact with the treatment instrument 20. The second cover main body 104 is formed from a rubber material. This reduces a load on the coupling portion 156c of the fragile portion 156.

The extending portion 162 (see FIGS. 4A to 4D) need not always be formed on the buffer portion 160.

Figure 23:
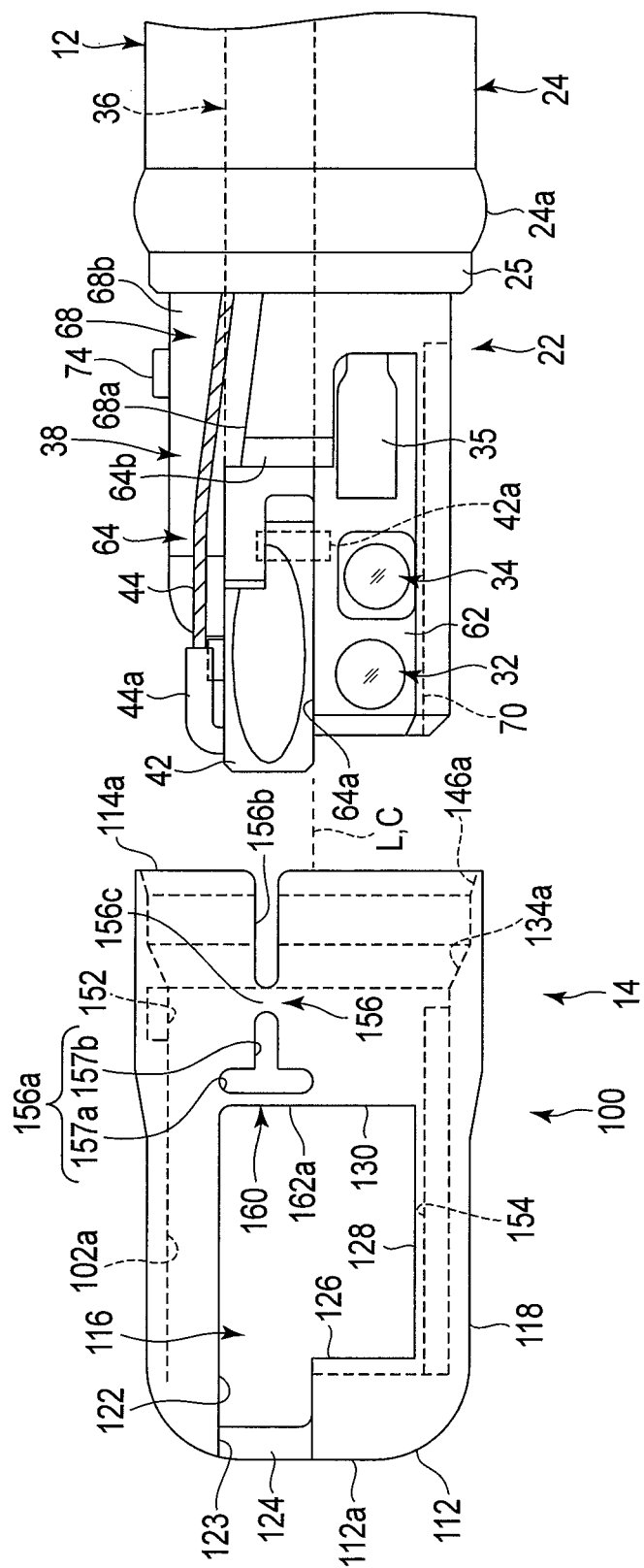
FIG. 23 is a schematic view showing a state in which the distal framing portion of an endoscope according to the second embodiment is made to face the proximal side of an endoscope cover to be inserted into the cover.

The second embodiment will be described next with reference to FIGS. 23 to 24B. This embodiment is a modification example of the first embodiment including the respective modification examples. The same reference numerals denote, as much as possible, the same members or members having the same functions as those in the first embodiment, and a detailed description of the members will be omitted.

Figure 24A:
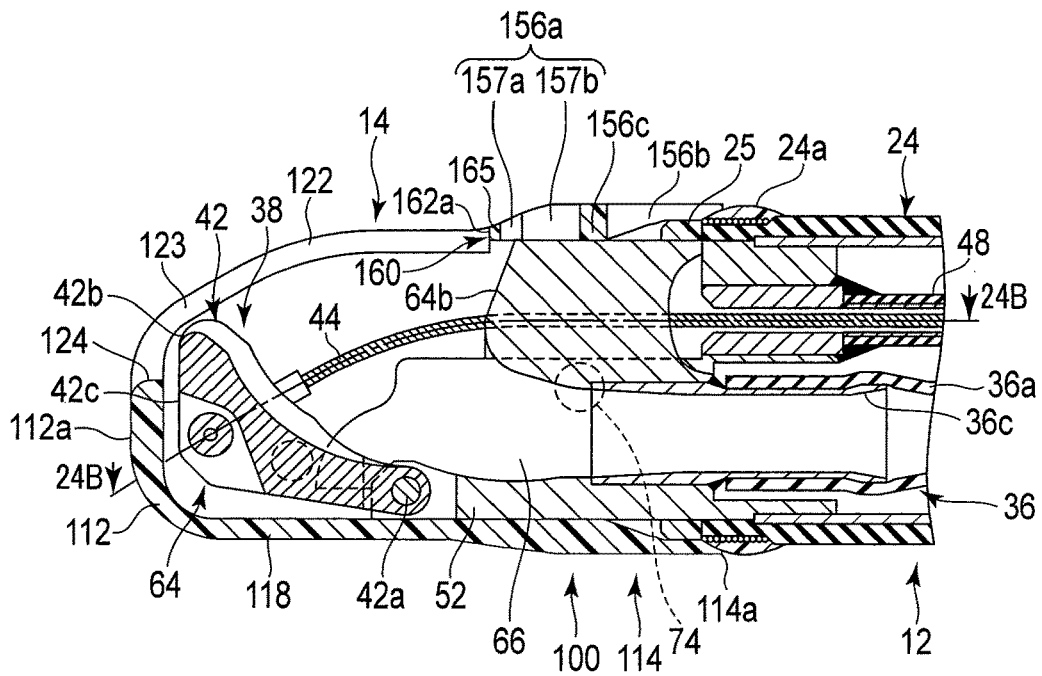
FIG. 24A is a schematic view showing a partial section at a position along line 24A-24A in FIG. 24B in a state in which the cover is attached to the distal framing portion of the endoscope shown in FIG. 23.
Figure 24B:
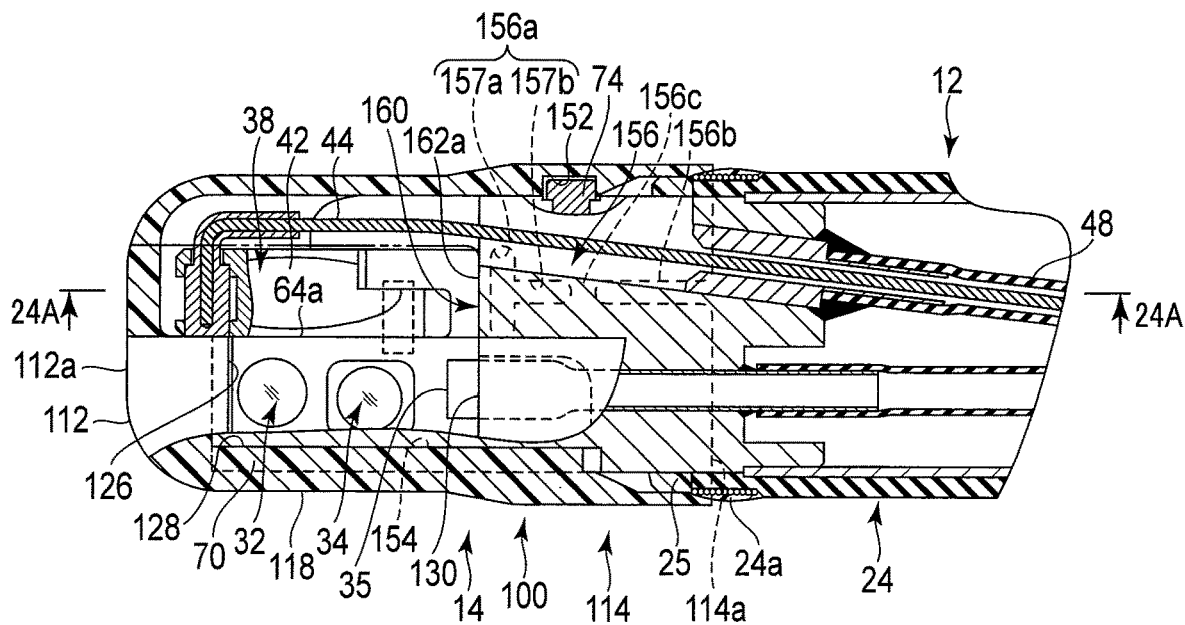
FIG. 24B is a schematic view partially showing a state in which the cover is attached to the distal framing portion of the endoscope shown in FIG. 23 and also showing a partial section at a position along line 24B-24B in FIG. 24.

As shown in FIG. 24, a cover 14 according to this embodiment includes a cover main body 100 attached to a distal framing portion 22 along a longitudinal axis L of an insertion section 12. The cover main body 100 according to the embodiment integrates the functions of the first cover main body 102 and the second cover main body 104 (see FIGS. 4A to 5C) described in the first embodiment. The cover main body 100 is formed from, for example, a resin material (plastic material) in an integrally cylindrical shape (bombshell shape). The cover main body 100 is preferably formed from a material having electrical insulation properties. Examples of the plastic material of the cover main body 100 include polysulfone, polyethylene, and polycarbonate. The inner diameter of the cover main body 100, that is, the inner peripheral surface, is formed in an appropriate size and shape based on the size of the distal framing portion 22.

The fragile portion 156 of the cover main body 100 includes slits (breakage inducing paths) 156a and 156b and a coupling portion 156c. The coupling portion 156c is formed between the slits 156a and 156b. In this case, the second cover main body 104 described in the first embodiment is not used, and hence the fragile portion 156 is exposed to the outside.

The first slit 156a according to this embodiment is formed into a substantially T shape. The first slit 156a integrally has a slit 157a extending almost parallel to the proximal side edge 130 and a slit 157b that is orthogonal to the proximal side edge 130 and extends from the slit 157a toward the proximal side along the longitudinal axis L.

A buffer portion 160 is provided such that the slit 156a and a proximal side edge 130 of an open edge 116 are not continuous with each other. The buffer portion 160 has an end portion (distal end portion) 162a at a position which is distal to the distal end position of a fragile portion 156 along the longitudinal axis L. Although not shown, an inclined plane 165 (see FIGS. 4D and 5E) is preferably formed at a position adjacent to the end portion 162a. The end portion 162a of the buffer portion 160 is provided at a position to come into contact with the treatment instrument 20 protruding from the cover main body 100 via the open edge 116 when a treatment instrument 20 is raised by a swing table 42 as described in the first embodiment. The buffer portion 160 is provided for the cover main body 100 and has the end portion 162a formed as part of the proximal side edge 130 of the open edge 116 at a position which is distal to the distal end position of the fragile portion 156 along the longitudinal axis L. The buffer portion 160 is used to reduce a force exerted from the distal side of the fragile portion 156 onto the fragile portion 156.

The cover main body 100 is positioned to the distal framing portion 22 in a state in which the buffer portion 160 and the fragile portion 156 are provided on a straight line along the longitudinal axis L relative to the swing table 42.

Note that the cover main body 100 of the cover 14 according to this embodiment has a lock depressed portion 152 locked to the distal framing portion 22. The lock depressed portion 152 is unlocked from the distal framing portion 22 by breaking the fragile portion 156 of an annular portion 114 as in the first embodiment. That is, the buffer portion 160 allows breakage in the fragile portion 156 when a load is exerted on the annular portion 114 in a state in which it is separated along the circumferential direction. In the embodiment, breakage is generated first in the coupling portion 156c between the proximal end of the first slit 156a and the distal end of the second slit 156b. It is assumed that as the displacement of the annular portion 114 increases, the breakage extends, and the breakage region extends to the buffer portion 160 and reaches the proximal side edge 130 of the open edge 116. Accordingly, breakage is generated between one of the positions of the first slit 156a and the slit 157a in the circumferential direction relative to the longitudinal axis L and the proximal side edge 130 of the open edge 116 and in the coupling portion 156c. As a consequence, the open edge 116 and the proximal end 114a of the annular portion 114 become continuous with each other. This allows the user to remove the cover 14 from the distal framing portion 22.

Accordingly, the extending portion 162 (see FIGS. 4A to 4D) need not always be formed on the buffer portion 160. In addition, the buffer portion 160 need not always cover the outside of the fragile portion 156.

The end portion 162a of the buffer portion 160 of the cover 14 can hold and fix the treatment instrument 20 between itself and the swing table 42 raised by the operation of a lever 46. This allows the buffer portion 160 of the cover 14 to suppress the movement of the treatment instrument 20 in its axial direction while the swing table 42 is raised.

Raising the swing table 42 will cause the treatment instrument 20 to come into contact with the end portion 162a of the buffer portion 160 of the cover 14. At this time, a load is exerted on the fragile portion 156 via the buffer portion 160. However, the buffer function of the buffer portion 160 and the resistance property of the fragile portion 156 can prevent the fragile portion 156 from being broken.

The buffer function of the buffer portion 160 can also prevent the fragile portion 156 from being broken even if an unintentional load is externally exerted (application of unintentional force) on the fragile portion 156 from the distal side to the proximal side along the longitudinal axis L.

The buffer portion 160 actively buffers a load in a direction along the longitudinal axis L and prevent an object from hitting the end face of the fragile portion 156. On the other hand, the buffer portion 160 is not structured to actively suppress the breakage of the annular portion 114 along the longitudinal axis L. Accordingly, when the user removes the cover 14 from the distal framing portion 22, he/she can break the coupling portion 156c of the fragile portion 156 by exerting a force on the coupling portion 156c in, for example, the circumferential direction, thus easily removing the cover 14 from the distal framing portion 22.

This embodiment can therefore provide the endoscope cover 14 and an endoscope 10 which can suppress the exertion of a load on the fragile portion 156 when, for example, the insertion section 12 is inserted into the body or while the insertion section 12 is used during insertion into the body, as described in the first embodiment.

The first modification example will be described with reference to FIG. 25.

The cover 14 according to this modification example has the fragile portion (breakage inducing region) 156 formed into a thin portion instead of a slit (notched portion). As described above, the fragile portion (breakage inducing portion) 156 need not always make the inner peripheral surface and the outer peripheral surface of the cover main body 100 communicate with each other.

The buffer portion 160 is formed on a thick portion 170 thicker than the fragile portion 156. It is also preferable that the thick portion 170 of the buffer portion 160 is formed by integrally molding, for example, a block-shaped rubber material between the proximal side edge 130 of the open edge 116 and the distal end of the fragile portion 156.

Note that the first embodiment has exemplified the case in which the fragile portion 156 of the first cover main body 102 of the cover main body 100 has the slits 156a and 156b (see FIG. 4A) to make the inside and the outside of the first cover main body 102 communicate with each other. Obviously, the slits 156a and 156b of the fragile portion 156 described in the first embodiment may be formed into thin portions as in this modification example.

The second modification example will be described with reference to FIG. 26.

The buffer portion 160 is fixed near the boundary between the proximal side edge 130 of the open edge 116 and the distal end of the first slit 156a of the fragile portion 156. The buffer portion 160 is preferably formed from a rubber material or the like.

The buffer portion 160 has a T-shaped member 174 integrally formed with a thin portion 172. The T-shaped member 174 has a lateral bar 174a extending parallel to the proximal side edge 130 and supported by the proximal side edge 130 and a longitudinal bar 174b fitted in the first slit 156a. A portion of the lateral bar 174a which faces the distal side edge 126 of the open edge 116 forms the end portion 162a of the buffer portion 160.

The buffer portion 160 may be detachable from the cover main body 100 as long as the buffer portion 160 is kept fixed to the cover main body 100 during the use of the endoscope 10.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endo scope cover for attachment to a distal framing portion of an insertion section of an endoscope, the cover comprising:
   a cover main body configured to be attached to the distal framing portion from a distal side along a longitudinal axis of the insertion section, the cover main body comprising:
      a window opening in a radial direction of the longitudinal axis of the insertion section,
      an annular portion provided on a proximal side of the window along the longitudinal axis of the insertion section and surrounding the distal framing portion;
      a fragile portion provided in a longitudinal direction between a proximal edge of the window and a proximal end of the annular portion, the fragile portion forming a region being more fragile relative to adjacent regions of the annular portion in the longitudinal direction; and
      a buffer material provided on the cover main body, the buffer material including an end portion, the end portion extending distally to at least a same position as a distal end position of the fragile portion along the longitudinal direction, the end portion of the buffer material being configured to reduce a force exerted from a distal side of the fragile portion onto the fragile portion along the longitudinal direction.

2. The cover of claim 1, wherein:
   the cover main body includes:
      a first cover main body including the annular portion and covering the distal framing portion, and
      a second cover main body covered by an outer periphery of the annular portion on a proximal side of the first cover main body, and
   the buffer material is provided on a distal side of the second cover main body and covers an outside of the fragile portion.

3. The cover of claim 2, wherein the buffer material includes a projection provided on a distal end of the second cover main body, the projection being configured to extend toward a distal side of the annular portion.

4. The cover of claim 2, wherein:
   the fragile portion includes one or more slits configured to cause a breakage in part of the annular portion of the cover main body by exerting a stress on the part of the annular portion in a predetermined direction the one or more slits being configured to induce the breakage in region when the cover main body is removed from the distal framing portion, and the buffer material has a shape covering the one or more slits.

5. The cover of claim 4, wherein:
the one or more slits comprise first and second slits configured to induce the breakage in the region when the breakage is generated when the cover main body is removed from the distal framing portion, and
the second cover main body has a shape covering the first and second slits.

6. The cover of claim 4, wherein the buffer material includes a projection engaged with the one or more slits so as to position the second cover main body to the first cover main body.

7. The cover of claim 2, wherein:
the first cover main body is formed from a material having an electrical insulation property, and
the second cover main body is formed from a material having an electrical insulation property and higher flexibility than the first cover main body.

8. The cover of claim 1, wherein when the cover main body is attached to the distal framing portion, the window is configured to expose an observation optical system provided in the distal framing portion.

9. The cover of claim 1, wherein:
when the cover main body is attached to the distal framing portion, the window allows a treatment instrument extending from a swing table of the distal framing portion through the insertion section to protrude outside via the window, and
the end portion of the buffer portion is configured to support the treatment instrument and is configured to suppress movement of the treatment instrument in an axial direction when the treatment instrument extending from the distal framing portion via the insertion section comes into contact with the end portion of the buffer material in accordance with a position of the swing table is changed.

10. The cover of claim 9, wherein the cover main body is positioned to the distal framing portion in a state in which the end portion of the buffer material and the fragile portion are provided on a straight line along the longitudinal axis.

11. The cover of claim 10, wherein:
the fragile portion has a resistance property that prevents occurrence of the breakage in the part of the annular portion of the cover main body while the treatment instrument is supported on the end portion of the buffer material and a stress is exerted on the annular portion in the predetermined direction, and
the fragile portion causes the breakage between a proximal end of the window and a proximal end of the cover main body so as to remove the cover main body from the distal framing portion when a load is exerted on the annular portion in a circumferential direction of the longitudinal axis.

12. The cover of claim 1, wherein the end portion of the buffer material is located at the same position as a position of an edge of the window or a position protruding to the distal side with respect to the edge of the window along the longitudinal axis.

13. The cover of claim 1, wherein:
the cover main body includes a lock portion comprising one of a concavity or a projection configured to be locked to an other of the concavity or the projection provided on the distal framing portion, the lock portion being configured to suppress movement of the cover main body around the longitudinal axis relative to the distal framing portion.

14. The cover of claim 1, wherein the buffer material is formed from a material having an electrical insulation property and is integrally formed with the cover main body.

15. The cover of claim 1, wherein the buffer material is formed from a material having an electrical insulation property and is configured to be removed from the cover main body.

16. The cover of claim 1, wherein a material of the buffer material has higher flexibility than a material of the cover main body.

17. An endoscope comprising:
the endoscope cover of claim 1; and
the insertion section including the distal framing portion at the distal end portion of the insertion section;
wherein the endoscope cover is attached to the distal framing portion.

18. The cover of claim 1, wherein the fragile portion forming the region in the longitudinal direction of the annular portion having a smaller cross-sectional area than the adjacent regions in the longitudinal direction.

19. The endoscope of claim 17, wherein:
the distal framing portion is configured to guide a treatment instrument to outside of the distal framing portion via the insertion section,
the window allows the treatment instrument guided by the distal framing portion to protrude outside the cover via the window, and
the end portion of the buffer material allows the treatment instrument to be supported in a state in which movement of the treatment instrument is suppressed in an axial direction when the treatment instrument extending from the distal framing portion via the insertion section comes into contact with the end portion of the buffer material.

20. An endoscope cover for attachment to a distal end of an insertion section of an endoscope, the cover comprising:
a cover main body configured to be attached to the distal end of the insertion section, the cover main body comprising:
an annular portion provided on a proximal side of the cover main body along the longitudinal axis of the insertion section and surrounding the distal end of the insertion section;
a fragile portion provided at a position on the annular portion, the fragile portion forming a region in a longitudinal direction of the annular portion having a smaller cross-sectional area than adjacent regions of the annular portion in the longitudinal direction; and
a buffer material provided on the cover main body, the buffer material including an end portion, the end portion extending distally to at least a same position as a distal end position of the fragile portion along the longitudinal axis, the end portion of the material being configured to reduce a force exerted from a distal side of the fragile portion onto the fragile portion along the longitudinal direction.

21. The cover of claim 20,
further comprising a window opening in a radial direction of the longitudinal axis of the insertion section,
wherein the fragile portion is provided in the longitudinal direction between a proximal edge of the window and a proximal end of the annular portion.

22. An endoscope cover for attachment to a distal end of an insertion section of an endoscope, the cover comprising:
- a cover main body configured to be attached to the distal end of the insertion section, the cover main body comprising:
  - an annular portion provided on a proximal side of the cover main body along the longitudinal axis of the insertion section and surrounding the distal end of the insertion section;
  - a fragile portion provided at a position on the annular portion, the fragile portion forming a region in a longitudinal direction of the annular portion being more fragile relative to adjacent regions of the annular portion in the longitudinal direction; and
- a buffer material provided on the cover main body, the buffer material including an end portion, the end portion extending distally to at least a same position as a distal end position of the fragile portion along the longitudinal direction, the end portion of the buffer material being configured to reduce a force exerted from a distal side of the fragile portion onto the fragile portion along the longitudinal direction.

23. The cover of claim 22,
further comprising a window opening in a radial direction of the longitudinal axis of the insertion section,
wherein the fragile portion is provided in the longitudinal direction between a proximal edge of the window and a proximal end of the annular portion.

\* \* \* \* \*